United States Patent
Bogdahn et al.

(10) Patent No.: US 8,022,045 B1
(45) Date of Patent: Sep. 20, 2011

(54) INHIBITORS OF TGF-R-SIGNALING FOR TREATMENT OF CNS DISORDERS

(75) Inventors: Ulrich Bogdahn, Regensburg (DE);
Ludwig Aigner, Regensburg (DE);
Frank-Peter Wachs, WeBling (DE);
Beate Winner, Regensburg (DE);
Jürgen Winkler, Lappersdorf (DE)

(73) Assignees: Ulrich Bogdahn, Regensburg (DE);
Ludwig Aigner, Salzburg (AT)

( * ) Notice: Subject to any disclaimer, the term of this patent is extended or adjusted under 35 U.S.C. 154(b) by 0 days.

(21) Appl. No.: 10/597,813

(22) PCT Filed: Feb. 9, 2005

(86) PCT No.: PCT/EP2005/001298
§ 371 (c)(1),
(2), (4) Date: Apr. 13, 2007

(87) PCT Pub. No.: WO2005/074981
PCT Pub. Date: Aug. 18, 2005

(30) Foreign Application Priority Data

Feb. 9, 2004 (EP) .................................. 04002846

(51) Int. Cl.
*C12N 15/11* (2006.01)
*C07H 21/02* (2006.01)
*C07H 21/04* (2006.01)

(52) U.S. Cl. ..... 514/44; 536/23.1; 536/24.3; 536/24.33; 536/24.5

(58) Field of Classification Search ................. 536/23.1, 536/24.3, 24.33, 24.5; 435/6, 91.1, 325, 435/375; 514/44
See application file for complete search history.

(56) References Cited

FOREIGN PATENT DOCUMENTS

| | | | |
|---|---|---|---|
| WO | WO 01/01961 | | 1/2001 |
| WO | WO 03/000656 | * | 1/2003 |
| WO | WO 03/056013 | | 7/2003 |

OTHER PUBLICATIONS

Ogorelkova et al. (Oligonucleotides, 2006 vol. 16:2-14).*
Jason Liu et al., "Transforming Growth Factor β2, But Not β1 and β3, Is Critical for Early Rat Lung Branching" Developmental Dynamics, 2000, No. 217, pp. 343-360.
Blast Alignment of Sequence, ID No: 3.
Sequence of TGF-$R_{II}$.
European Search Report of European Application No. 04002846.6-1212, dated on Oct. 21, 2004.
Frederick L Hall et al, "Transforming growth factor-β type-II receptor signalling: intrinsic/associated casein kinase activity, receptor interactions and functional effects of blocking antibodies" Biochem-J, (1996), vol. 316, pp. 303-310.
Sylviane Komesli et al., "Chimeric extracellular domain of type II transforming growth factor (TGF)-β receptor fused to the Fc region of human immunoglobulin as a TGF-β antagonist" European Journal of Biochemistry, Jun. 15, 1998, vol. 254, No. 3, pp. 505-513.

(Continued)

Primary Examiner — Terra Cotta Gibbs
(74) Attorney, Agent, or Firm — J.C. Patents

(57) ABSTRACT

The present invention relates to the use of oligonucleotides for the preparation of a pharmaceutical composition for the prevention or treatment of a disease, wherein neurogenesis and/or neuroregeneration has a beneficial effect, in particular a disease like Morbus Alzheimer, Morbus Parkinson, Lewy Body Dementia, Amyotrophic Lateral Sclerosis, Spinocerebellar Atrophies, Creutzfeldt Jakob Disease, Frontemporal Dementia, Morbus Pick, AIDS Dementia Complex, Vascular Dementia, Progressive Supranuclear Palsy, Corticobasal Degeneration, Multisystem-Atrophy, Hallervorden Spatz Disease, Huntington's disease, Stroke, Traumatic Brain and spinal cord Injury, Retinitis Pigmentosa, Macular Degeneration, Glaucoma, Cochlea Degeneration, Depression, Schizophrenia, Multiple Sclerosis, and developmental neurodegeneration.

4 Claims, 5 Drawing Sheets

OTHER PUBLICATIONS

Patricia Lagadec et al., "Evidence for Control of Nitric Oxide Synthesis by Intracellular Transforming Growth Factor- β1 in Tumor Cells" American Journal of Pathology, vol. 154, No. 6, Jun. 1999, pp. 1867-1876.

* cited by examiner

A)

B)

A)

B)

SEQUENCE LISTING

```
<160> NUMBER OF SEQ ID NOS: 163

<210> SEQ ID NO 1
<211> LENGTH: 89014
<212> TYPE: DNA
<213> ORGANISM: Homo sapiens

<400> SEQUENCE: 1
cagccacact gtctttaact ctcagcccac ccacactgag gagggtgcct agaggttcta      60
tttccaaacc tttgcatgta tcttaaaaat ctcaataaaa tgagaccttc caccatccaa     120
acagagctga tattctcact accagtccct ctctaatatt cctatttggc tgaaaataag     180
tagcttcaaa aagttttaaa aaagagatta cttgcagcat taacacttct ttgttgatta     240
acaagtttcc tatggagttt taaagctcat actttgttct tgtccttgtg gacacaaatt     300
ttctaactgc aaatgggacc tttgtgtccc acattcaaat cctctctagt aatttctgca     360
aaggttgaga aggctggcat gatggagaga acggtaacca tgaggaaagc ttcttggagt     420
aaagcactcc tctctccaat gcagagggta aaactattaa catataagca aaagaaactt     480
gggctaactg agacccttaa aggagttccc ctttagtcca ataaaaggcc aacttcaaat     540
cttaacacca gataaggtag tcaaaatcat attatatacc cagagaatga ctgcttgaat     600
ggacatttct tacaagggac cttggttagg tgcagattta attcctagac tggggtccag     660
gtaggcagtg gaaagagcta atgtttacag tgagaagtga ggcagctttg taagtgtctc     720
cacaccttca cattttgtga acgtggactg gagataactg aaaaccatct gctatcctta     780
cctggggatc cagattttcc tgcaaaatct ccaaatattt ataaagtggc ttcactttt      840 gaaacgctgt gctgaccaaa caaaacatat gtttagagtg cctgaggtca tagtcctgac     900
aatgatagta ttgtgtagtt gaaatcctct tcatcaggcc aaactgtgct tgagcaatca     960
```

```
ggagcccaga aagatggaac ccattggtgt tgtatagaa aactagaaaa tcaagtcaag    1020
tgtaatgaaa aagtaaacac gataaagcct agagtgagaa tttgctcctt tttagaaaag    1080
gatgaaggct gggagcagag aatagtaaca taagtgcagg ggaaagatga aaaaagaac    1140 aattttcat tagtagatgg tggggcaatc gcatggatgg ggacatctgt tctgattttt    1200
ctgcaaccca tgaaggtaaa aagtgggtt caaaacattc aaggtattaa agatggggta    1260
gagtttctaa actaggttga gggagagttt ctaaactagc cccccagatt tggggcttgg    1320
agcttaaatg aaaagtccag gagaaataag ggcacacagg aaccccggga acactggtcc    1380
tcaaacagtg ccactgtact tagttccatg gccagaagag aagtgctagg cagggaatga    1440
ttattttgca aaagcaagtg caatgtggtc atagctggct gtgagacatg gagcctcttt    1500
cctcatgcaa agttcactgt tttacagtca gagaaccact gcatgtgtga ttgtcaaatg    1560
ctaatgctgt catgggtccc ttccttctct gcttggttct ggagttctcc aataaaacca    1620
atttcctggg aatatttgat gttttccctt gtctcttttc aaggtatggc tatatatata    1680
gagctataga catatataga tatatatata tatatataaa acatagctat tcatatttat    1740
atacaggcat taataaagtg caaatgttat tggctattgt aaaaatcaat ctcatttcct    1800
gaggaagtgc taacacagct tatcctatga caatgtcaaa ggcatagaat gctctatgtc    1860
acccactccc tgctgctgtt gtttctgctt atccccacag cttacaggga ggggagtgac    1920 cccctttggtt ttccaggaag catcagttca ggggcagctt cctgctgcct ctgttctttg    1980
gtgagagggg cagcctcttt ggacatggcc cagcctgccc cagaagagct atttggtagt    2040
gtttagggag ccgtcttcag gaatcttctc ctccgagcag ctcctccccg agagcctgtc    2100
cagatgctcc agctcactga agcgttctgc cacacactgg gctgtgagac gggcctctgg    2160
gtcgtggtcc cagcactcag tcaacgtctc acacaccatc tggatgccct gtagcgggaa    2220
agagatccaa agggcaccat gagttggtgg gctccgcgga aggcaaggtg gcctgctgac    2280
cttgttgcta tagtgagtgc aagcagggtc caaaagtgcc tgtgcattta acatgtgctg    2340
actgagtgcc tgctgctgca ggccagccag ttccatgtgg aaagggtggt gggggggtttg    2400 tgctggtggc agctgtgctc aaaacctacc atacttttg gctctggtgc tatctgatca    2460
caataggtcc tgacagcaca atgatcctct gctgggcttc tggggtacac taacactccc    2520
aacacctgaa aattccccat gtagtggccc ttaatatcat ttcaacacct ttctatttag    2580
agaagttctc gcttcacagc aaaattgagt ggaaagtaca gagagttttc acaaaacccc    2640
ttccccataa aggcacagcc ttctccacct tgacatcatg catgcatcta tgaggtacat    2700
ttgttataac tgatgaacta acactgacgt atcattatca atcaaattca tagtttacat    2760
tagggttcac tcttggtgtt gtatattcca ggggttttga caaatgtata atgacatgta    2820
tctaccatta tagtatcatg cggaatagtt tctctgcccc tcaaattccc tgcattccac    2880
ttattcatcc ctccctccat tccoctaaat ttctggcagc cactgatttt gtactgtctc    2940
tgtagttttt gcctttcca gagtgtcata tagttgggtc atatacactg ttctatttta    3000
acagggctga ttaccccgt cagaattgta tgcaggcatt agcatggttt catttctat    3060 aggccacaca ttttgtagag tgattcagta gcagcttcta cgagctgcca aggatgacct    3120
ctgggatgct ccattcctct ccaacaacat gggttgaac cctgtgaaac agctgcctat    3180
gtgggtcagg catgcttaac tctatgccat ttcctagggt tcaccctaac cgaatcaagc    3240
tcccatccaa ggagaccatc caggagatcc tgcccaggaa ggtggcaaga gttttctctc    3300
actggcttaa ttttatttt gcattgcaaa tattttttgtt atcatttcaa atccttttg    3360
```

```
gaaataaagc aggcaggagt taagtaaatg gtctgatagg tggaaataga gtgtgctcct   3420
cccaattgta agatcaacat tgctaatggg atccctcaca caggtggctg ggagtgggat   3480
ggataaatct caaaactacc tgggagagct ggcactttt ctacttgttt tctaatacca    3540
acaactttcc aaacacacct aggagcctat ctctccctcc ccacccgatg agttcatgat   3600
gttaaattaa ttgcataatt cacctaattg acagtattga cagatggccc tgttaagagt   3660
agagtgctat tgttggtaca caagtaacat ttattttatt ctggcactgt aattacaggc   3720
agtaaattaa attaaatatt aagcattaac ttgaaatcaa tagggcaaca aatctcatta   3780
tgagaaaaaa tgtattatgc aaattctttt cagaatttta tcatcatgaa taatggcttc   3840
attacgagaa ctatacagca gaggaggcaa cagagtttga agaaacata acactccagc    3900 acattctgat ttcagaattt atgcaaaata ttcttacagt tttagtgtca aagaggattt   3960
gctcaaaact ccagagaagc ctgtgaccca ccacagcctg gttccccctc gccaacctcc   4020
tcggacttta ttaaggtctg tctgctgaag tggctctggg ccaggactgg cacagaccag   4080
acttcctgct ccatttgtct tcccgattgt gcctgatttg ttgtttctgt ttcttatctg   4140
aatttgcctt gcccttaggg aaaccaacaa cttagcctcg gccttcatgg ttgagggaat   4200
tcatccaaaa gaggcaataa aaggttttag tcagtagaaa gaacagtctt ctcagtgaga   4260
tagggccaca ctgttctctc tcattcttca ctaagggctc cttcctgggt gtgtcagaca   4320
tatagctggt tctgactcac tcacaaccta tcgttttctt ttttctctga ccattgccct   4380
catcaaagtg cccccaaaca aacaatttgg atcagcctct ttatgagtcc agaatgactg   4440
ccctgctatg gacagcctta gctagcattt cttaacaagg aaaataaga ggccattagg    4500 atgttcccaa cagacagatt tctcgttcct tccagggcat tctcctcttc tttgctttcc   4560
ttaattccag agtgaggagt cggtctcctc tttcccacgc gtgctcactc aggcctctcc   4620
caagtctgtg agcacagcct gcaaacacct gtacacagcc ttctgcatgc cacagtcact   4680
tctcactaca gctgcctgac aaaccctgct tgttttgcat ctgctaagta tttccttatg   4740
gagctgaaga ttcccagaag aaaacatttg gaatccagag ggaatcaaat ataaactcct   4800
gacgtgaagg cccaggagta agtagcagag gctgcaaaca aaatgtttta acccaggacc   4860 aaggggggctt ggaaaatgtg gcaaatgtcc tccgaatggc tatttgtgaa ctctcagagt  4920
acatatcagc tggttggagc ctataataat tgggttatcc actgtattga aatttgcttt   4980
ataaacaaaa tttaacaggg ccatagaaca caatgggacc ttccctcaga tttaagctca   5040
atattccaga attctctgcc acctaagagg caacttggtt gaatcttact gacctttgta   5100
aacactcact ccttacctgg tggttgagcc agaagctggg aatttctggt cgccctcgat   5160
ctctcaacac gttgtccttc atgctttcga cacagggtg ctcccgcacc ttggaaccaa    5220
atggaggctc ataatctttt acttctgtga agaaagccag caaacacagg gtcactgaga   5280
atggcatgtg cagccaaagg aaatgagcat ggtgagatgc ctggctgggg agcatgaagc   5340
actaagtaac aaatacatac gtaattactc taagagcaaa ttttaataat aatggctaag   5400
ataagaagga aggagtggtt ggggaagggc tagagaagta ttcaataaat gattgttgag   5460
tacttaaaat gtgctaggtg ttatgctggg ggacacagtg gacaacaaga tagagagggt   5520
cacggagctt aggttttaac acaggcattt tctacagggg gatattgcag caaaagggtg   5580
aaactggttc ttgggaagtg gaaaaatctt atgtattaca atggtttgtg agcctccaaa   5640
ggcccagagt atacaaagag atttaaaatg tggtattaaa tttcatgtag gtattgaggc   5700
ataaaaagga atgaaactct ggcacatgct acaacatgga tgaatcttga agacattatg   5760
```

```
ctaagtgaaa taagccagac acaaaaggac aaatattgta tcattccact tgtatgaagt      5820
accttgtaca ggtatattca gagacagtat aatggtggtt gtccagggggg caacctggga     5880 ggaaagggta ggaaaagtta tcctttaagg ggtaaagaat ttcagttgag caaatttcag      5940
tacagaaaaa tgaataatgg tgatggttgt agagcactgc gaaggtactt aatgccagta      6000
aactgtacac ttaaaaatgg ttaagatggt acattttata ttatgcctat tttgctacag      6060
aaaaacatca tggagagtag tgtttagaaa aaagttgtc tacaggccag gtgctgtggc       6120
tcatgtgtgt aatcccagca ctttaggagg ctgaaggagg atatcttgac tccgggagtt      6180
tgagaccaac ctgggcaaca tagcgagatc ctctatctat acaaataaaa aacaaaaca      6240 agcaaacaaa aaaagttgtt taaaaaggct ccttacgata tcactgattt taaaaaggt      6300 tgagaaatgc tgttttagtg ggaagacaga ggggacagat taacaacatc aacaaaattt      6360
taaaacgata attttcctct gatggtatat tcaataaaga aaatgataaa ggaggaggta      6420
acccttcacc ggggcctcag gcttaacta aggtcaaatt ctttataaaa acttccttga      6480
acatccttag ggtcaatctt ggttagatat cctgggcagg gctctattcg tgcatatacc      6540
atattttatt taatatattc acctgcttat ttttctcacc taactggact gtgagcattt      6600
gggtgcaagt tgagtcccctt tctcattctt gtattcttgg tgccaattgc aagggtctcc     6660
catgccaaca ggctgtcaac aaatgctttg ttgagtgagt gaatgaatga atgaatgaat      6720
gaatcttaga ttctctccaa agtggcagtg cataaactct ggccaaacat taaaacaaaa      6780 caccaatttta aatgagcaga ttaatatagt gtaaacagag cacaggacac ttaaaaagat     6840
agaaaacatc ccagtactaa aacatgcctg ggctgaaagg agagattggg ctggattcaa      6900
cactgttctc caaagtaagt aggatctttg gcctttagct tcaaaataat cttatttaat     6960
gagtaaaact ttcaatacat ttgcacttct aggtaacgaa ttgaagaagc tttcatggca      7020
agatgacatt ttgaaaaggg acggcttgtt tttgttcttt gttcatttgc ttttttcccc     7080
ttttccagaa ctctacttga atatttatct ttttcagctt caccaaatag tagagctgcc      7140
aggatatttt ctttttttata gttttaaata caggggaatt tgggatgaag gcctcccatc     7200
acattaagac aaaccacaaa ctatcctcct gtgtgtcatg cttttttgcct caaaggaccc    7260 aagcatttaa tccacattgc tcttgggtga gatctgaatt gtgatttgca tagcatttat     7320
actcttattt ttttctttca ttccttatct tcaaccagac tgtaaatgcc taaggcacaa     7380
ggcagtggct gaatttggtg tcttttcactt atctgctcag tgcctaaaat cgtgccttat    7440
acgtagtaag aatttaataa atatgagttc ggttgaattc aagcaaaaga gaaaactgag     7500
aatcagatct ggttcccagt aagtgtttac tctcatgtac ttcttctctt ctataaaatg     7560
aatatactga actgagctac ctccatgttc ctcttcagat ttatcttgta atccaatcta     7620
atcaaatatg atgcccccctt ggtaccatac cttgagatat atgtactacc atataatagt    7680
aaaggatagg atttgtatat gatataaatt gttccttaga taaggtacag tccacagacc     7740
ttccatcttc aattgttttg gcttatgtag cagctgcagt tggtgcctgc caaggtcccc     7800
ttgaccaagc tagggccagc agcctacagc tgccacaggt gttggctcat aagggctcac     7860
accttcaccc tttctgggg gattgtcctt ggccaatggg agttgcctat cctagagatt      7920
cgtggacatg accgccttac tctcagaggc agcgtatagc cgatgacaaa ttaatgttga      7980
agtttaacag tccaattctc ttggctcttg gtgggtaact atggtgcaat tcacactctc     8040
cagagcttcc agtgagatca agctgaggtt agacctctct tgaaatacaa gttcacttaa      8100
ctccttccat gcctcttcct gcttctctta cttccttctc atgagagctt atcctcaata     8160
```

```
aatcattgca caaaagtgtg tcagactcca cttctagtaa agctggccca acacagccgc   8220
caaggaagtg ctttctcctc tctccctagg cctttgtctc agtgaatctg cacaatctga   8280
ctgtagctgc aaagctaccc tggggaagcc ttgatgtagc cccttcttgt gaaggtgaaa   8340
ttactaaacc aggaagaaca ttctgaatct cacattgtat taccgttact ctgatgaaac   8400
tcctttacct ttctagaaag ctttcatgct ttttcctttc taccaagcat ttcagagagt   8460
tctttctcct ctgactatca acaacaatcc ctatactcat ggtcagaagt gacagaggag   8520
gacatgacca acatcagagg aggaaaatgt tgggatcaga ataaacccca gctgtcaatc   8580
tcatggctga tagtccttga gaacaaagac aaagtctttg tccttgagac tataaacgca   8640
gagccaattc attccaagtc ctaatcttcc tagttacaaa cactacacaa tttattgtaa   8700
ttttttttat aggtactctg tggatcaaag caagtttcca tggggaatga gagaagatgg   8760
cattgggcat attttactt aaagaaaaat taatgaatgc tattttagaa aggaagacaa   8820
aggcaataat cccttcccaa aacaaacaga cttataaata ggttacttcc tacttttcct   8880
aaaatcttgg aaagttgtga actccctaa tattcccaag ggatacaagg cctgcttccc   8940
atcttcgact tatgggtaat ttcacaagga agggaggtca cgggtagtct gaaaggtgct   9000
ggcaaaagga ctggctcctt gtgccccact gggagaattt atgactcttc tgcctcctcc   9060
taagcttaaa atagacaagt ctggggaggg aggatcatca tttgacctaa actgtcatac   9120
tctaatcctt taatattagt ttttcagatt aggagtacgg atgggatct gcagtgtgtg   9180 catgatttag gctgaccttt ctttaacttc tgaaaaatgt cctatttatg taacatagat   9240
tttccaaaac agctaaatgc atgtttgctt ttttctttct aattatggat ttttgcaatt   9300
cttctttctt tacccttctc tctcattttg gacatcctac tcccaacctc catttttttt   9360
tttctcatgc cctgcaatgt gtaggaagat ggtttaatgt ttggcagtgt gtatacatgt   9420
gcctctcagt taacatcttt gatattcaat tgcagcgatc aggcaacatt gctcattttt   9480
cctactatgg ccattaaggc aatgccattc tcagggcctc cattaggact tgtaggatga   9540
ccatgtaaca tggaggccag tccctcctgg agggcatttc ttaattgctc ctcagttcta   9600
agtgtccctc agaatgcctc agatatttgc tttgactcag cagaagaagg gaagatcgtg   9660
gccagagata gcctgaaccc tgcgagagga ggttagaaag cagaaagccc tctgccagcc   9720
aggtgggtac caatggtcgt tcctaggatg agacctcatg taacagagcc caggcagtcc   9780
tggggaactg gacagagctg gtgattggca acaagttgat ggcctgagac ctttgacact   9840
cccaactttt tccccagggt ttcaggcagc tggagactgg gatgtttaat ccactttggc   9900
aaaatctttg ggtccaaact gtgtatctta tttattttc atgatggtgc ttaaaatatt   9960
tttattttgg aaaatgcatg tgattaaaac tatgaaatga ctaaacaaat atgtataaag  10020
aaatgtaaat ctctccccaa ctcctaacca ctgtttctttt cacaaaagtg gcttaggtgg  10080
aatagtgaga ttaaaagtga ttaaaatttt tcccttatta cttgcaaatg agcacttctc  10140
aatcaatttt ttataaaagc ccagatgttt tgccctcaat tcattgggaa taaaggcttt  10200
ggtaaaatac agtagaaatg aattacaaga aaaatgaatc ccacttgagt gttgtggcaa  10260
catcaaactg ctattaaagg cacaaaacac atcttggttt ctgtccttat attgcaaatc  10320
tgtaacagag agtttgagga ccagcacctg ccaaagacca cacttggagc aacattgccc  10380
taaatgcttc ttaaggaatg tgagatgcat tttgacacag gaaaaagag cacaagttat  10440 taaacatatt ttagggtttt caaatgagtc agacaaagaa tattgaaaag gtcttcagag  10500
acgggatcca acatcctcat tttacagttg agaaaactga ggcccaaata gtacactgga  10560
```

```
ttccaggaag agcatttaga attgtgcact ttattactgt tactctgaag aaatttgcct   10620
ttgccttttt aggaagcttt catgcttgct catctctgcc aagcattgca gagatttctc   10680
ccctaaccag agcaagtaca gctggggcag tccctggtat gaacatgccc ttcccaaatg   10740
tgacaagtgt gtccctccct gccttgatgg ggccctcctc agcatacaac cttgagaagg   10800
ggaaccttat gggatctgct gggtggttgt tatttgtaat ttctaagcca gctatgcaaa   10860
aaaacaatta caaagagcag ccctctcctt agctggtatt atttacccac attaaaccca   10920
aacacttgtc ctttctgggt ttagggaagt agatgtgact ggtggtggag gtgaggtaag   10980
gatgagaatc tcattttagc tacaggcatc agattggggc atagttggca atagaattaa   11040
tgcagttcct ctttgcacat ttgatcaaat gatgcttgac cttgggcctc tctcttgtga   11100
agaactgcat aaaaagcaag ttcaggagtg tgtgggctga gtccagagaa aatgttacac   11160
ctggctaacc tataacaaga accacctttt taaaaaaaat tggaattgcc tctaagagaa   11220
aaagcgaagg cttagagagt atgactgagt ttagcacttc aaaagtggaa gagctaacaa   11280
tatgcattgt aagtattatt tgttgttttt gccctgactc cttaaaaag tagatatgag    11340
gacttagaaa agagatgcca agagtttgtg cctcacttcc tatatccaca aaataagaat   11400
agtcacatat gcccccctaca attattcagt gtgatgctgc agggccagct gcaccgccac   11460
ctcccaaccc cattgcactg gctcttccgg ttaggctggc ccaactccag gaggaacagg    11520
cagaagggct ggagtgaacc ctcccagctc ggcctggagc agccctccag caaactgatg   11580
ggaattggaa agataaaaca cccagcttcc tttgagtcag gtggtatgac actgaggtgt   11640
gtgttctgct cgtagttata ctccagttgc ccatggtggt aacccacttg ataagatatc   11700
ctttactggt ttccttccct ttcctgactc atttcctcat tctcttactg gcatttcctg   11760
caatctcttc ccaaataaac tactagtact caaattcttg ttccagggtt ggaggcactc   11820
cacccaagac atatgcctac acagcagaat tagttcatca aaccaagtct ttgtctcacc   11880
ctcagactgt ttctgaagcc agacagacgg ggctgaacac ctcagaattt ccctgagtgc   11940
ctcaaacggc atcttttcta aaaaacctct ttatttcact gcttgagaac gactttctct   12000
tacttccatc tccctcccgc cacctctctc tgcagtcttt tcactgatgg aagccacccg   12060
caaccgcccg gccctcgcag cttctttta tttgtctcaa aaggctctta agagaaaact   12120
acgcttgcct gtctcttccc agttccacaa ccctcagagg gcaggtctct gggacagcaa   12180
tggtattcct cggaaagtca gcatctggtg cacagctgct gttttgactg tagtcccaat   12240
gtaacagggc agcaaagttg ttgatggttt tccccaaagc agtaccccg agttttcata    12300
tctgctttcc agactgtgct cccttgaaat ccaggaaaat gaagcgtttc aatcctggtc   12360
tctcctcagc cgtctctcca acgcctcctt ttttctgtc tctttcttcc cccagcccct    12420
tccctttctt tttggttcat ttgcactttt ttttttttt tttttttcat ctcacaaggc    12480
tgcagcaact tgacaataca ctaaggagcc cttcttggag ttgtgttgct cctcattaaa   12540
tacttgttca gctggctgct acgtgtcagc ttctattcaa aggcctaaat gctagggatg   12600
tggaagtcag tgtgcttgca ggccagtttg gctgggatg acgagagtat tttgcctgct   12660
gtgttcacca agggggccc tgaacaggac cgccttcacc cgccttcacc cgccttccac    12720
acaacacaca aacacttgta tgaacaccaa acagactgaa agcctgggac agagatttct   12780
ttgtaaaaga gaagccatct ccagttctgt ccttgctgaa tggcgatttc atgaagcttt   12840
ttctcctttt tcgtagaaca gtaacacacc aatcacctcc tcttgtcctg ttcttacttc   12900
aaacaattct gaaagatttg tttttctttt tttttctttt gtattctttc agaggattaa   12960
```

```
aatgtctgaa atgacagcct ctttcattat ctatccccca agtctatttt tctttctaaa   13020
atcatcccac ccaccccacc caactccaac attatattac ataatctctt tgttcattac   13080
ctgtccctaa aatactggct cttcactaga cttcctgtct ctcaaagaaa gacactgctt   13140
tttaaactgc tgtatccctg gcattttaaa caatgcctgc gacacaatag gtactcaata   13200
aatacttttt gagtgaatga atgaataaat atatctttag ggaaataaag ataaaacagt   13260
tatctcaaat tttaaggtat caatactgtg acctgctaca caaattaaca gccttggatt   13320
ctgttaacag ggattcaccc agagaagtga ggccatcact gaatgttcct caaacatgtg   13380
attgtctcct cagcttctgc tggaaggctt catatctact gccaggatgc acagagtagc   13440
tctgactatc gtatccatac tgatcatagg aatcatagct actatttttt ttgggggcg   13500 gggggatgg agtctcgctc tgtcgcccag gctagagtgc agtggcacga tctcagctca   13560
ctgcaacctc cgcctcccgg gttcaagcaa ttctctgcct cagcctcttg agtagctgcg   13620
attacaggca cccgccacca tgcctggcta atatttttaat ttttagtaga gatggcattt   13680
caccatcttg gccaggctgg tcttaaactc ctgacctcat gatctgcctt cctcagcatc   13740
ccaaagtgct gggattacag gcgtgagcct gtacctgtac atggccatag ctactatttt   13800
aaatacgttc tccattggcc aggctagcag tataccagga atactaaggc ctgtgagcta   13860
cagagtcaga caacagggct ttgattcctg gctccacaac tttcgcactt cctgagcctt   13920
cagttctctt attgtaaaat gggattaata acagtacagg cctcaaagag ttttggtaga   13980
ttaaatgagt tgatgtgtgg agcaagtgct taagaagtgg taattattcc tttatggctt   14040
tctttatctg gaccaaatgt actttcaata agaagccttt ctctctgacc actctcttca   14100
cctaactgca acacatctcc cgaggcccct ggtggaattt tgtgcgaaat gaagctgtac   14160
cacctggctt ttgaagagct ctattatcat ctgtttatgt tttctcacct gataaaagtg   14220
aggcttctcc agtgtagtgc tgttctttct ctgttttccc tgtgctcccc tgcattcagg   14280
ggagactggc tagtaaagaa gtaactcaga aggatgcccc agagtcttcc tcttccttta   14340
agagctgacc taagtctcat tccctgacca taacactgca ctccctgtag ccaacctggg   14400
cattcagtcc tttgagctca ctgccttccc ttcctaagca tttatcacaa ctgaaccaca   14460
cttgcctgtt aaaaacagac tagttaagtg ttccagtgcc agtaaatagc atgagacaaa   14520
gcctggaggt aagacctaaa agacatccat catgatgaag tgatgaacac agaatgagaa   14580
tgtggcgtgg aggtgagctt ggagccttaa tatccatgtt tatgagtcac ttaaaggcag   14640
gctaggtggg acttcacagt tttctgtgaa atcttctgtc cctaatcctt gtatcctact   14700
tcattcagtt agaccttctg ctgcttagaa catttttctt caagtagtga gtactgtaat   14760
gttaacatcc aagaaagtaa aacaaatagt cacctctgca atagctcatt aacaactggg   14820
aacagagagg ttaatgttcc atagcttaaa aaagtatcaa tacaactagg gactctctca   14880
gtacaggatg gggtgctata tccatattac caatggcagt catcccgaga aatccaagca   14940
gccacactta ctctccttca gtgggtagat ccactatact tgtcatgtag attagctgtt   15000
ttcactggag acttgcatcc catcatcctt ctgcacacag ttgaggtgga ccatacctct   15060 ttttttttt tttttttttt tagacgcagt cttgctctgt cgcccaggct ggagaacagt   15120
ggcatgatct tggctcactg caagctctgc ctcccgggtt caccattc tctgcctca   15180 gcctcctgag tagctgggac tacaggcgcc tgctgccacg cccggctaat ttttttgtat   15240
ttttagtaga cgggggttt caccatgtta gccaggatgg tctcgatctc ctgacctcat   15300
gatccacccg cctcggcttc ccaaagtgtt gggattacag gcgtgagcca ccgcgcccgg   15360
```

```
caggaccata cctcttgagc aggcttctct gcaggtgctt ggtagctggc tcgatgggtc   15420
agatcataag cctttcatgt cacagaagtg gccctgatcc atgatcccac aagcacacag   15480
actcagagcc tacagagaag atgactctgg agatctggtt cccttactg tccatctatg    15540 attcatcata caaaggtaag cacattccac atttccttt ttgaaataag actgctgatt    15600
ttaaaaaaat ggtaattaca tctgctatac tgcaaactgc agaagttcaa gcttaaggaa   15660 agaccttta catccttccc tcttccttat accttaaaat taaagtctaa catcaaacag    15720
ggggattcat tatttaattt gtaagataag aaacatatct gcatgtgtaa gttttttaaa   15780
aagaagggag aggaaacaaa caactgtttc ctgtagacta caagcttctt gaggtcaaaa   15840
cctgtccttc catctgtgtt tctacaaaag ctacagcagg acaacatca agatgaatgc    15900 agttggaggg aatccatctg tcttcaggct tcgtgtactt tccaaaggac cttttgaatg   15960
taaaagaaaa gcctctgaaa ctaagactag gctgaaaatc tgtctttaag gttttttgaga  16020 catgccaaaa agaaacaaac aaaaaccact aatgctttta aagaagaag tcaaggtggg    16080 agaaggagct tactacgtga gttcacacgc ttaatcaagt gaacggcttt gtgtcaggac   16140
gaacgtgagg atggataaat aaccttggtg tctgcagccc agcaaagat gggagaaata    16200 ggactgtggg cttaagatca aacgaaatga gaactgggat ggcctcttc cggttcccca    16260 gggctgtctc ttcttatcct aaggttataa aaggttttt gagactagct gaataaacca    16320
tatcctgttc cttccttggg aaaacttgtt tatattctaa ctgtttttag accttgtaaa   16380
atttggtgaa ctccttcctc attagcttaa attcttccac actcagcaaa tatcaacagg   16440
caagggtttt agtcagtgat aacaatgaaa gctgggagct caccaggc cttaataagc      16500 tggctgcact gacagaggga aagacagaga cacaatctcc agctcatgtt tatagaataa   16560
cagagttgaa aggatagga atgatactga aatctaggta aatttattct gacagtgaca    16620
acagcattgt ctctgataca actcataccc ggctaaagat tcattttgga actgtcaaag   16680 cttcaagca taaaattatt ctcagtggct gaaacttggt taaacaaatt tcactgtgca    16740 aggaaaaca aagttaactt ttggaagtgt tttgggggaa gaaatctcag tcaagaaact    16800
agataataat aactatgtca gctagatagg aagtgccatc cccatgcggg ggtctcagga   16860
aaacatgtga ggttcagcag ggtgcaggat gggaggggt gacccggacc cacgctggag    16920
aattggctat gcatattctg aacaggatga agaatcagag ccagcagtgg tgccaactga   16980
atctgccttg ggcaaaatgt tgggtagttt ggaccagtga cccaagctgt ggcaacctga   17040
gcaacaaaat aaataatgac aatactggat actcatataa tgaaacaaat ccccaaatc    17100 ccctgctgat ataaatacat aattagtaaa caaagaacag gggatggtgt cagaagagac   17160
agatcttttt taaggagaa tgcatattaa taaatataga aggaacaaga aaacagaaa     17220 atcttcctta agtaaacatt atagtaataa ttgttatagg caggaattag tcatagatca   17280
tcaaattagt gggtaaatga tgaataagaa agttctagta cctttgctaa acaggtattt   17340
agtatcttta gaaacaggtc aaaggcatgt attacttaca aatggacaaa tagcagcagg   17400 tcccactta accaaaggac caaatttaac attaataacc agacacatgg acatcttatt     17460 cccctgata tgacgcactg aagataggca cactatcatt tctgtggtaa ttttgcccaa    17520
aatatgtaat ctcaatctaa tcatgagaaa acattagtga aacccaaagt gagagaccgt   17580
ctaaataact gtcttaaact ttttacaagt gtcaaggtca taaagacaa aaatcgactg    17640 aggaactctc acaaggtcaa ggagactaag gaggcatgca cattagatca atgcgggatc   17700
ctagactgga tcctgtttca gaaaagaaca ttactgggga cttggaagta caaatacgta   17760
```

```
tatggattaa ttaagaacac tgaatccagg ttaatttgct gtttttgata gccatactat   17820
ggtttaggtt agatattaac aacaggcaaa gttgagttaa gagtatacag aaactccact   17880
atttttacaa ctattttcta agtctaaaat tatcacaaaa caaaaagtta aacatggaat   17940
ggaggctggg tgcagtggct cacgcctgta atcccagcac tttgggaggc cgaggtgggc   18000
agatcatgag gtcaagagtt cgatatcagc ctgatcaaca cggtgtaacc ctgtctctac   18060
taaaaataca aatattagct gagcgtggtg gtgcatgtct gtaatctcag ctactcaaga   18120
ggctgagcta ggagaattgc ttgaacccgg gaggcagagg ttgcagtcag ccgagattgc   18180
gccattgcac tccagcctgg gtgacagagc gagactgtct caaaaaaaaa aaagggtgg   18240
agttagtttg gcttcatttg gcagccaacc aggatgaact tgggtgcaca gatttctcag   18300
gtgagaccta agaccctgtc tcacctaaga ataagaagg acatgaatag aaacacatag   18360
tggacaggag acagcgaaag gcagttctag ttcaatgaga gcttgcgttg ggctgctttc   18420
attggacaag catgccagaa ttctattgct ttatgtgtca tgcatctgtc ctccaaggta   18480
ctgagaagag agtcaggaaa gggtatagta atgtagacct caactgttct tgccttctgg   18540
acaacaaggg ataatacttc ctagaacaat agcctcaccc tggcacccca gatgtttgtt   18600
gcccattcta tctacagtct catggtcaat agtagtaaca gcctctaaca gtgaaaagga   18660
ctcagcatac aactgcagag aagacatagc agagggcacc tgggaggcta tgacagtgtg   18720
ttcagggaaa aatgatccta aagaaaaaa aaaacagtag gtggctgaac ttggggataa   18780
aaagagcaag ccagctttc aggagaaaag taggtctcct aatcagtctt gcaggcttaa   18840
gcagtaagaa gacggccttc ctcaataacc tcttcactag aattttcaaa acctaaacaa   18900
atatctcaaa caatgatttt tttttttgccc aataaaacaa tgtcatgtcc ataaaagtaa   18960
attttgaatc aaatcttttt cccagacata attctgaaaa atcttaaaac acaaagtaaa   19020
agaaatcaga tgcttatctg aatattaccc acatgatcat tagagataat tcttatacat   19080
ttattagtat tcgtctcttg ccagatattt aaataactgt gaagagatgt gtcaagagaa   19140
gagtaattat acaaaggttt ataaaaggag atacaaagct ttatgctcca aatgtggctt   19200
tcagtttaaa aacctaggct gtttagcata accccaaata gttctgggat ggttgtataa   19260
tatcagatct caactagctc taataactgc tttgtaaccc ctggaataat gctcgaagca   19320
acacatgatc ttattttgaa gacaagttta ccactacaca atgatgctgg tccacaccta   19380
cctcccactg cattacagcg agatgtcatt tcccagagca ccagagccat ggagtagaca   19440
tcggtctgct tgaaggactc aacattctcc aaattcatcc tggattctag gacttctgga   19500
gccatgtatc ttgcagttcc cacctatagc aaaaacagac agtgaggccc atcatttaat   19560
tccagctgcc ttttattttt cacaatatag ctgatggtgg ccctgacac gtgcagagga   19620
ttttttttaaa aaatcaaagt gctgttttaa agaatgagaa atgcacagaa aggtacagat   19680
agatggttat ttttaaaat agatgttctc tccctgaaaa ccctctaaag accataaaca   19740
aagcatgcca aaataaggaa gtgccaaacc ccagagctgc cttatctaac cccatgactt   19800
atgtcatcac attttcaat aacatcctta cagataacct gagagacaat atttgtgata   19860
ttttaaatgt ttattttgc tttccaaaat tgaattttt tttattcctg aaactccaag   19920
acttatggta aaaataataa ttgctatcag ttttgatcac tttaggactg agtcttaatc   19980
tttgtttatc ccatggcaca ttccagtgtg caaggatat agtacaattg cataacatct   20040
ctactaaatt aaattgtata aaagcatttt cacagtaaaa gaccaaatct ggatcacttt   20100
ataatttaa cttgtgggcc atgtagttt attttgactt ttaggcctgt gctaatctct   20160
```

```
atgactgata atatgcaaac gtcggatcca tatgaaaaag gaaaaaaata ttccagagaa   20220
tggctcactt aaatatttag tgttgtagta tgtataaact gactaaataa caataaagtc   20280
ctaccttccc aaggatctag ggaagccaag tgagttgata ttatcattcc aaggaatgtt   20340
tcttattggc atgtattaga gaatttttt cttctcaaga ggtcattgca tggctcatta    20400
ctctggcaca ttagtctgtc catatttcga tgtttacctc aacactgcgt gcgctgccat   20460
ggacacaggg ctgactgagc agtaaccgag tgcttcaaag tgtgtcctgc cacctggcta   20520
aagaagacag tgctgctctc catggactcc actgtgtgaa acactgggc tcatcattta    20580 taagggatgt tgtggtgatt tccaatcacc ttccaatagt ttcttagcca aaacatttc    20640 cattttaatc tgtgagagtg cttcaagagt ggaagtgctc actcagtcga caagtactta   20700
ttttactttc aatgttcaag gcattgtgct acatatcttg ggtgaccatg tggatgtaga   20760
tttggacttc agggagattg ccttccacga tgcttttaat acaaagaaac caacacaact   20820
acagctagta tagagcagaa aggactgagt acaaccataa gagagggaaa aaatagaggt   20880
aaagtactaa cagtgcttga aacaaagaaa aaacatttgc tggaagagaa atgaggattg   20940
atccaggagg aaaaaatgtg ctgaactggg aaggatttga agataggagg agaaatgctg   21000
tccattagca aaaatgctca ggcaggacag agcagagtat gctcaaggca gactccatac   21060
tttggctaga ttccctagac cagtgtccag agtacagggc tgtttgagat aagagccagg   21120
agatatggat caagaggtag ggtgaggcca ggctcaaggt aaagggggatc tagcactagc   21180 tctaacttac ctgcccactg ttagccaggt catccacaga cagagtaggg tccagacgca   21240
gggaaagccc aaagtcacac aggcagcagg ttaggtcgtt cttcacgagg atattggagc   21300
tcttgaggtc cctgtgcacg atgggcatct tgggcctccc acatggagtg tgatcactgt   21360
ggaggtgagc aatccccccgg gcgagggagc tgcccagctt gcgcaggtcc tcccagctga   21420
tgacatgccg cgtcaggtac tcctgtaggt tgcccttggc gtggaaggcg gtgatcagcc   21480
agtattgttt cccaactcc gtcttccgct cctcagccgt caggaactgg agtatgttct    21540
catgcttcag attgatgtct gagaagatgt ccttctctgt cttccaagag gcatactcct   21600
catagggaaa gatcttgact gccactgtct caaactgctc tgaagtgttc tgcttcagct   21660
tggccttata gacctcagca aagcgaccct tccccaccag ggtgtccagc tcaatgggca   21720
gcagctctgt gttgtggttg atgttgttgg cacacgtgga gctgatgtca gagcggtcat   21780
cttccaggat gatggcacag tgctcgctga actccatgag cttccgcgtc ttgccggttt   21840
cccaggttga actcagcttc tgctgccggt taacgcggta gcagtagaag atgatgatga   21900
cagatatggc aactcccagt ggtggcagga ggctgatgcc tgtcacttga aatatgacta   21960
gcaacaagtc aggattgctg gtgttatatt ctgatgggga aacaaaacaa ggagagaagg   22020
agttggatgt ggtaggtaag tactgtcagg aagtgggttc atgcctgagc atctatagat   22080
tttagcatct gcatagtttt tgtagatacg atattgttaa ttttatttc agggatgcaa    22140 gtgcatgctc gttcagcctt ccctgcctct ggccatctgt tcgtcatccc ctgctcttcc   22200
ttcaaacttc agcttaaatg tcactgctta agagaggcct agaaaaactt ggaaaactgt   22260
cttattttat acatttcat agcacccttat acttttccta ggtaacaatt cagtacaact   22320
taaactaaat gaactatgac tctacctctt gatttcacat ctgtctttcc ctactcttgc   22380
catcccccac ggacagggaa ctccatgctg gaaggtacca tgtcttcttc actactgtaa   22440
actgcactta gcacacagca ggtcctcaat attgccaaat aaaagacaa accatttact   22500 gagtgttatc taagctcagg acattgggaa catgaaaaaa aatgacacag cttctgcctt   22560
```

```
caaaaaatct gcatgtatga catctggtaa aaacacagag cgtgccacag tttgcaccaa   22620
aatctttgct cttttttcaaa ctccaacttg ttctgctctg atcagcattc aggctaccct   22680
gggcccatgg gtgacaggga gaggagtcca tggaaaggat ctctttggac agttatctta   22740
catccaccca acattcctct tttcagtgtg catacgaatt gtagtttcat ggaactgaaa   22800
tatttaatag caacaatgga aacatggccg caaaggtaaa acaagttaaa aatggaaatg   22860
ctgcagtttt ttgacttgga attctgaagc aggcccctgt gggctgacaa ggagagtcct   22920
tagcaccaga tatctaacta taatatcttg tgcctcaaac tttgtttcat gtgctggcct   22980
tgttggctct ggtgaaatag ttttcctttt tggaagaagg acatgaatag aaacagacag   23040
tggacaggag agagcaaaag gcagctctag ttcactggga gcttgtgctg gctgctttc    23100 attgggcaaa catgcagaat tctattgctt tatgtgtcat ccatctgccc tccaaagtac   23160
ccattaatga gcaggcctca tgctcagatc ctagaatcat tcattaaata tatcactact   23220
gagtgtctat gatgggcatg gcactgccct cagagagtac ccagtagagg acttagggca   23280
tatatacaag taagcaatat atggcatctg ggataggggc taaatgtaca atgtaatcta   23340
tatattagtg gaatgtggaa aagcttagag aaacatggaa ggcacagtag caaaaaactg   23400
cctttaagtt ggtctctgaa gaatgggaaa agtcagtgat gagtggaaag agtgctatgt   23460
taaggagaaa gaatatatga tctacttaag gaagagcaat tatcccatac tgaccactct   23520
gcacctgcgg aatagaaagg aaaaaaatgg gtaggtggta tggaaccaaa ctccgtgtca   23580
gaaaaggatc ttttgattat tcatttgtca gttttcacct acagtaggtg tttaaagaga   23640 aaaaaaaag tgatgagaat atagtccagg tagaatgagg atataaccaa attctctcaa    23700
ggggaaccca ttacctaaat gatactgata aaggagttaa aagaaatta cttgggcaga    23760 tagtaagggt atggaagtcc tcggtaaggt gtttcttttt aatgaaaagc agccccaaat   23820
cattttctaa caaagagcag cctgtaaagt tgagcttcag acatagacag gcaagctggg   23880
agcttgcacg ggtgaatgcc agcaggaact aaggacatgt tcaagatggc agctccatct   23940
tcccttctct ttgtcagcca tgtgtacaac aaagaacaga ccagatggtg ctgatcaact   24000
ggaaagccca tttgcataat aagattaggg tggggtgacc agtcttcccc atgcactatg   24060
taaacgtcat acctgattga accaatctgt gagccctatg taaatcagac accgcctctt   24120
caaacgggac tataaaatcc agcacattca ccactggccc gtccttttccg cttggagact   24180 cctttctcta cagagagaat tgtttctctt tctcttctct tctgcctatt aaacctccac   24240
tcctaaactc ctcatgtgtg ttcatatcct aaattttcct ggctcatgat gatgaacccc   24300
aggttatata ccccagtcta catagctact tcagcatctg atactttctt tttttttttct   24360 cgagatggag tcttgctctg ttacccaggc agcagtgcaa tggcacgatc tctgctcact   24420
gcaaccttgc ctcctgggtt caagccattc tcctgcctta gcctctatgc ccagcttttt   24480
tttttttttt tttttttttt tttttttgtat tttagtgga gacggggttt caccatgttg    24540
gccaggctgg tcttgaactc ctgaccttgt gatctgcccg ccttggcctc caaaagtgct    24600
gggattacag gcgtgagcca ctgcgcttgg cccagcatct gaaactttca tctaacgaaa   24660
cagtgagaaa tgaagctggt acatatccat ttttaaggtt tatgtgtaat atgattactt   24720
gttcttaagg taagtctgag tggaaatgcc aacttccact gactatatat tctagatgaa   24780 atcttgggt ctagtaacca gagaagtaac cccaagatat cagaattcca gcaaccaaga   24840
gggaaaaaaa aaatcaccat ttttttggaaa gatatatgaa tgcattttaa aagtataggg   24900
aaagtgagaa aatttggtga ttgatcctta aaaacataaa ttcttacact gggaggcttg   24960
```

```
gattgggaca aagaacaggc aagagtaggg cagaaatggg gtgggacaaa gcaattacag    25020
aatgattgaa tgcaaaagaa aaaaagatg ctcttgtgga gatgtatgga ctgtccctgt     25080
tgtacagcaa acaaaattaa gggggcagat gaacacaaca caaattcaaa cacaacagcc    25140
gatccagcag tcggcatttc cacttaggct taccacttcc acaatgctcc ctgcctgaaa    25200
ctccacctct attatatgtg gtatccaatg aatgtgtttg cttgaagtac ccacttgtct    25260
ccggtctctg tgtctgtaac tacatggaat gtcttataat cagaaatcca cttgattatc    25320
tgattgcttc tctcctgaca aagcagggta gtggccaggt ctgttttgat catcatgata    25380
tacacagcac ctggggcaga atggggcaat ttatggtatt caacaaacgt tgttttaga     25440 agctgaatga ttacttacgt ggaatgatac ttctcaaatt ttttatattt tacagcaagg    25500
tttgacaaac tatggctcag aagtccatgg cctgcttttg tatagtccta tgacctaaga    25560
atgatttcca tccccatttt taaagagttg tttaaaaaac aataaaacta agaggttcat    25620
gcaacagaga tcttatctgg cccagaaagc ctaaatatat tactatctgg cccttcacag    25680
aaaaactttg ctgaccctg ttctagaggt gttattttaa taacctcatt ggcagaatct     25740
ggagagactt cactttggcc aaatgtgaat atgtagtcaa ttttttttca catatgagaa    25800
atacaatttg aaaaaattta aatattaact gcataattac ttagctttgt ccttaattca    25860 ctaaacgtc cagatgaaat gttgattcat catggataat tttattttac aattcctaaa     25920
tatctataaa aacagtcgta tttgctaatt tcaattcctt tttagcctaa aggaaacaca    25980
aaaacagaaa tcccctttaag tttatgtgtg gcactgactg aagaagattc tagaaatccc    26040
cagttcaatg tcagaaacca agttttact ttctcctaaa atttcctgtt atttctttag     26100
aagacttaca cttaaaaaat ttgaggggga ggaattcttg aataacatct gtcaatcttg    26160
aaacttcaaa gaggtggtga aaaactctaa caatagcaac cagggctgga aggaagcttt    26220
gggatgtggc tttatctaaa caggagccac ccacaccctc tggcagtatt aacccttggg    26280
ttgctactag aaaacccaac agctgttggt gtaggtacaa gccagcatct cctttagtcg    26340
aagaccaaca ggaaatgctt cttttcatca gccgccagtt acagagaaac tcataaactg    26400
aacacttact aagttcctgg ctgtgtgcta aggattttat agaatattta aatttaattg    26460
atagaaaaac cctatgaggt agaaactgct attattataa accccatttt acagataggg    26520
aagctaaaga tcagacagtt taagtaattt tcccagatga taaatttagg caacagcaaa    26580
gctggtattt acaatgagca ttgcctgatt ggagagactt ctgatctcaa ccccatacct    26640
gatctctaaa cttcatattg gtgagagcca actaagaatg gcaatgacct taggctgggt    26700
gtggtggctc acacctgaaa tcctagcact ttggcgggag aatcacttga gcctaggagt    26760
ttgagactag cctgggcaac atagtgagac tgtctctaca caaacttaaa aaaaaaaaa    26820 attagccaga cactgtggtg cttcctgtag tcccagctat tacggtggct gaggcaggag    26880
gattacttta cttgaggcag gagttcaagg cggcagcaca ctatgatcct gccactgcat    26940
tccagcctgg gtaacagagc aagaccctgt gtttgtgcgg gcggggatgg gggggtaggg    27000
gttgcggggg aggggaagaa tgactttata taagctccca atttgataaa gtgttttct    27060 ttagtgtagc ctggactaag tgatttaca gccatccacc gactgacatt ggcaattctt     27120
gtataatgtg tctaaaggag tatattttgg gtatgggat tatattcctt tgttctgaac     27180
taagaaccac agtttagtag tgtctctgta aatatgcatc ttttttcctgc aggaaataa   27240 aaagttttat gtgaaggaga acccccaaat ctttttcttt tctcagagcc tattctcatg    27300
gcctagatct tagcagagct caaaacataa ttgttgcact attgggacct tccatgaata    27360
```

```
gtaataacat tgaaccagat atagctctga agggcattaa aaataagggt ggaatttatc    27420
caaggcccat aaaaaaatga ggctataata gtaaacattt ttagcctggg ttccataaat    27480
agagttcagt gggtctgtga atttgaatgg gcaaaaattg catcttttt tattttctct     27540 aacctttaat taaaaattaa tatttcctag tatcagctgt acctatgagt tgttgttgc     27600 agacgtctca gcatgtgact tacgctcacc atttagacat ttcaattgtt tagatctgct    27660
gctattgtta tttaaagcat tattatagaa acatatatta ctataacaca aattcatttt    27720
taaaatattt ggtcattgta tttcaatgta attggttttc tttgaaatac tccatgttct    27780
attttatgca tttaaaaaac atcacagtga aagggggtcc acaggcttcc ctacttcaag    27840
aagtccatgg cacagacaca caaaaaggga agctcccttg gcagagtgaa ggcatttggg    27900
ctctagtctc ttttccagga cttgctagag caggaatttt gagattgatg ggtttctcta    27960
ggaagttggt aactagtgcc aatgggagat ctgcctggct tgatttgttg tgctgcacat    28020
ggacaactgt ggatgctgtc ggagcttctg tggagtggga agggagctcc gcagtgtaga    28080
atttgaggag aagcccctcct ttgaaatctt gtaacaataa gaaagataac tcatatacga    28140
tgtgctttgt tgggttaggc accggacaat ttattttgta aacatgatct actttatttc    28200
tccaataacc ctatgtatga gttagattct cttaccccccg ttttacagag gaggatactg    28260
aaccttggtt gcttctacaa cattttttgtc tacttagtaa ataagtattc ttgttaagta    28320
aaagttgttc ctagtaagta ctcaataaat gaatgctgtc cttttaatgt tataattaac    28380
atgacttgag acaggaagtt cttccttccc ctcagctatc tctctttagc acagtttcct    28440
tctttggatc tcagccagtt gcatatatac tctcgcttta ggtgaacatg ctggcatgtg    28500
aacatccttg cggctagagc ttcactgcca acttcacaag aatctctctt ggcatctgag    28560
gctcattagt gcactaatac accaaggtgt gcgaaaaact gtcatccacg tcccttcta     28620 ttgctcggat aaattagtat cccactaaat gttcaccccta aactccttta ccgagtggag   28680
gaattgccaa actacttcaa atattaaagt aggagcctat ctcccaaatt cagctatgtt    28740
gatttgcttt ttatcaagac acattaactg atccacatag gattttattt accaagttgg    28800
ccttaattta atgcttttat tttttttaacc aagtgacttt tatttaaaat agtggattag    28860
ggaggttcag ttttaagttc cttttaggaa ctggtgtcgg cataacaaag gacataaaag    28920
aggctgagag caacgtgtgt gtgcgcgcac gcgcgtgtgc atgtgtgtgc gcacatgcat    28980
actcaagtta taagacaaat tgtttacttt tcaatcactc caaaggaaag tataccacag    29040
gatttcccct tgaggttttc tgccagtttg tattttttt tatggcatac taacatttat     29100
ctttggaaga cagaaaaaaa aagaatttga catttgtctt taaaaaaata tttatgtaac    29160
aagactctga catttgcaaa tggctcctta tttgcaacta agtctggcct ctatgagtga    29220
cagaagtgac tggaaatttt cagaattatt aaatggatct cacagttcat tgttaaggag    29280
atagcttggt ggtatggaaa gaacaaaagc tttgaagcca ctcagatgat taaaaaaaaa    29340 tgggggaag atatggtgcc tcacacctgt aatcccagca cttcgtgagg ctgaggtggg    29400
aggatcactt gagcccagga gtttgacacc agcctgggca atatattgag accctgtctg    29460
tataaaaaaa aaaaaaaatt agctggatgt ggtggtgtgg gcatgtaatc tgagctactt    29520
aaaaggctga ggcaggagga tcacgagccc agaagttcaa gactgcagtg agctataatg    29580
gtgccactgc atttttagcct gggcaacaga acgagaacat ctcccccctgc cccccccaact  29640 ccccccccca aaaagttag ccctctcttc ctctttcctt tctcctaagg gtatttaaaa    29700
taatatactt ggcccaagag cacagtatgg ccctcaaaac tagagaaatt actctgattt    29760
```

```
ctctcttgtg aaaaagaatt cattccaaaa taaaacacag atacagaaaa gtgcataaaa    29820
caagtgtctg gcttagtgaa ttactataag atcaacactc ttgtaaccac tggtcaggtc    29880
agaaaatata attttgctgg ccaccccaga agtctgttca tgttcccaa ctcaatcgga     29940 gatccctccc ttcctctaaa aagtaatcac tattcctggc ttttatagtt atcattttct    30000
tgagctttta aacttgtttt atcatccaag tatgcatctg tagtcgtctt gctactaata    30060
tgactgaata caaatggcaa accttgcttt tttgcagaat tactgtttta aaaaaacttc    30120
ctacaataaa aacaccagaa tctttaaaaa atgtttaatc tgaattaatc aaatcatcag    30180
acaaatctac aaagtgcctt tataaagtac atgaaatggt ctgacctatt caaatcaaag    30240
tcaatgtcat gaaaccaaa aaaacacact gtagaggcaa aacaatcaat tttaatgtgt     30300
tgtccttgac tggattccga atttaaacaa tagacccatt aaccttgaag aaatctgaat    30360
atggactgta ctgtatatat atttagatgt atatatgtga atgtatctgt gtcttagtat    30420
ctgtatacac acacacacac acagaaagag agtgaaagct aagcactcac atatatgctt    30480
catattgcag agttcaaaga tcttgccatc attttctgta cctttaaaaa ttttgttggc    30540
atgttacata aagaataact tgtcacctcg ttattctaag tgtgcccgca gaccagcagt    30600
catcagcatc ccctgggaac ttactggaaa tgcagagtct tagcgctgtc ctcaactaac    30660
tgaatcagaa tctacattta aaagttctct cagtgattca tttacacatt caagtttcag    30720
aggtaaattt tattcttgct aaacagttta gcaaaataa agttaagttc tttggtactc     30780
tgccatagag atgcttttcct cctacaaaa atttcttagt ggaattgttt gcaaagctct    30840
ggtacagctg tattcagcac tagccaatga gaaaatggcc catgataatt ttctagtcaa    30900
ttaactggtg gaggagtgta gaatgagata tgcttcccca tccatcatcc tagtaaaaag    30960
cacaccaatt taggcaaaca ataaaaagtc atttcaatta aacaacaaaa ggacagtaag    31020
ctcactagca atgaaggatt taatttaact tctagctatt gatagcactg tttgacattc    31080
tggatatatt ttgagagtat ttttcctca aatgatgaaa gaagtcttct ctccaatcaa     31140
tgtggttgtt ttattccaac tgcacatatt tcagaacaaa gctattcgcc acctctccta    31200
tcccatggca cagtctcctt tgtattattt ccttcttatc tctctcccag atggaaaagc    31260
cttgcatgta ttctaatcca gtatgataat ctctttctag aatacccatg agaggtagag    31320
gtgaaacctc tgcctgaaaa tgttatggta gaaggacatc attcctttgt tatcattcca    31380
taatcaaatc acaatatttc taactgcaga tatattggga taaagtctaa atattgggat    31440
atgtttaaaa ttattcttta cattaagtca aatgtagcct ctgtgtgctt ctattattgg    31500
tccttctgct gttctctaaa gcaaaaagta acaaaatgaa tccgttttct atgggatgag    31560
aactattaaa ctcctgctgg atatgaaact cacaacccct agatcatttc attttcaggt    31620
tgaacagcca tgttttcctc ggttacttt caagagatac attgatgaga ctctaaagtc     31680
tgacagattt atcagaccct aaaatcagcc tgcccagcat atagcgccca ataaatgcca    31740 ggacttttt tctaagggta aagtgatctg ttctctgaaa ccacgcttgc tatttaagat     31800
tcttcatcat gtgttttgat agacacagat ataaacttg gaatataact tgtgtagcaa     31860
agattacagc aggactctca cctcctcttc caccaagtgg agtttaaggc tcctgatggt    31920
ttgttctttc tgttttgttt tgattctttc agccagatca tcctgatttc aaaatgacct    31980
taactcacct ctaaaccctg gggtcttcat cacatgagca gattcccagc cagtgttttg    32040
acaagtgctc ctttgcaatc gattgtttga acctatatgt ctgattttac atctacctgt    32100
caagttttag aaaattggtc atttcaggcc attaaaaccc tgattcagcc tttgctcttt    32160
```

```
taggcatccc ttccactgtg cttttcaccc tttatgttcc tccttaggat atagattcct   32220
gctacttctc ttgctctgac tttaaaagga gggcaaccaa cattaggagg gtgcctacaa   32280
ggtaccaggc tttgtccagg aaatgatgac acatctgtcc tcccacaaag agagtttcac   32340
acctgatata tgttctttgg aacaagattt ttttcattt tcttttctgt gttattgcag    32400
ttttctgact actaaaagct taggttttgt taggatcccc acacctgccc tgattcttta   32460 attcttttc tggctggctg tctgaattac accttgtact ctgtctaggg gccctcatgt    32520
tctcaggaaa cctgaaagca aggtacattt cttaagttat ttcaggatgc tctccaacag   32580
ggagaccaga tcgctttgga aaagcatatt cattattcac aatacctgtt aggtcaccag   32640
aatacatcct ctctctctcc ctggctttcc aggtgaacca caggcttctg caattccttc   32700
ccacctgagt ttctcacctc ctaaaatcat gcacacagcc tccctggtcc ctgccttgtc   32760
tctgccaagg cagtagcacc caaaccttgc catccaacct tttggacaca ttaaggttta   32820
aaatgtgctt tcctttaacg tataatttaa tcagttttaa aagctaagat gcctattccc   32880
aatgaggccg ttgaccttgt tccaaagcaa ttgcttgtaa attgttgtag aaaacaaaat   32940
aatatcccct cttaaagtgt cttgctattc ctccaaggat ggggtaaaac aggtgttggt   33000
ttttctcctc ctctaacctt cgaaggcata attttggctc cttcctgtgg tagctgccat   33060
tctttaattg ttaccgtccc tttccaggct acagggggaa cgtgacgaaa aatataaaaa   33120
gatttggcag aacaaactgt cttgagtcca gtggttccca atgtgggctg catattaaaa   33180
tatcttgaag aattaaaaaa taattcctga taccaggccc cagaccaatt aagtcagaaa   33240
ctgcaggagt aagacccagt taatgagtag tttttaaagc tactcaggtg tttccaatgt   33300
gcagccaagc ctaagcataa ctacatcagc ctggtggaag aaacaggtat ttcgaatagg   33360
atggggcctg gaaatgaaa gacatgggaa taattttaat gactacattt cagagaaatt    33420
gttcttgaca ttggaaccaa ctatatcctc taattaggca acaaaaggca tatatatgta   33480
tatttttaaa agtagataag caaatataaa ttatttctct aaaagttaac atgttttta    33540 aaaaaagcat aatttgtaat ggcaaaattg atattttcca caacaggtaa catgcaggag   33600
cgatttagaa tacaaaagga cttttccaaag gcaagtcatc cagatgtcca aatggtggtg   33660
aatacagcct ctggagtata cgtgggtgga aataaaagtc aatttcacag tggttagcca   33720
cctccctgag cctttttttt cccctggtgg gacactgaga cactcgcaaa gcagcaaaag   33780
gtctcagtgg accctcttg ccattactca tgggtgtgga gtttatggaa cacatggagg    33840
ccgcagtggg agagacctga ggctgcagag gaaccacccg aaccttgcta cagcaccagc   33900
agtatgggtc cgactgcttt cttggccact catatccagt ggatggaatt tgagacagcc   33960
tgtgtccata ctagattcca ctctgctgat tcataccaga atgaggttct agagtacaaa   34020
tattcacaac cagaaagcac atctggcctc agtgcagctt tgtttacttt gctacttagg   34080 aaaaaaaaa atcttgaaaa gcgagttgct tttgccttaa ttcagttcaa atacattcta   34140
agcttccttc aactgagtca cagtgtcctc tatcatgcaa aatctttatt atttccttgg   34200
ccagacatag ggccatattg atgaattcca agtgtgcttt ctaaccaagg ctggttcaca   34260
acaaaaagct gcttcagctc tgagtcatca cctcaaataa ctgatttctc ttctcaggaa   34320
tgagactagc aactttaatc cataatttttc ttcctcttct aacaacttttt ctcaaccata   34380 tttccacact tatttttttct tctgcattta gaccagaaag taaatctggt tgtttctttt   34440
tgaaacaaaa atgcacagct ggaaagccag ctattttgag gcgtgagtgc acagttccaa   34500
ggcagcatac ctaaaatccc ccagagctac caaaacacca tttactcttt tcatttctta   34560
```

```
catgcaagaa ctaatcattt ccccaagaag ccagctccct ggtgttggag ctgaacaaac   34620
ataaaatgag atttgggaga agagggcag catttctaag acttccctta ctcggaaaac    34680
aacggaagtc aacaaaatgc tcaatgcatg cgatcagtac acagagtggg tttgctggat   34740
ggtgtaaagc aacgacatta aggacacaat gggtccagag ggaaccagct ggctgagatg   34800
ttctgctagc aagttaaaca tagacaggaa accgcgtgtc tgatactgta aaaaaataat   34860
ttgtcttcct gccagagata ggctagcaaa ccaaaaaggc tgttttcact taaaagaaat   34920
gctacaacaa tgagagagga aggaatgaaa ctttgtggct acaagaagtc ttcttctctg   34980
cccctctctc aacatctcag gttagagggc acacatcacc acactaaatg ctaaagcctg   35040
cacatagctt gcgagtcagc aacgtgcacc actgggcata catcttatgg tctgcttccc   35100
tatttaacca catagattga actttgagtc agaagtggtt actcaagtcc tggtttctaa   35160
gctagcaaga tataattgat ttatttactt acagtcctat cccattccca aaaacaacaa   35220
caacgacaac aacaaaaaac acagtgaaag aagatacagt caagacagga gctataatta   35280
tgacaaatgg aatataaatg tgagaaaaca gggtaaaaac tggtaagcaa gagtgatatt   35340
agtatgctaa atgtgtaggt acatatttgc tagaagcatg attcagattt gactctaagc   35400 tttttctggta gttagcattt gagagagaaa cacaaaaacc atgaatatct ctatcagggg   35460
ttggcctgag ccctgttttt gtaaatgaag ttgtactgga acacagccac gtccaatcac   35520
ttacacactg tctgtggctg ctaccacaga agagttgagt agctgtgaca gagactctgc   35580
cctgcaaagc tgaaaatatt tactatcttg cctgttatca aagaagtttg cagacccctg   35640
ctcggtatgc ttcaaagtgt ccttaagatc agaggcaaac aggtcgtcat gaggagaaca   35700
cctttctaaa acagagagcc aaaataaatg tctcctggct tcctcatgaa gataacaata   35760
caatgcagtg aacagcatcc tccacattct ttacagtaaa cataccactt tgattcacag   35820
gactccttat aatggggagc acctcaatag gactcaggtg gaggaatttg cagggaagag   35880
gagaatacat gacgttggta caaatctcct cactcatcca gctaaaggca aagataagaa   35940
atttgaatct agtggaacag taataactat ttacagtcaa aattcattaa gtgctcactc   36000
tgtgccaggt gccgtgccaa gttctctaca taaataaata catttatcct caaaataatc   36060
ctattaaaag tattcattat ttctactccc atttttcaga gaggtaaaca agtagttacc   36120
ccaagaacca agagcttaca cacggctgag ctgggatctg aacacaggca atcagcaggg   36180
aagccatgct ctcagccctg ccctctgttg tcttcccaac agatgagcat cttactggcc   36240
atcgtttata cacatcattt ctcacggaca tggaaacagt gtcagcctga ggttgtgcct   36300
cttgccaagg acatgctcag tgatgggtct gggctgccgt ttggcaaaca gaacaggtag   36360
cctcttatgt aagttgtgca gcctcccatg ggttaagact gataaaaaag caaacacacc   36420
accaccacgg gaatgtggaa gggtaagggt attccttcta taagagacaa gattatctgg   36480
ttcttctatg attctcctac ggacaaaaag tgaggaacaa actatgagat cttggaaaat   36540
cccagctcct ctctggagac ccactttttt gtcattaaaa tgagaagtct ggaggagcca   36600
attcacgggt ttcacttcat cataaaaatg taatgagtct atgaaacaag acaacacacc   36660
tgaaagtagt tagcacaggt gcacacattc agagtaggct gcaatccaag gcagcgatca   36720
tcactatagt tgttctatga gttcccacag cctaggccat gggcttgcca ccaccttgcc   36780
tacatttcaa ttggaaaagg ggtgggaccc tggtcctgca aacaaactac tgaaagtcta   36840
ggacttgggt ccaatgctat ccctttccta tatggcccca gtgcctctca ttttctagaa   36900
taagcagttc agttctaagt tagcaggaaa agcaagatgg ccaagatcca gtcatttggg   36960
```

```
agctggaagt ggtccagcag catgcctccc ttcatcctcc ttggcttacc atcttgtttt   37020
ccacgtaccc accttcagca gacaatctta gcaaacaacc caagaatgaa ctgattcagg   37080
ccaactcttc ttagaaccac actattactc tccagggctt tccaaggcca ccaaacatct   37140
ccttcattga tccagttcaa aacagtatct tgtacaatgc atcttgaaaa cattcgcaaa   37200
tgtcttcttg ttttgggaaa tattaaggga tagtcccaca gataaactaa tacaaataca   37260
ataaactaac atgaacatga tcacagaaac aaaagaaatg cttactgaaa aggtgtctga   37320
ttttctccac attaagatcc acaccagaac aacatttgtg gagtatattt aaaaaataaa   37380
ctattgtcac tgctgaaaaa gacccacatg ccactggaga gctctgttac acaagctgac   37440
tgagtaaagt atatttagtt catttccaaa tgaccaggct ttagaccaaa tttattcctc   37500
atgggcccat tagctcaggg agttaccagc atgaagttaa taagacctcc atctctggtt   37560
ccatccctac ctggtgagtt cacaccagtg cttctcacac ttcagtgtgc aaacaaatca   37620
ctgaaggcct tgttacaggc agatgctaat gcaataggcc ccagaggacc caaggttgtg   37680
cagttctaat aagctcccgg gtgatcctgc tgctgctggt ctagacactt tcagtagcaa   37740
cggtttatac cgttcagaag aggtatgtgt cttggtgtag agtgttctcc ttaatcaggg   37800
gaagaagaag taagaaagga tgcacctact gtgtgccagc cactgtgctg ggcgctccca   37860
agcatcatct ccttaaatcc cacaacaacc cacaggtacc atttatcagc actacttggc   37920
caataatggc gcagtcattc aaagagaagg ccttgtggcc caaagcaagc tttccatgga   37980
aaaaatgaag agggaatgaa tcccttggc aagtacagaa ctgcgattac cctaatcact   38040
tatgtgaaag gcacttgtgg gttgtttcag ttttatttag ctgcttcctg ctgtgattct   38100
gagtcaaaac aggaacaacg tgtctaattt gtaatattat ccaacaatga cagggatgtg   38160
gttagctttg attagaaatt ctagactcag catgctcccc ttgcctctgt gaaggcatgt   38220
ggagaaaaag agaaactgga tgaaacaggg attaaagcaa agtgagcccc tccaaaacct   38280
tgtggtgtga tatgtaggta tccgaatgct cagtttatgc accacagtca gcactcaact   38340
acaaaacttc agtgttagaa cagaccgaag gctacacagg cctggtttcc tgcattcaga   38400
caagcacaag tcaccagccc tctataaaaa gcccaactac tgctaacagc taacagacag   38460
tgacatgtca gcaacgttg caagcacttt acatgcatta atctactcaa tcctcacaac   38520
acctcccacc cgctttgtat ttccatttta cagatgaaga gactgaagca tggagatgtc   38580
aagtcactgg cccaacatag cagagctaat aagctgtaga ataagcctta aatccaggag   38640
atctagctca ttcttgagta ttacactaga ccgtttctct cttacctaaa ccagcagaaa   38700
tcacctcttc gctcagtgtt ccacaaatta aatgtctgac tgcacttgga aaccatttat   38760
gaaatgaata aaactgagtt gttgtgtttg attcttacag gttcagtgag agatcaataa   38820
ccatatcatg tctttgcaaa gtggggatgt cattggcaag taaacagcat ggctatttgc   38880
tcaggattcc ttcctctcct acctcctgtg ctgctgcctt cagtcctggt gcccatcagg   38940
tctcgtctga ctgacagctg tcaccaggcc atccatcatg accaatccaa acaacttctc   39000
ttctaattgg aatttatat gttggttagt acagggatag actctgattt ccttagaatt   39060
ctacacaaaa tgttctggca ggagggaatc ttcagagact gggagggaag catgaatgtg   39120
agagaacagt tgtgcagtgc agaccccagc cccattctag ttgtttcttg accccctgcct   39180 gcccttggtc actgtaggga ggcaggggaa ctggcactag gccccactga gggattccag   39240
ggttaagggt aggtacccgg ttcaagaaaa aaacagcaa ggtttcttta actctttcat   39300
tctaaaaacc atgatctcag tcctctgagg aaagggcatc tatgacacca gtgtctgatg   39360
```

```
tcaagatgtt accgtgttcc tctgcctcta cagacaacca agcctcattt acaacaacaa      39420
caaaaggaac aaatgttaaa tctctgcacc attttgtcta gatgtttgaa tttgtctagc      39480
atttgaattt tttatcatat gcatatatta tctctttgga aacatacaga gatataaaga      39540
gaaagaagga aataaaaaga ggaaaaaagg aaagaattaa aaaaggaaaa aaggaaaacc      39600
ttcacaggtt ttagtgcctt acatatccca ttataaatcc tagctttgat acccactagt      39660
tgtttgattg tagacaaagt gttaaatttc tctaagcctg gttttctcat gcataaacag      39720
ggatcctaac agtgcctact cgcatggggt ggctataaga ttaaatgagg tcatgcttgg      39780
aaagggctga gctccctgca cagcgacagt atgttttctc tgaatattaa ctatcattaa      39840
tagtagcact agaaataaag atccatactt aaaatcttgt ggctcaactt ttttttctta      39900
catattaaaa aaggtagatg tacataatta tcatccattg tgtagctgca gatcaggaac      39960
ttgccaacaa gagtactgta ctactaataa tacagccaca atgcacttca tagcttttgt      40020
gttcaccacc ttgttggact tggagtagac aaatcaacat taagagtttt cattctggcc      40080
gggtgtggtg gctcatgcct gtaatcctag cactttggga ggctgaggca ggtggatcat      40140
ctgaggtcaa gagtttgaga ccagcctgat caacatggtg aaaccccgtc tctactaaaa      40200
acataaaaat tagccgggca tggtggcaga tgcctgtaat cccagctact tgagaggctg      40260
aggcaggaga attgcttgaa tccaggaggc agaggttgca gtgagccgag actgcaccat      40320
tgcactccag cccgggtgac agagtgagac tctgtctcaa aaaaaaaaa aaaaaaagtt      40380 ttcattcctc aagataaaga agagatggtg gcaataaggg gagaaatgga atataaaatg      40440
ttgctcctaa tgtctgctgt tttaggtgga agaaatatcc caccacacag aaaagagatg      40500
cttaaaaagc aaacaccccc taccttctgg agcattttag aagactctga aatcacccag      40560
acatttgagt cgtcagctgt gaaaggcttc ctgtactgta cagtgagaaa ttgtctttat      40620
gcttattatc tcacttcata agaaagtctg agaataaata agaggaaaaa tatgagggat      40680
gcccatgatg atcacttgag ttgaaagact ctgaaaatgg aagtcattag tatctgaaag      40740
gctcatagta aaatataaaa tgcatgatat attttgacaa agatattcaa tgataaaata      40800
tagatccaac ttgcaggcca tttatcaact tttgtccttt tggaggaaat aaacttgtct      40860
actgtagaca agctggtata cagaaggaga gaaaagtttc ttcaatgcta gtaaacatgc      40920
ctgggtattc tactgtcaga gattaattcc tttggcttag cctaggcctt cttttaaaag      40980
gtgatctact tgaagaaagc tgacctggta agtcagaata tcaggtgtta ccatgtttca      41040
tgtgattaaa ctatttagat ttccctccta actcaaatca cataaagaac atgaggccaa      41100
gcacagtggt tcatgcctgt aattctagca ctttgggagg ccaaggcagg ttattcacct      41160
gaggtcagga gttcgagacc agactgacga acatggtgaa actcgtctct actaaaaata      41220
caaagattag ctgggtatgg tggcacactc ctgcagtccc acctactcag gaggctgagg      41280
caggaggatc acttgaacct gggaggcaga ggttgcagtg agccaagatc gtgccattgc      41340
actccagcct gggcgacaga gtgagactcc gtcaaaaaaa aaaaaaaaaa aaaacaacc      41400 agaaagaaa acgagagaaa tggaccattt acaggatgag gatgagaaca taggaaggaa      41460
gagtaatctg gaaagcgttg ccctgacaag atgtgcatgc ctgccttcag ttcactgaga      41520
agttggcctg gggatgttg gacaggaaga tagggagaat ggcagtaggt gaaggacaca      41580
ggaagagaac aagctggatc tgcagtgcta ctgagcacca aacacgaaac acgaggacac      41640
atagcttctc gcaggtggaa tgcacatggc cgcagagata gggtgtagag ccagcatttg      41700
tatttcaaaa agatttttta attaaatcag acctattgtt gactaaacta acatttacac      41760
```

```
taccacgctg gtaaaattaa aagacttatc cattcccagt gttggagaag gtacacggaa   41820
atccatatgc ttacatcctt ttcaggagga gaatagttta gtagtgctta ttcaaattta   41880
aaatacacat atttctaatc tagaaatttc acttctggca atctgccttg cagaaatatt   41940
agcacaaatg catgagatat ttttacaaag atattcaatg tagcattaag tggaaaaact   42000
gaagacaatc catcaacagg gacatgataa gatccatcgt gggagataat atgaaattcg   42060
agactaaatt aaaagatgta cagtatatct atgtgttcta tcttgtttag aaggaattgt   42120
aaaagtggtt gggtataaaa aagtgttgca aaataatatt tatagtatga tcagatagtt   42180
gtactgaaag atggatgagt ggatggaagg atggacagat ggatgaaagg agggaaagag   42240
aaaggaagac agggagagat tgggagagag gatggagtgg gagataatat gaatgaatga   42300
tagagacgtg tgtgcatcta atacattgtc aatacagatg atctgttgca ttgggagtga   42360
ggggaggacg aaaatgtact ttcattttta atttttcacac actgttggat tgtttgaaat   42420
ttttgatgac gagcatatac tacttttgta attaaaaacc actgaattct cttcttatta   42480
aaaattgagg gaatagtgta tgccttcctt tcaagctgag taaacgctga acttcaaaga   42540
tggaggctag tatctaatct actcttctcc tggctctagg ggtaaacttt ggcttattat   42600
ttcctctctg tattgcaatg tttctctcaa atgggatcga tgacaagtac cctaaagaca   42660
aatcctggga ctatgtacaa gaaacaacat cagttataaa gaaagtcctc ctccaagatt   42720
aaacaacccc atccaaatct ttagaacaat agttaccaaa ttttagctgc acagaattac   42780
tgggagggct tgttaaaata cagatagctg gggttcaccc tctatgtttc tcatttagtg   42840
gggcctgaga atctgcattt ataacaggtt cccaggtgat actgatgctg gctgctcaag   42900
gggccgcact ttgagaaaca ctgctctagg tgaaagaaac tatttgtcaa agacaaataa   42960
taatgtttgc cccagtcaac catatttgat gagaaccaga acaaaccctg ctactcccca   43020
agcccctctt tccaccagct gaatgagctc ctaatccact gtatgcaatc caccacagga   43080
ggaatgtgct ctatgacact gcagaccaag gatacaaaaa attggcacag atctcaggtc   43140 ccacacccctt aagagaagaa aactcacctt ctgagaagat gatgttgtca ttgcactcat   43200
cagagctaca ggaacacatg aagaaagtct caccaggctt ttttttttcc ttcataatgc   43260
actttggaga agcagcatct tccagaataa agtcatggta ggggagcttg gggtcatggc   43320
aaactgtctc tagtgttatg ttctcgtcat tctttctcct agagtgaaga gattcattgg   43380
aagcgagggg agagggagag agagaaagag aataaatgaa taatatggcc tccagacaga   43440
aaggcaatct ggaatacttt tccttcatga agttgttcct aacaacggca gctggttcct   43500
gttctccagc attcgcaggc tgtcctatag tctcctatgc ttttctactc ttttctgttt   43560
ttcctttgtt tattcttgga acccatttgt gattataaac atcacctgga gcagacagcg   43620
ttccacgggg cagtcctggt ggagaatttt acatatttaa gtcttaatta aatcattaaa   43680
ggggaagaca tggaaaaaaa gaacattcct aggtactcag gataatttta aatcttccat   43740
cctgaatgta atgcaaacct cacatcacac ccctagttta actggcaaaa tctgtcctgt   43800
ctagctatac tgttttcaaa gagcatgcct ggggaaatag tcacagttcc tctttttttt   43860
gtttgctggg ccccagagca ttgcgtgtaa agggtatact ccttgtcaac agctggttct   43920
gctgagaaaa acgggaagaa acatcgcaga taaagaactg cagtctttcc caaattacag   43980
aaaggagcaa ttcagaaaaa acaaacaaac aaaaaaaaca aataaataaa agaaatggaa   44040
aaggatgtca gggtgttctt catttacagt tcaatgaaat attttatgct gtcataaact   44100
aactactttg acagtatcac ttcatagcac atatttgaag actaatttag cccagggctc   44160
```

```
agagaatttc tcacatagca ttttccttgg gccctaggaa atgctcaatt ggccgtcagt   44220
gtacattaga tttttaaaca acatgattaa tgcccactat tataattgaa caaaagaaca   44280
ttttggctct cttggaaaag ggtatcacct ctctatctac ctcccctctgc tccctcatga  44340 acatactatc ttggatgact gtccaacaag gctagtctga catccaccct ttcacctctg   44400 tccttttttag atgcaaaata cctgttgtct tgaatcgcat tctctctgtc tagagaggga  44460
gcggaaggaa gggctaatct ggtccagtca gttttgctag agtaatcttc tatgaagatt   44520
ctgagtgcac acatgagcca atgcatgcat gtactcactc accaatttc ccctaatcct    44580 ccctgcccca tgcacaaagg ctcactgctc acagcaagga aaacggaagg caggctagaa   44640
gcaagaagca gctaagacac agcttgcacc tataaaagat gcggggccat ccccacgaga   44700
gaaagagcaa ctttgaccaa taccactttt ttagtgctta agtcaaggac attaaaggac    44760
aatatgttga caaagggata agggcaaggg tatgggttag acaatccag gcaggaatgg    44820 tgccagtgtc aacatccatg cagcccagag ttgactccag tggaggtaca tgtgtctgct   44880
tgtgaagggg ctcaagggtt cttaaactag aattccgaaa gacacaagag gagcaaggct   44940
ttgctaagtt ggtccctgct gtgacaggaa gagtgacaag cagaataatt ggttgagggt   45000
ggctatcagg acaccaaatg aaactaaatg aaagttggca tgatcataca acaaatgatg   45060
tataatttgg aaatctaccc atctttaacc ccaaagctac ttggcagtct tcaaatcagc   45120
tgtagtcatg gaacaagaac accttcctcc ctgcccccac agttttgtgt gtgtgtgtgt   45180
gtgtgtgtgt gtgtgtgtgt gtgtgtgtag gttgttttg gtttgggtaa taaaacgaag    45240
gtatgctgtg cccacagaaa ggcatggtct cttttccttg tgacgcttat agaggcctaa   45300
gaaggaactg tgagccatga agaaagctg ctctataatt attgggcagc tcttccagag    45360
cctccggttt tctacctctt agctactgag agaactaaca tcacagagag aaaacaactg   45420
taatacttga gacctggtaa agcccttaac tgctttctcc actcactcct gtaacagcca   45480
ggcacagcta acttttcaaa ctcttttttgg atatagctga gcataggaaa ggtaaataca  45540
aagaagtaaa tacggacttc ttttttttgtc ctgcaacatt tgctctgagc cactgaagag  45600
gttgtcaatt tccactgaaa gaagaaccaa catgataaaa ttaattttgg aggctgggca   45660
cggtggctca tgcctgtaat ctaagcactt tcagaggccg aggcaggcgg atcacaaggt   45720
caggagttcg agaccagcct ggccaacaca gtgaaacccc atctctacta aaaatacaaa   45780
aaattagcca cgtgatggtg gtgtgcacct gtaatcacag ctactcagga agctgaagca   45840
ggagaatcgc acgaacccgg gaggcagagg ttgcagtgag cccagatcac gccattgcac   45900
tccagcctgg gcaacagtgg gagactccct ctcaatttaa aaataataat aataataatt   45960
ttggttataa atatttcta tccttggagg cagcttaagc attttatatg gaatgggcac    46020
acaactgaca ttagttaaat gaatgaatga atgaatgaat gaatgaaaaa acactaaaac   46080
tgattaaaaa aacaacaaca ctgaaatcta caatcatagt agagcctttc agtttccaca   46140
ctggctattt ttacaatagc ctcctgtctt agtttaggtt tcctggaaac agaccttgag   46200
gctgtgagag ttctgtgcag gaggttttg gagatgcatc tgtaagcgac taaaggcaac    46260
agtattgcac agaaggaaaa agctaaaacta taatgcaggt tgcagcaaag gcctcagtga  46320
atgccttgga aactctgaaa atgggatgtc cttcaaagat gtaccacatt atggcaaaat   46380
aaccaggaat ttgttctct gcatcaacta gccatgggat gatggctacc catgaaaagt    46440
gtccaacgtg aatgaggcag ctcccatcac tggagggaag gctcagcagt gatccttcaa   46500
cagccaacac tcccagggaa tgagtgcctt ggtcatgaag gaggatcaag gagggcacta   46560
```

-continued

```
tagcgtaccc tatacttccc cttctcatta tcaacacccc tggcttcacg ggagaatttt    46620
ctttggccag cacaggtcaa ataatgttc  attgtattta ccctttatag ctgggacaca    46680
gaaaagacag ggaggcctcc tctcttcgac atgctcacat ttttttgagg ctagcaaagc    46740
ctctattcta gagagacttg attcacattt aatgatttgg gcttgtatta ctggtcagga    46800
aaacaaaaat cttaattaaa agagccttt  tgggttgcaa aagcaagtgc tcacaccacc    46860
gtagatattt aagaaaccac ggaaggaagc tttgaggcca tctagtctgg tgtctcaatc    46920
tttcctgcat tctatttgac atatggtcat ccagcctctc ctgaacttca cttggtgctt    46980
acagaaaagg aagcctgttc tgctgttggg aaaccatgat tgtgaaaatg tctaaactta    47040
tgctgagcac aagtctgcct gccttgcaaa tgttatggat cctccctcta cccttcagag    47100
ttatgcagaa tatgtttatt atattttcta cctgagagcc tttcaatttc atcagcaaa    47160
cccacgatct ctcttcactg tactaaccat gtctaattgc ccaggccatt cctcagacag    47220
catgatttct aggcctctaa ccacactggt ccctctcctc tgaacacatt ctttgtccaa    47280
atcctttctt tgaaagcgtt acctagaagt ggacatggac aggtatcata tcatattggc    47340
aagtatgtca tgacaagtct ttgctgttaa cattccttca gttcttaaga aaccagttca    47400
tcccgtggta tgtacagaag tttgcaaggt ttccagatct atcatcaagg ctagctttac    47460
atggtctagg ggtctcaaat gactcattcc caaaaaggg  ggagagatat ttgggtttat    47520
attcttgttt gtcaactagc caggagacac ataagttact ttttttaaaa tggccaataa    47580
attaaaaaca tcagaataag tctgcaaaat gtcatatctc attaatgaat ttatgtactt    47640
ttgtaaaatt acaactcttc taaagatcaa ggttatttct tgttcatgct cacaatctat    47700
aaccatgaat taatcaaatg attcatgagt atccactgtg tatgtataat tattatttga    47760
gatgtatgta tgagttggag ggaatgagag agagagagag agagagagga gaaaatgtga    47820
tccgataaaa atatatagtt ctggtcgggc atggtggctc atgcctgtaa ttccagcact    47880
ttgggaggca gaggcgagtg gatcacctga ggtcgggagt tcgagaccag cctggccaac    47940
atggtgaaac cccgtctcta ctaaaaatac aaaacttagc caggtgtggt agtgggcacc    48000
tgtaatccca gctactcgaa aggctgagac aagagaaacg cttgaacctg ggaggtggag    48060
gttgcggtga gccaagattg tgccatggca ctctagcctg aatgacagag caagactcca    48120
tctcaaaaaa aaaaagaaa  tatgtagttc tgagctgaga gaaagaagtc atatctatcc    48180
caatggttat atgaataata taaccagaat ttctgactaa aaaaacaggt tgttttgtg    48240
gttctccaag tagattcccc atttttggct ggtagttttc tcttccaaca gccaaccttt    48300
catcacctct tcttccagac ctgagattgc ctcaagagaa caaagctcct ggtctcacta    48360
tggggtgctg aggaggtgtc ggttaaatga ctactaagcg gcaaatccct cttcttgata    48420
caagaaagag tttccagatt tattatatta aagatcattt tatgatcttt acatttatca    48480
tgatcatttt ataatcatga tacgtttata tacccacata aacgtacaca tacatgcaga    48540
gaacacccct agaaactaca tttaataatc gaaagagaga tggtctaaag gaaagggaaa    48600
tggaacaggt gtttacattt aggagacaga gatacactga ctgtgtgtac tatgagaata    48660
cattatgtaa aaaggggaaa agaaagaata acttcttaaa aggcttgctt accatacagc    48720
cacacagact tcctgtggct tctcacagat ggaggtgatg ctgcagttgc tcatgcagga    48780
tttctggttg tcacaggtgg aaaatctcac atcacaaaat ttacacagtt gtggaaactt    48840
gactgcaccg ttgttgtcag tgactatcat gtcgttatta actgaggaga gagaaagata    48900
tattaaatga ttatccaact gccaggcagc ctgccaatga attcctgaag atgttatgca    48960
```

```
atttcaaatg aacttgatgt catgagaatg aatctgaaga aaggcaaaat aattccttca   49020
catcagatta gaattatctg gtgtatgcaa tttgtaataa aatccattgt accgtggtga   49080
ggggtggtga ggggttgggg tggttgagta gccatttgct tttgtcaatg gttgtcataa   49140
ggtccacttt ctacaaaaat cttatcattc aataaagaaa cctagatggg cccactgcat   49200
agtacggagt gctgggccca caaataaaag tacccttaag gaaattatag tttagctggt   49260
gaataagaca ggaaacagac caagtcaggg tgacccaaaa tagagggcag cacagaggat   49320
gtgggagcca ggcgagcatc accgctcagc tgggcaggga ggctataacc tcacagagtc   49380
atgaagtgcc acaccaaagg aggaaccgtt gctggaggca caagattttg ccgccatttt   49440
cctgacctac tcctgaaaga gctataaggg tcttcttttc aagggactag ttctactgat   49500
ctctctctgt gtttgaggca aatcaattga ttaactaaca cttactgagt gcctcctaga   49560
cacaatccca agcattggtg aggcattgga gttatgatcg cagcaaataa aagctgaatc   49620
cacctcagga tctgccttct gtacctctcc cttatcacca ccatcaccaa tctcctgccc   49680
ccttctggga agaagccaag ttcattccct cctcaggcct ttcacttgct attacctttg   49740
tttagcttcc tgtcactttt ctgatctctg atcaaatgcc acctcttcat cctatagcaa   49800
ctctgtttta tttattgtct gcacaaacta tctgcatcgc atacttgcta ataatctatc   49860
cacaaaaatg taagctccat gaaactttct ccacctcact tacctactat atctccagtg   49920
ccaggaagag aacctttcac atagcaggca tacaaaaatg tttattggat aaatgagtga   49980
acacaggatg aatacaagga gtccatgttt ggcccttgat gccatgtagg ataggataca   50040
gaacttcttc actcagatta gagaggaatg tgattataaa tgtgatattc attcacattt   50100
attcaataaa atatggaaga cagactattc tttgcaaaat acaggctgca aactaggggc   50160
agttcaaata aaggtgtaac accccattcc ccattttctt cctcaatgag atggtgatga   50220
tgtttaagac atgagtttgg acagtcagtg aagtatgaca aggctactag gcactcaacc   50280
agcaaacatg aattaatact tacatgctag actaagaaac attaagcact tagaccgcat   50340
ggggtgctgg aacagttgct gggccacaga aagttgtgag gtactttttcc aaggcataac   50400 ccttagagag gcctaagaaa agcctcatgt tccctctgct cttgcctaga gaggaacact   50460
ttcaatgcct ttccacagtc actctctgtc ctgtgaattt taggattctg tcatagatac   50520
tttgccctgc aactgtcttt gtagcttggg catagcacct gtttcctggg tctctaaaaa   50580
tataaacgta tataaattta agatttgctt tcttgtggta acagtaaaata tagaagaaaa   50640 aaataaagcc attcatccct ctcgggcctc aagttcattt caggaagttt attttttaggt   50700 aacaagctat tttgaaattc tcagtgtctc ccagaccaag agctctatgc ttagctaaaa   50760
atataggcag aaatactctc tgaactgtgt gaaatttggg agaaacacaa caattaatat   50820
gtattttttt ctaacatggt tatacttgga tcaattttttg aaacaactaa taacacttta   50880
ggtttcttta acattgttta aagcaaaaaa aaagtgaaac cacgttttgt ttatttcata   50940
catacgtatt ttttgtatag agtatgtttt ggacaagcat ctatttgctg attaggaagg   51000
tttgttgttt gtaaatataa aaccaaattt ccattacttg aaattcagtc ttccaacatc   51060
ttaggatttt agcttagatt ggtggttatc aacttggaga gcatgttgaa atccatcacc   51120
tgaggaaatt taaaaaatac tgaagggggtc ccactcccag atagtctgat ttaatttttc   51180
tggaaggtaa ctgaggcatc aggatttttta gaagctgccc agatgattct aatgtggaac   51240
caaggttgag aacccagacc tatagttagt tggaaaaaac acaataaaca gaaaacaaaa   51300
cagcaacccc cccactccca ccccaccacc acaaacacat atacaactta tgctgctgag   51360
```

```
gggacagcac ctggatatag ctggaattag ttcccttgtg aaaaacatgc acctaaggag    51420
aggtgattag ctcttttcaca cctcagatag aaattcttct ccgtgctggc cagtccttt    51480 ctagcaaaac cttagaaacg tgagaatagt gacaggagtg agcagcgata gataagacag    51540
aaatgaaaac agatgagatg ggtgctggga gcagtggtgg ccacagatgt attgacaaat    51600
gcaagtggtt taagtccgat gcttgcagaa cacaatcaac agggaaaaga aaaaggacc     51660 attagaagaa agaaagggag agaaagggaa gaaggatgta gggagagaga gaggaaggaa    51720
gggaggaagg gaaacaagga gggaggggga ggagagagaa agagagagaa ggtccaccaa    51780
tttgcacagc tccaggagca ccactgtaac ggggcccctg gcgagatata atacatgtta    51840
cttgatgggt agacccaaca agagaaagcc tttccattga atgttgaaga aaagccaaac    51900
aagcaactgt actgcatata gacacaggca tatggtggga agggcagtgt acaataagaa    51960
tttgcacatg ctgagcaccc actgtatatg aggaaagttg cctaagatac agcatattac    52020
ttcacaagaa cccagccagg gatgccacat ttttctcctt gttacagcag aagctaccac    52080
tgcaagagct taaccagaat tttttttcaa aagcctgtat gcaggacatg ttcagcacca    52140
gccatcgact ccctattagt tgaccctagg agactcccca ccttaacaat tccaggtagc    52200
ccttgaggtc atatacattc aacctttgt tttaaaccag tattctttc ctctatatga     52260 tataggtcct caggtccttt tatgcatacc atatgtactg gtggaatagg tagttaagtt    52320
cagagggcaa agctactcta aacctttgct ggagtcacct aagtttgata aaagccttat    52380
gaacacactt tggagttggg gaaaagaaac aaatacaaaa tttgtagatc atctgagaag    52440
gtttgcagat tctctgaggc ccgtaagatc cagttaaggc atcccaagcc aaccccggaa    52500
tcctcaagag tcactaataa catgctaagt ggtatactgc tggtcagagt gggatgaggg    52560
ccagtgggag ggaagggtaa cagtcatttg ctgtatggga cattgcatct gtgcactcca    52620
aaccacagga aaagatgtta ccagccacga cctcagatat caaacaacat ctccttacgt    52680
ttaatacata atgtttaaaa agccaaagga atgggaagga aagtaagtgc atacatgtgc    52740
atagctagga ataaagatat tcctctaaac aacgatacaa aacccaccta attaaccta     52800 tagcaaaccc taacccaact tcaacattac ttttaatcca gattgttata ttagtctaag    52860
tctctctagt taagatattc ttatattaag gcagtatata gtcagccttc tgtatctgtg    52920
ggttccacat ctgcggtttc catcaaccgt ggatgcaaaa tattttttta aaaaaattga    52980
tgattgtggc tgtactgaat tatgtacaga cttttttctt gtcattattc cctaagcaac    53040
acagtataac aactatttac atagaattta cattgtatta tgtataagta atctagagat    53100
gatttaaagg atatgggagg atgtgtgtag gttatatgta aatattacac aatttttat     53160 aagggagtta aacatctgta gattttggtc tcctcgagga gtcttggaac caatccccca    53220
tgggtaccaa gagatgactg tacttcgatt cctatagact ctctgtgagc agctaaccat    53280
ctttagagaa ttttctaccc ctaataggca aattcgttat tcataaagtt ctccagaaag    53340
aagttccaat aagaatatct gtcacctaga aagccatcca ctaaaggaag tgaacatggg    53400
tagcatctct cagcatatga tagtatcaca tggcccataa tatttcactt ctcttcaaat    53460
aagcccatga gtaatatcaa aaccttcact ctaggtcata ccaccttccc cattttatct    53520
cacattttcc ccacactcac tgcctacaga cagaggttcc aggtcttgag aatatgaatt    53580
gactgcttag ctgtgtctat ttctggaact gtactattgt cttgagggt cagatgagca      53640 gcctaataag atttagactt atttcagata aatattagaa attctgaata tgaccttagt    53700
ccaaatcttt gaaatagtgt ctattattag ctgaaccatt aggtaaaatc tcaaggttta    53760
```

```
acaataacca taaacacttg tcagaaatgc attcatgtat cactgaattc atgcattcgt   53820
gtatcattga attcatgtat ctaccgactg ttgttttctg gagtgttttt tgtgggggga   53880
aactcagaaa tttatttgtt ctacaaatac ctgtggatgt cttgattagt gttatatatt   53940
catagtaaga ccactgaaat tgacacaatt aaataacatc tcaaagaata atccatggaa   54000
actggtggat agaatttact gttttagagt actgcttctc aaatattaat acacaagtac   54060
tttgggaata ttttaacct gcaggtgtag catagtggta ttgtgggggc tggcaagtct   54120
gaaatttata gggcagactg gcagcctggg aactcaggca gaaatcaatg ctgcagtttt   54180
gaggcagtat tttttctctc agaaacctca gcttttgctc ttaaggctgt tcagttgatt   54240
ggatgaggcc cactcacatt atagagaatg atttcttta cttaaagtca aatgatttta   54300
gctgttaatc acatctacaa cataccttca cagcaacaat gagattagtg ggcaccagaa   54360
cctagccaag tacacacgaa actgaccta cagataggaa gggagctgct gccctgggtg   54420
atgccagccc actatatgtt gagtgggaag gctgtggaga cccagttt taataattgt   54480 ttcccttct ccagtcattt tggagttagt gaaattaaat acctattctt cacctttta   54540 caggcatttc tcatcttcca gttctttcca tatgctttc tcttgagcct gacctcttaa   54600
atgattgcaa acccagaggc cctgatcacc atatgggccc agaattgaaa gacatgttct   54660
ctgaaaggag gttttaatt gcctgcagca tttccgagtc agatactgag gcagccatct   54720
ggcagaaagc cgctgtggcc tgtgatgcta gcaacagcag ctccgaccct tgagacaagg   54780
tgggacaagg ctattggcta gtcacacact tcctcccacc cagaacaaag aagaaagtca   54840
agcaatctga gaggattccc tgtataattc ttcaggaaag acatcccaa gccaatcaga   54900 taccttggcc aattactaca accaaccaac caaccaaaca aacaccttgt gattaaacca   54960
aagataggaa catttagga atagttcttt ttgctgaaca tctattgcac actctaattg   55020
gaacttctaa tacaataacct tcttttagt ttttaaaaat gtgttgaac cctaatgctt   55080 tatctaatta taccttgaga gaagagaggt atcgggcttt ccttcaactg acagtccaca   55140
tggtctctgg ggtaccaagg tcaatactag agataccatc atttagctaa cagggagact   55200
atggcgtgtg caggaagaaa acagagacaa gtgacctgaa ggcatcaatt ctccttctta   55260
tgcaaatatt tttgtagtaa taatacttta aaacctttca gagatgacaa agtgaatact   55320
ctaaaatctc tgtgaaatga caatgcctta taattcttgc ttttaaatag taagtattct   55380
acaagtgcca gaagaattaa tgccatttaa aatcattatc aatgcttatt ggaaacaaat   55440
aacaaatcat atgagttctc tatattgtgt taaaaaacg ctactttaaa tattacttcc   55500
tgatcatatc accagagaat aagctctaaa agcgaagcat gtcaacctca ttgctaacaa   55560
gtgaaatgca gattaaaaat gcataccata tttcacctaa ctcattttga aaaagatcaa   55620
taagtcagat aacacagtga gctgggtaaa gtatggggaa acaaacattc tcataatgct   55680
gtgttgtaaa caggtataac atctcaggag tacatgttat tgatatcaat caacactgca   55740
aacgcaaata gccttttgcc tcgcactttc gcttctaaaa atttatgata ttcattgata   55800
aattcgctgc agtgttgttt gtaaggacaa acaggttttt tttttaacca ctcatcaaga   55860
gaagactagt aaaataaatt agacaaatcc aaacaaggaa cacaacgcaa cgactaaaaa   55920
gcagagggca gctccatgtg gctatcttta taagtgttga agcccaggct atagcattca   55980
agaaaataag caaggtagag accaatgtat agagttactt gggctgggtg tcttctattg   56040
cccttagaga tcagttctcc acccttggtc accagactgt ctgccccagg aggctcatct   56100
ttatggacta catcaaccgg ctctcttgcc ctcaagcttc cagtaagttt ggccaatggg   56160
```

```
gtgacccagc ggtatctaag ggaagcaatg aggagcacat ttaaggtatc tgtgttctgg   56220
ctccctctgt ggaatctttt ccagctggcc aagtccctca cttggaggtc acaggttctc   56280
ttcaggaggt catttccaag atttacttct tccctctcct tgccactttg ggcctagcaa   56340
gtcaacatag caattactag tcctaagtat ctgcactatg gtttctccca ttttgtggtg   56400
gtttcccttg actctatcca tacctttgta agtacttgtt ttactaaact ctccttaaat   56460
ctccctaatt tgagggtgcc atctgcttgc aactggaacc ctggttgaca caccaccatt   56520
tctgttttgt tgttattgct tttattgctt tttttttttt ttttcagaca gagtcttgct   56580
ctgtcaccca ggctggagtg cagtggcgcg atctcggctc actataagct ctgcctccca   56640
ggttcacgcc attctcctgc ctcagcctcc cgagcagctg ggactacagg tgcccaacac   56700
cacgcttggc taatttttg tattttagt agagacgggg tttcaccgtg ttagccagga   56760
tggtctcgat ctcctgacct cgtgatctgc ccaccttggc ctcccaaagt gctgggatta   56820
caggcttgag ccaccacgcc tggcctgtta ctgctttta agggaatac acacacacac   56880 acacacacac acacgtgcac acacatgcat gcttatatat ttagacggtc tctgggagta   56940
gatgcaagga catgagaatc aaacattatt tggccctgta aaggaaaat aaataggtag   57000 aaaactgagg ttgagaagca acttttatt tcatacccctt ctgttactt tgaattttct   57060 attattttc tgtacttaaa aatgttttc attataaatg agcaaatgca aggcagattc   57120
tgtcatggca gatgcatgca gctttcattc aagtgacagc cccacatagc ctctgggcac   57180
caggatcaga agtggagaaa caatacctaa taggagacc accatgtggg cagaaaataa   57240
agagataagc tcaaaagcat caattttcct tttcatgcac atgttttgt aatactaata   57300 tagtttttaa aacctgtcaa gaatgacata atcaatactc taaatctct tagagcagga   57360 aataattcta gtaaaatacc tagtacgggc cgggtgcggt ggctcacgcc tgtaatccca   57420
gtactataca cacacacaca cacacacaca cacacacaca cacacacaca catacatata   57480
tattttcaca ctgaaactac ctaccatctg gccaacaatt aaggatatca aatgtctggg   57540
atactctcca cacaacaaga catctaaaac aaacaccagg ttggtccta ccctcctatg   57600 gcttatattc tagtttgaga ggcaacatta acaacggcaa cctcatgtga atcagttact   57660
tgcctttaaa tgcaaacatg aggtcagaaa tggagacaga gctgatacgg gaagtgtgtg   57720
tgtgagtgtg tgtgtttatg catttatgtg tgtgatttcc tcatttggac ttgttcaact   57780
gagggaattt agctttgtag gtttgagttt cactagcatt ttggctcatg aatttagtag   57840
tttgctatga ttgctttaag aaaactgcat aaacataaat ttgtatttac caaacaaatt   57900
aagggattaa ggaatgatta cttgtgtctc aaatgaattc atccaatgag gtactttaaa   57960
ttgaaatctt ggctgtacct ttaaactcaa atttttttaa atgcaattta caaggaagtt   58020 ttttagtct tctacggaat gaaacaagct gtagctgaac ggaaaaataa ttggctttct   58080
ccagtgacaa acataaaata actgagctgg aatttcaatt gcatcctttc ctatttaaca   58140
cttaccagcc ccaatgaccc caaataaatc ctaaaaatgc atacttggtt ttcttgctttt  58200 cttgtatcat tgaagaatga agtacaattt gagtcccccc aacgcttgct gaattttcat   58260 ttattttct gtttttgtt tgttttgtt tttagtggca ggggacctct ctgagataca   58320
ggccacataa caggagacaa aatctaaaca tttaaatga ctcttgcagg tggaaatatc   58380
tacacattgt tgccaaaggc agtatttcag aattctagca cttgtgccat attcaaaaag   58440
ctgaaacaat tgtaactttc tcaatcatgc tctttcagct ctaataggac ccagtgaata   58500
aaacaaattt ctgaaagctg gggagaagca agcagtttat agtaaatact gtcatcaata   58560
```

```
catgaaattc ttaagttttt cattgataaa gctcacttta acagtgcctt tatctggcaa   58620
agactgactg cagggactat gagatgagtc aaaaaccaga atgtagggtt tggggctgag   58680
aagaacagga agccagttaa aaaagttaag ccatataaat gcaaatggta tattagatca   58740
agtgaaagag tagaatggag cactatttca tgaactctca aaataataac tttatgcctc   58800
tgctgagaag tgctttaaag ttggtacttt acctaaagtg acagcaactg agaaaacaat   58860
tctccctcag ttgacaggac ttggagtgct gtagcaacaa ggaaataatt tattattgaa   58920
aataaaagat gattaaataa ctctcttggt gatggtcaaa acattggtaa atggcacaga   58980
ctgatagagg caagataatg atacacgact gacggagttt tacaacattc caattcaact   59040
aaagtaattt gttacttacc agcaaaatta gtcaacctaa acgaaaatgt gctgctttct   59100
gacagccctc atatttaaac ccttgaggga aggggacag ataagacat ggtcctttcc   59160 tcaagatctt taagttcttc tagggaattt ttaaaaatgc acgaaatgat tttcatcaaa   59220
agagctttgg aaataaggat ggtctaaatg aagatgtgct ttttaattaa gttattcatt   59280
taggatttaa acaattcttt atctcaaagt actgaggcag cttaatggaa aatgcagaaa   59340
ctaacacaaa atctggtaag aacagatttt taaaagatag tgactattag agaatctgaa   59400
aaatcagccc ctgaaatgaa ccatttgcct caactaagca tgggatttgg tccgaatatc   59460
aatgttctgt gagagcagaa ttttcactga taaatttctc cgtggaggct tttgcttcag   59520 ttttcaaaa tatgctgcgg ggttcttgtg catgcctggt acctgaaagg ttttcaatt   59580 acagttttat taaacatgtg aaaatattgg tcaaaacaga tgatttccat attttctctg   59640
gaaaagggcc agagtactac catatttggg aaaggcatcc ctttaaaaag taatataacg   59700
aggtccaagg cgcttggttt ctaacaacca ataacttgg gcacagactg agaagctaaa   59760
gcagaaattg ctacagtggg tacaagagct ggatacagag cacagatgtg ttctgtttgg   59820
cctgaactct tttctttta aaatataaac caagttttaa aattcagaga tttcacatgc   59880
aaaactggtt ttctaattcc acttaaagaa ataaaaaga cttggaaaca gtgggcccac   59940
accatcccaa gacaacagtc agctgactgt gagctgagat gctcctcttg agaaagtctc   60000
tgtgtcctca aatttgcctc ctccctgaca ctccttcatg tcacctactc ccctgccagg   60060
cccctgtggc cacctgaatg tttacaatta atgattattt cacctgcaca ttcaattctc   60120
tcttctaata ttagggttta actagaatgc aaaaagtcat gatttaactc tctaatatga   60180
atatttttaa catgcatgta attctctaat gtgtataatc acatttcagt tcaaggccag   60240
aggacatcta ctttagaaat cagatctatg tgatgttaat aattattatt accatgatca   60300
tgatttatcg aatgcagacc aaatgcttag tccagtatta agtactgtga tgattatttc   60360
atttacttat cacaaccacc atgcaatttt gtcattaaca ttttatagat ggagaaatta   60420
agggtcaaag agatgaaata acttatcata tcatatcaat gagagaaagc aaataaaaga   60480
caaagccaat ggtgacacac aagccctcat ccttcctgat actccacaat gaaatagata   60540
ttccatcaaa aagtttaaga gtagaacttt acacacattc cagtacaagg caaagacaca   60600
ggtgtgacta ctaggagttg aagaaagtat acaaggggtg gggaagcaat aagtttctta   60660
gacaaaagct ttggttcttt gtaattactt cacttatttt aggagacata tataataagg   60720
tcagcttggt gaagcccaag agttttaagg taaaaacttg agtgtgaatt caggctctta   60780
catgtattag ctgtgggcca cttaacttct tgaaacctcc atttcctgat ttatgaaatc   60840
gtcccatgta ggatcatgat gaagagcaaa catgcttgaa gtacctgtga aaatcctcta   60900
gacagtaaaa aatgccacac aagcattcac ttgctagaaa ggtaacattc catgcaatgc   60960
```

```
tctctcacac caaagaaaat tgcaggaaac aaatgacaag ataagtatga gtttggtaaa    61020
tctattccta ctcatcaata gaatgtagca gtttgatgac ttctaaaaaa cctttcagga    61080
aatttgaatg aatagacaaa ttgaaatata ataattttt gttaccactg tgccctgatg     61140
ctttcaaata tacaatggaa tcaatcatcg ttacaataaa gttgccaaga gtgtttagga    61200
tctagaacca aataatctgg ttttgaaata ttgttcataa ccagcatagg tctggcaaac    61260
aggcagtaac ttgagaatcc agttcaattt tcaaatcctc tgcttactcc tgcacattta    61320
tcaggcgaga gctgatctac tttggctttg agacacttag tgtgttattt cgcaacatgc    61380
taataaaatt agtaagtttg acatgcagag atgggaaggc aatgatgtgt cttaagattg    61440
tggaattcta aaatattgaa ataaaatcat gtttggctta cttttcaagg aaataaaact    61500
gctgtacttt cattcacagc tgatgaagaa attacagaag aatatgggca acaacaattg    61560
tagtagattt ttaagtacct agttaaaaag tgttctgggc catccagata tatggaaagc    61620
aatattcctt aatcttctct cctggagctc atttgctcac gtaaaagtta attataaaac    61680
attgctatat gacttctact ggaggagaat tcaccatgct gggaatggca gcaggttgca    61740
gtggagaagg ctctgaatcg accatgaggg ggctttgagt tcaagggcaa ttacccaacc    61800
actctctgtg cctgttctcc aaccagtcaa acaaatgggt tggacatgat gaacttaaag    61860 gtcccttca ttttgaaaaa tgacacaaaa aggacagaaa gacacattca gattcacttt     61920
ggtttctaag ataacaccaa acactttgaa acttcccct tcatgttttt caagcagagg     61980
aagtaaaaaa aaaaaaaaaa aaaaagaaa gaagttgcaa gtattgttaa ggcttctaga     62040
aaggacaaca aagggcagga aatttgaaac aaaatctgag aatctgccct taaactgggc    62100
aattttgctt gttttctcac agtgcagtta gatgaaaaag tgtaaggttg atcttcgcct    62160
ttcctgggca ttactcattg ctgtcatgac cttgatgcaa tttgcagtaa acatcataaa    62220
ggtctctctt gtggtgagta gctgcaactt ttctgatgct acctcctgtg attaaaatat    62280
ctactcccgg cctggcacgg tggctcacgc ctgtaatccc agcactctgg taggccgagg    62340
tgggtgaatc acgaggtcaa gaaatcaaga ccatcctggc caatatggcg aaaccccgtc    62400
tctactaaaa atacaaaaat tagctagggc ttgatggtgc gtgcctgtag tcccagctac    62460
tcaggaggct gaggcaggag aatcacttga acccaggaga cagaggttgc agatggccaa    62520
gactgtgcca ctacattcca gccttacgac agagcaagac tctgtattta aaaaaaaaa    62580 aaaaaaaaaa aggctactcc tttccaagtc ctagcaatcc cactaaggtt ggtaacttag    62640
tctgtttggc tgccatacaa aatatgtgag actgggtgat ttataaagga cagaaatttt    62700
tcacagttct agaggctgac aagtccaaaa tcaaggcact ggcagttctg atgtctcgta    62760 agagcccct ttcctgcttc caagatggtg ctttgttgct gtgtcctcta gagaggacca     62820
gtactgtgtc atcacatagc agaaaatgga agggcaaaag gatccaggct ggttacctcc    62880
agccctttta tgtgggacta atccactcat gacttaatca cttcccccaa atctccgtct    62940
cttgatacca ccacaatggg gattaagttt caacataaat tttggagggg agacatcagc    63000
cacagtagtt ggtgagaaaa aaggacagta tttacataat gacagttgtc aatgggctgt    63060
ggaaaagtca agatagattc cagcagtgat tttaagatgg aaaatgagaa ccatgcacac    63120
agtcttcaag gtgcaatctt ccaacatagt tctggaacac agctggctcc ttccatccat    63180
ggggaatgac cacatttgtg tgctgaaata acatttagta ctagagataa aactggaata    63240
agtgatctaa acttttgaaat gttttgaatg acctttggct acaaagtcaa attataatgc    63300
tttctatttc ttaagacaac tctttatgga agttctagta tgtacctaac tttggcacct    63360
```

```
tagatttgcc ccacactgaa tcttatctat taaacctatc tcattctggg gtgagaaccc   63420
agatgtgtaa aatcgtatgg ccagaggtga ctgagaagtg cattttgact atgtttcata   63480 gtctttatc catcttagca taatctttt accagcacca gtggagttgt gaactcgctc     63540
aatttcttgt gatgtccagt gtaaaaatgt atgcctataa atgtaactct tagaaagaga   63600
agcaaaaatg agaaaccatg ggggaggagg ggaggaaatg acaagcacag tctgttttta   63660
ggacactgta cttgctgttc cctccaacta gaatgcgctt aacccagaga tctgccttct   63720
tcatcccgat ttcataccaa ttactgctca aatatcacat tatcaaagat gccattcttg   63780
acaaccgctt ctaaaattac aagcatctac cattgttctc agaccctcgc gctgtactta   63840
tctgctgaca tgttgataga atcttgttta ttagcttgta cacatggact ttaattcact   63900
ctgtattccc caaatctcaa acattggctg gcacacggtg gttggtactc tataaacact   63960
tggtgatggc tttcctatcc ctaagtcctc caaagccaag tttcatacct cttccttaag   64020
ttccaaagga aaccttatct gcagaaaatt aatgcatatt tgctgttgct ggataaagaa   64080
taaggatata gtcacagaga aaaaggaca tgttgaggcc aggtatggag ggtataaaca    64140
gttggtgaag agttttaagc tcaaggccta gcctgtctaa cttagcaata aaggaagtc    64200 agttctgaag tcaaagagag ttcttctttc cccactggga ggagctggtt catgaaagtg   64260
gagggccaga gccaagagaa ctctcccaag acacattgtt caaagtcaa gggcataatc    64320 tagatagagc tacacagtag ccatgaggac acatggattt ataaatttaa attaactaaa   64380
gttaaatgaa atcatacatt cagttccaag tcagaccagc cattttcaag tgcttaatag   64440
ccacatgtgg ccaggaatag acaggatact ttcatcattg cagaaagtcc tataggacaa   64500
cactgatcta aagaaattca aaaggacctg cgttcctcgg cttctgagga gatctgaaaa   64560
cgaaggccca gagggaaatg gaaggagaag cagggcagag cttgaaaagt aatcgcattg   64620
gaaagggccc tgactgctgg cttggatgcc ttgtgtaatt aaagttctat cccaacttct   64680
taaggaatga gtctcgtatt aaatgactgg ctgtctgtag tgtcactgct gaggtaggga   64740
gagaagacaa ttagggacaa ggagtagtgt tccatggaaa acacgttagc tatgagtggc   64800
agcagcaaaa ggtctcagaa gtgagagaaa tggacccaac taggtttgca acaagctgaa   64860
acctgtaaag gctcatgtca gctggcacaa cctctcaaaa tgcaaatccc tgagcccaag   64920
ataaatgtaa ggctcgtctg actcctaagg tatcaagtaa ttcttattaa gccccatttc   64980
aatgactgaa acctaatgca gagcccaggc acacagatta agtttccagt caaagcccac   65040
acaagcctaa agaaaggaaa ttaacatttt agagaaaaaa aaaaaaaaaa aaaaaaaac    65100 ccacaggctt tttcaaaggc ttttttttt ttttggagga tttaagtcac agcatgccaa    65160
ataaaggtga gtttctagga gaatacagca cagaggtgac caaggtgggt gaaatttatt   65220
cacaggggaa aatccaaatg ccttcaggga aaccacttt gcagggttct tctgataaat    65280
actgaaccca attaaaagca tcccttcagg gcaagttttc tcctaggaga tttctattgg   65340
ccgctttaac ttcccttcc ccagaatttc caggagaagt ttgtaacggt ttataatccc    65400
taccactcca tgctcataga ctttaagcat attttctcc cacaaggcag tactatttt    65460 ataatccttt taagattaaa actaaaaaca cagatgatta aaaaaaaaa aaaaggcct    65520 ggctgcatcc tcctacaata aagtattata attgcagtgc actactaagt agtatttcca   65580
caaacattag actatctggt ttccaggaca aagaaacagc ctataattcc aaagcacagg   65640
aatgaaaaag tacaagtaat ttaatctgtc ccactgtgat tataggtgct aagaaattac   65700
ctgaacggac ctctttggga cttgagaaga atggggactt taatgatgct ccataactgc   65760
```

```
cctattcatt atgataccca agagccacct gtggctattt aaattcaagt taactgaaat   65820
aaaaatatat ctatatttga aattcagttc cttatttgca cctgctacgt ttcaagccac   65880
atgtatcatc taagatggtc tcagacccac tgttcaatag aacttcctgc aaaggtgaaa   65940
atatcttata ccagtgctgt ccttaaacct taacacagcc caggtataag atattttcat   66000
ctctgcagaa agttctattg aacagtggat ctaagaccat cttagagaga taattacata   66060 attttttccca atttcataat agagattatg aagtaacagc ctccaaaata cagggttttt   66120
aggctactgg ctaccttcta cactcaggtg aacttttttgt agtggtttac acatgtgtac   66180
caattgccct catctcccca gtttcaagta cattaaaatg gcattagatg taataaaata   66240
catgccactg agactcagct caattgaaac ttgagtttct tcagaattcc aaacgatggt   66300
gcatctcttt ctgaaacctg aagtggggac ttgtcaggaa aatgtctatg agggaggcct   66360
aggaaaaaga aggcattttc caaaattaat aaatttatttt ccttgttttt tgtcacacct   66420
tattccagag gtgtctctag gctactgtgt gcggaacgag gtctggacag aacctaatga   66480
taaattgggg gatactgaaa gtcctggcac tctaaggagc ttccccacac atctttagat   66540
ttttatttcc catgtgggaa aaaagaaag ggatttccta tcttcccatc acaaactcct   66600
ggctttgcag tggttttatt acgtcattcc cctacttaca atctgccagt gactcagaga   66660
atttagccca aactggcact taaggctccc ataatctgat tacctttctg ctgaataact   66720 cctttttatca gaaacccttt gacctgataa ttgctggctt tcctaccacc aaaatttcta   66780
cctccctacc agatctatca ggtggatttt aaggtcaaga agagcatgcc caaggcagcc   66840
tgctcagccc ctggaaggag ttcagtgcct tcactgttgg ctgtgaggtt tacgtgatgg   66900
agggaagaga ctccaagaat ggtgtctgaa aggatgcctg gtgtctgatg ctgcccctca   66960
ggagtggtcc aaggtggttc aaatactgcc tgctttggcc atggctgaca gagctgaaga   67020
actgcctcta tatggtgtgt ggacacacac cccaggcagc cacttgccgg cttccctctg   67080
tttccttgaa ggaagtggag tagcatggcc ctggggctaa caagtgaaca atagtgcctg   67140
ccttaaatca tacccagcct ttcagaccca ggtcaagtgt tttctctttt ggaaaatcat   67200
ccattccccc cactaccagc cccaccaaga gtactctgcc tcctccggtt ttggttttta   67260
accatcttta ctgtgaggta tgcttttaga taggcctgta tttgctctgt tctgcagatg   67320
agtttccaaa accttctaaa accttgctca tatttgttat gctggattta aagtcaacag   67380
atgggagttt tcaacccagt aaatggaatt tctttgctgt gggaaatcaa gtactttgac   67440
ctctctggtg aaattcttca tttgtaacct cactgggtta ggctagatta gtgtttctca   67500
acatggttcc acatcggaat catctgggga tcttttaaaa caataatgat gccaaagtcc   67560
taccccaggg caatgagtca gaacttctag gtgcttggct caggctttgg aattcttttta   67620 gaagttcgca ggtgatccta acgtgcagcc agggttagaa aaataaactg agttcaggaa   67680
gggacttatg ctacatggac tggagaattc aataggaaaa aatgtagtag ttagagatgg   67740
ggcatggtag tactgacag aggcagtcag gcccataggt gttgcttctc atctttgcct   67800
tgagctgtaa ctagaaaaac tgcaaactgc attataacca gaacattatt atatacatat   67860
acatgtacaa tcaagcccaa cccaattaat tttctcatat gactcaaact ctagtaccat   67920
ttggagatga ggcaggaatc ataaacataa ttggctgcag gcatttagt tgccattgta   67980 taaattcttc ctgaaaaata attttagatt aattttttaag tgtggatttt acaatttcct   68040
atctttttaa agggtgggaa tcctttgcca attcccaaga ggacaataag cttaaaggaa   68100
gataatgtct gaaagatctg aggaccaagt ttcctgagaa agctgtattt ctaaagtttt   68160
```

```
gaccctacaa ggcaacatta aaagtaagtt caaggaaaca aatgtgagaa agcatatctc   68220
cctttagata acctagcaaa gaagttaaga agggaaatag ttccttagat cagaattaac   68280
agttgtggat agccttccct tcagaaaatt gcaatgctaa acagacgtta cacaagcaat   68340
atatccctgc aacttaattt ctcttcctag gatctttaat attttctttt ttttattcca   68400
ttaaacaaat atatattgag catcaccttat ccaccagatc tgaagaaaca ctatttttaa   68460
tatgttcaaa atttgagtct tttcttgata caataacatc tgccttaaca ggaatcagta   68520
tgtaaaaatt acagttttta aagaattata taaaaggtat tattccagaa gacttgctat   68580
ggaatccctt ttaaaaaggg cgttcagaaa aaggtaacac tgaaatttat tacagtttga   68640
agaaaatcac tccaattata aatccatgaa cccagtcatt gtttaatgaa gctcatcttt   68700
gctggaaaat ccccactgag aacaaagcat cacaatgatc cacacagtcc taatcaagcc   68760
cactggaaaa atcaccctga agaacactgg tggaaaacag aaagaagtcc acaccacagt   68820
gtgagagcta atttaatgtg ttcttcaaga aaaattaaat aaaacaatat gactcaattt   68880
ttcttttatg ttgcaagaaa aataacattt atataaagct agtagtagaa aagcagaagt   68940
atagcttagc tttctatgat ggcaagtgaa atagtttctg ctaatcaaag tgattctttt   69000
ttttttttcc tttgagacgg agtcttgctc tgtcgccagg ctggagtgca gtggcacgat   69060
ctcagctcac tgcaacctcc gcctcccagg ttcaagtgat tccttgcct cagcctcccg    69120 aatagctggg actagaggca cgtgccacca cgcccagtta attttgtat ttttagtaga    69180 gacgggtttt caccatgttg gccaggatgg tctcaatctc ttaacctcgt gatctgccct   69240
cctcggcctc ccaaagatcc gggattacag gtgtgagcca ccgtgcctgg ccatcaaagt   69300
gattcttagc cattttcttt gaaaatgtca gtcatagagg taggctctgt tgctcttcaa   69360 tgtataccctt cttttatata aaagcaattt gactaaatat tagatgtctg tgtgagtcgt   69420
gttctgctac tcaaaacact tcttgttctg ttccttctcta tattttgttt atttgtttgt   69480
tttttgagat ggaatcttgg tctgttgccc aggctggagt gcaatggcat gatctcggct   69540
cactgcaacc tccacctcct gggttcaagc gattctcctg cctcagcctc ccgagtagct   69600
gtgattacag gcgcccgcca ccatgcccag ctaattttg tatttttag tagagatagg    69660 gtttcaccat gttggtcagg ctggtcttga actcttgacc tcaggtgatc cacctacctt   69720
ggcctcacaa agtgctggga ttacaggcat gagccacagc gcccaacctc ttctctgtat   69780
gtttattcag acattcatgt ttaagaattt ctgagaaagg aagccaaaga taataatacc   69840
tgacctctat gtctatatga tgaagaagtg cacttcctat gtaaagatgc ccgtattcct   69900
gattaggtta agcaacttga agttctagtg aggggcaaaa ctacaggact gcagaaactg   69960
gcatagcctt ttacacatgg cagcatttgt ctactgataa tggtgacaca acctccaaga   70020
gggcagacca cacggtgtat taagagaaag ctgtccccat aagaaaaggg gaaagtaaa    70080 atgactcatt acatagtttg aaatctctta tgatgggtgg acaaaaccct caaagaagaa   70140
attctccagt cttaaattgg cttttaatg ttcgaggcaa gaacaagtct cctgatgagt    70200
acactgccat cgcctctta acaatttagc tatgaaaata tgaaaatacg aggagactat    70260
agatttttat cttagatta cttcaaaatt aagcagtgag ggagcatgac taaaaataga    70320
aaaatgatga aaagattaat taatgatact ttactatgtc tcagtggatg gcagtcctta   70380
ttacagctgg ggcagatgat ttcatctttc tgggcctcca tttccacatc tgtaaaacag   70440
gataattata tccatctcag agagctgttt ttaaaattac agatgacagg aaagtgaaac   70500
tgttttgaaa ataatgaagc tttctattac tgtgagatta ttaaaagatt attataacta   70560
```

```
gacatggtca atatgttttc ttcaaagtta tcagactaga catttttccc tctggtgatc    70620
tttcacccat atgtctcaat catactgaaa ttattcaaat cacttctttt ttctgttttc    70680
ctggtactag tttctctttt tcttttttctt tttcctttct cttttttttt tttttttttt    70740 tttttttttga gacaaagtct cgctctgttg cccaggctgg agtgcagtgg tgcgatatcg    70800
gatcactgca accactgtct cctgggttca agtgattctc ctggctcagc ttcctgagta    70860
gctgggatta taggcgtgtc ccaccactcc tagctaattt ttgtattttt agtaaagaca    70920
gggtttcacc atgttggtca ggctggtctc aaactcctga cctcgtgatc cgcctgcctc    70980
ggcctcccaa agtgctggga ttacaggcct gagccattgc actggctggt actagttttc    71040
tatctgcctg aagaagtacg caaatgacta ttttcatgac tttttttttt gcctttaata    71100
ttatttaaca gctattttaa caatgaaaga cattttacat attctcaaaa ggtatgtacc    71160
aaagaagggt gtgggcagaa atgttcacaa aatcaggacc tttcattgca tcttggtgac    71220
caccaataaa gtacacagaa acccatagtg aactgaggtc taagtggctg ctatcaacca    71280
acacaatctt gaactgctga gtctgatcat ttcattttct taaaacttca ggacagttca    71340
atttagagag cacaagagtg aagttagcct ccctggtcat ctaaagcaac atgggaaggt    71400
aatttaagaa aagtgacacc atatcaatca ctttcccaag cttttcaggg gctcactcca    71460
aagactttct tgatgataaa ttttattaaa gtgctgatca taatcaaaac agtacattgt    71520
atcagaggtc aagcattgtt tttcacttcc cttcccagaa cttattaaag atgtacctct    71580
gaagaaagac ataaggaaga acaaaattgt tttgactcac agaaaatggc ttacacagac    71640
atctaatact tagtcaagtt gcttatatat atgaaataag ttataccttg ggagtaacaa    71700
agccaatagg cttggctcat aggggggctaa ctacggctgc agcagttatt caagaagtta    71760
acatattctc tcctgtcccc tgaagacacc acaggcatct cagtaataaa ctgataacaa    71820
ccaatactca agagtttgtg aaaatgcttt gtaaagtgct gaataatgta agtgattatc    71880
tacttaccac aaacgtcctc accaacatca tcattaaaat cttgaaagat aagtgctttt    71940
cagtagtttt gagagtgaac caatgacatg ctaaattaaa agcattatat ttcaaccatt    72000
tccaataagt gccacagaat attaagactt aagaatatta aaattctggt caggtgcagt    72060
ggcccatgcc tgtaatccca gcactttggg aagccgagga gggtggattg cctgaggtca    72120
gaagttcaag agcagcatgg ccaacatggc aaaaccctgt ctctactaaa aatacaaaaa    72180
ttagccaggt gtggtagtgg gcacctacaa tcccagctac tcgggaggct gaggcaggag    72240
aataacttga acccaggagg cagaggttgc agtgagctga ggtcgtgcca ttgtactcca    72300
gcctgggtga agaacaaa actctgtctc aaaaaaaaaa aaaaaaaag aatattaaaa    72360 ttcttatttc atctcctttt cctctataga tagagcaggt agggcactac cagtccaaat    72420
ctatgtaatg tgatgtcagt ggtagctcca gaattcccat agaggagtgg ctacatgggt    72480
gatgatctgg ctgaaaggga ggcaggcaac acagctggaa gctgtgcttg cacaagagaa    72540
cactacttgt ggtacctaga ctgcatgttt attcaggatg gatggggact atggtggacg    72600
agaaggctga aggccaaatt caagaccatc cttagaaacc cactcctatt aagcacccag    72660
gtaagaaagg cctcatattt aagtctcctt agcatgtatc attttaacag ggctttccaa    72720
aaagtacaac caggggtcac ctttgcaata tgggattatt taccctcagg taggtagaag    72780
agtatcttca gccactcttc attgcaccaa gacccttca gccatcccta ttccagcaat    72840
cccaatgact gaaatcatct atgactcata aagagaaaag gcaggagtga caaaaaattg    72900
tcctgcgtga gatggtgtga tttactttat gactttgcct ggtctctata gtcataatgc    72960
```

```
attgagcctt ctgcaaaaga ttcacacatg agagaataaa tgaatcaaag gcagagccag   73020
tgatggatgg aaaattaacc ttaacaccca cacaccacag ctccccaaaa ttcacagaaa   73080
ctaaagactg cagacagagc aagtctccac tgtaaagaac aatttacaca aagcagatca   73140
tacgagattt tccataagcc tatggttctg tcaaacaata ctacaggtgg ctttaagcca   73200
ttgacattta cacttggtgg tgaaaagcca tctgggagaa aaaaaaatag cactccccgc   73260
cttggatcta aaagcaagtt tcctcggcct ttaaaagcaa tgaattccaa acagcaacaa   73320
acaaaacaca taaacagaat tagtgagaat ctgtgctaag agctatggca aaatcagaca   73380
gaagtttctc cctcaaagag ttttcattct agtaagagtt ttgttttgtt ttgtttgttt   73440
tgagacagag tctcactctg tcgcctaggc tggagtgcag tggcgcgatc tcggctcact   73500
gcaaactccg cctcccaggt tcacgccatt ctcctgcctc agcctcccga gtagctggga   73560
ctacaggcac cgccaccac gcccagctaa ttttttgtac ttttagtaga cagggttt   73620 catcgtgtta gcgaggatgg tctcgatctc ctgacttcgt gatccgcccg cctcggcctc   73680
ccaaagtgct gggattacag gcataagcca ccacgcctgg ctagtaaaat agtttaaaac   73740
acacagagac agcacaggta gcttggcaaa caaggtcata tgaatgagaa tgcaaggctt   73800
gtcggagagg ctatgggcag gaaaaggaat cacagtggga tggataatca aggaaggccc   73860
actagaaaaa gtaacattta gaccaggcgt tatttcaaag ggtggagccg ttgtaggca   73920 caaatagaga atggtaaaac ttgggggag gtggtggaga atggtcacaa gctaggaaat   73980
ttgtaagcaa aaaggatgtg tgaggcagct gggttcaagt ggaaccaggg catgaggat   74040 gtgaagggtg aatagatga tgggcaagag gtttggcttc atctgtgcac gtagtcatca   74100
aactggtcct gtgtcccatc agcacaaggc actctcttag gagccaaggg acactgaggc   74160
agcccccatg ctcaaagaga aagggaaggc catgtgatga tctaggattc ataaaatcca   74220
tggaaggctt tctaacagag gccagctatt caaaatgcca tctggggga gatttaactg   74280 agggcaatgc ctgtgttatt gacagagaaa gaacaaaggg tgtccataag cagagaccaa   74340
ttaggtgatt tttacagatg acaaatataa gagttcaggt ttgtgttacg gtagcataat   74400
tcaagggcaa aaataaaacc aaatggttat agattttgcg taacttttct gatggataac   74460
ttaagatttg atgcaacagg aatcaccatg agatatgagt tgcaatggaa agttttatg   74520 tttttttttc ttgccaagta tagttcagat gtcaaaggca aagaaaaaaa agtcagaaaa   74580
taaaattatt tggaaacatc agaaactgct tgtaaggact ggttattgtg gctactgtta   74640
attaagagca ttaataactg acagggaccc ataattctgg aagacaaaag taactaagtc   74700
acaaaaagct gccttatgat attaaaataa aggagcaaat caatgaaaaa gcctacagtg   74760
gcactctcag aaaagtctaa aacaaatgtt gagcaattca agagaaattt attgggtctt   74820
cactgagcat cagacaaata agttcctcaa gacaaaagag gattaaaaaa tgttgaagag   74880
taaaaccact tcctgaaaac ctgtcatcga atcattaatt tattgggtac ctactttgta   74940
tagagcagag tgctacctat tttaagaaat gctgtggtat aatagctcca gaatgaatta   75000
gggcctacat atgtcaaggc aatctgtgag taaatgccta atgaggtaaa catgattaat   75060
gcagtgagtt cgatatagaa atgggtcctt ggggccggac acgatggctc gtgcctgtaa   75120
tcccagcact ttgggaggcc gaggcgggcg gatcacgagg tcaggagttt gagaccagcc   75180
tgaccaacat ggtgaaaccg tgtctctact aaaaatacaa caacaacaaa attagtcaag   75240
tgtgttggtg cacacctgta atcccagcta ctcaggaggc tgaagcagga gaatcgcttg   75300
aacccaggag gcagaggttg cagcgagccg agattgcgcc actgtacacc agcctgggca   75360
```

```
acagagcgag attccatctc aaaaaaaaaa aaaaaacaag aaagaaaaaa gaaatgggtc   75420
cttgggttct acagttcacc atggtcaagg gatggacaat cagtggacaa aagactcatg   75480
aaggatgact ggggaaacag actggttaaa aactgactca tttagttgac ttgctaccag   75540
tgccttctgt cttctgctag ctttagttaa aacggcttag gaagagtcaa aagactctca   75600
taaaactaag ccaactcttc cttgaattct cctcttcttt attgacagaa acaagcctga   75660
tgtgatccac taaaaccact gcagatcatt tggctactct ttggaacatg ctttaatgct   75720
attacagcag tgttttttcaa actgctatgt gtacaggaat cacctgggga ccttgtgaaa   75780
gtgtacattc tgttgcagta ggtctgggga gaggacccac aatcctcatt tccaataaat   75840
tctcagtgat gccagacctc ctgtaagcgg caaggtatta gaacatcttc agttgctgtt   75900
atcagaagat gataggaaac catcattttc ggggtcagaa tgctggagct caagctttgg   75960
gccttgatgc atataataac tcataaaatg taatattcag gaaggaatga ggctcctaaa   76020
gaagtgagaa agtagaatga acaaaggcct aagagaatag aaatgtattc taacaatata   76080
aattataaaa ataaaagtaa gagtgcccag gggtattgag attgttagat tattttataa   76140
tgatataact taagggattc caaaataatg aacataaaat gttattatta gattttttttc   76200 cttttcacat acttgaagga caaattatat catattgtct tttttcttc cccaatacta   76260 tgagcgttag agaatgagac gcaaatccga tatgtagtaa caaggtagtc actcacagca   76320
aaagttgaaa gattcctagt ctacgctaac aagtgtctgc aaactctaca gaaatgcaat   76380
tagaggttgc ggcagctact cccctgccta aaacagcagt ctgaaaactg ccaatctgtt   76440
gcaaattctg tcttttctga gaatatttta agaaagtgg tagagaaata tttgaaaggc   76500
aacagaacac taattatatc tagacaagtt tccttttttt tttttcccaa aaaatatgaa   76560
agttccttta ggctttacat ctcctaggca tagcaaagca tttcataact ttctacctta   76620
ggaaaaattt tcacagacat tttaaccaat tcagaggaag gggagaatga aaataccata   76680
attaaccaaa gaggaataat attaccacca aaaccaagta agccttttat ttaggaagga   76740
gtgagctcta gctgaagtaa acatgctatt tagtcaggat gtatgctcag acacctgtag   76800
tcggaaattt tcaaaatagc tatggttttt tttcttctct tttttttaata gtagtcatct   76860 ccaatgaaca ccagtggaag tctgtggtat ttctcagttc tgacctgtca tgacttttgt   76920
tagttttcta ttttgattag ctaaagattt tctaactcaa cttcaatgat ttattctact   76980
aacaaaatag tacagggata acaaagaatg aaatgtttca gaagagaaaa tactggaaat   77040
cttatttagt ccaattcttg tcactgtata gaaggaaaat gagccccagt gggaagaaag   77100
acagcctggt cacccagaca cctagattcc tggtacaaca taccttagtc tttaccagct   77160
gtctcctagg tagagtcctt ctaatctcaa actaagggtc agagctaggt tatctttcat   77220
ccaagatgaa ggtttgtgat aattacatct ttgcaacttc ttttctactt ggcatggggc   77280
tctaaagtag gaaaatgatg aagggtttag ctaaacctgg aggaaaaata ttttggtttt   77340
gtgaaataac aatgcagatt tcagtctctg tttgcaatgg ggggaaggag gaagaggcat   77400
tttttaacat ttattttcta aaccaacaaa caaatcctac cattagtcaa agactcaggt   77460
ctttggaatc tgaagcttgt aaatttcagg ggcactcttt aagaagaaga atacaaaatt   77520 aagaatataag tgaatataaa attaagaata aagtgaatat ttatttagaa ttaaaatggc   77580
atacaggccg ggtgcagtgg cttacacctg taatcctaac actttgggag gcagaggtgg   77640
acaggttcct ctgagcccca gtgttcaaga ccagacttgg tacatagtaa gacaccatct   77700
ctacaaaaat taaaaaacaa caaaaaacaa aaaactggcc ggtcttggtg gtgcatgcct   77760
```

```
ttagtccgag ctactctaga ggactgcttg aacctaggac tccaaggctg cagtgagtta   77820
tgattatgca actgctttcc agactgagtg acagaatgag atctcatctc tggaaaaaaa   77880
attttaaata gtatcataca aacaacaaat ttttaaaagc tataaatact acaaatatga   77940 agtgttttaaa aaacaaatat ttttattaac tgattgccat acctctgaaa taattctcct   78000 atatttttttg gttgcacact ctttgatcat ctcttccaat aacatttttgc aatattctct   78060 attgagagaa tagaaaaata attcagtctt ccctttagaa atgtagatca gaatttgtaa   78120
tttattcttg aataatttgg aaaagttcct ttcagcttca taattcatta caggtaatgt   78180
catataaatt tttttggattg acttcaaatt tggaaaactt ttatcaggtt tcttttatat   78240
gtgagctgta agattcaggg cactgcaaga tttcgtagta tttgacttga tgacacttgt   78300
taaccacatt gccagggcct ctcctagagc caggagatgg acctatacca gggtataggt   78360
agccttgaag gttaagttca agcacttcac agtaaatcca cctgagcctg catttatat   78420 cctcaacata tttgatgcat ctgtgaagtc tcccagtcct ttcaaataaa gtgcctgttt   78480
tactcagaat acctaaactt cctgatggca taattgttcc atgattcagc caagactgta   78540
tcacttgagg tatacacttc atttttccat tgagatcaca agacaggcat gatgtttgac   78600
tacctggtgt ataaaccgag tgttatttta ttacactaag aaaatgcaat gggataatat   78660
atgaagaatg ctaaaacact agaaaaatgt tggatattat tatttctctt aacctctagt   78720
cttccaacac ccatgctata atggacaagt agtttatgtc aattaaggca gactagtctc   78780
agtacagtat aacaattagg aatctagatc cccaaaccag accatcttgg ttccaacccc   78840
agcctaatca ttttctaact aggtggactt aggcaaattt attgactctg gaggatttat   78900
aataagcata atataaccta ccttctaaag ttgttttgag ggttaataca cctgaagtac   78960
tcagcatgat ccgtgcagta gcaagacctc aataagtggt agctactatg attattggga   79020
aattagtcca tgaagtctct tgagaaaagc tacaggggaa ataagcccaa tttcatttcc   79080
ctatgtagaa aagtttgcag gatttgggcg tgacaggtag tcatccacaa agcagcagtg   79140
ttatcgcccc ataggaaatg aagacttcgt aatgatttat actttaataa agagctgctg   79200
cagcatatac tgaaaatatg cacccaaccc atatcttctt tcaaaggcat tcatgttggt   79260
tcaaccaaat ccctagttct ctaaaatgaa gttttgacaa tcttatatct tctaaagcac   79320
tgagaagcct ttttccttgt tttctttaaa gaggcttgag aagaaccaag cctttttttg   79380
gttcaaataa aatatttaca ataggaggaa aaaacattca gataaacttc accttgcccg   79440
cctggtggtc tctcaataca cagaagaaat gcaactaggg cactaggaaa tctaaaaaaa   79500
aaaaaaaaaa aaggaaagaa aaaagtata gagctaaagt tcacttcagg acaacgcaaa   79560
ctaagaaaaa ctacatttcc caaggaaat agagcactat gtctacaaag taactcattt   79620
tttctttaat gttcaatgtt gtctattcca gggaaaaaat ggtacaatta accaaaactt   79680
atttctaccc aacatctctg caaaggaatg ttgctgctgc agatccaccc ccaacatggg   79740
aaggcccaag gcaagtgagc aaatagaggc ccatgtacca taagtcaaaa catttaaagt   79800
tacaaatcaa gctagcaaac tgctcaataa aataggtgtt atccttctac ctagactgac   79860
aaatatatct tttcaatgtc ttggaagacc aggtacaact ttagaactcc tacaatgttc   79920
atagtccttc cacagaaatg ggtggtttaa agagagacat catcctgagc cctggtaatc   79980
aatttgcctt cctccccccct gcctgctcca tcctacatca agaggggcct tgtgatatgt   80040
ggacacccaa gctcgctctc tgtctctctc tctctttctc tctctctctc tctctctctc   80100
tcacatacag acacacacac acacagagct atcccttaaa caaccctcgt gcagagattg   80160
```

```
cacaaccagt agcaatgaca gccttcagga agatggcttc aaggatccat gcaaactgca    80220
gataccagtt cagggccttc tggacagcga atgtgggttc ccacataacc aaatcatggt    80280
ctaaaaatga aaagagagta agactggaag gcccaaaagt cacctcaccc cataggcatg    80340
gctctgacca gagaagaatg acagcagagt accatctaag gcccaggaca gaggccagtt    80400
gtgttcatat actaggtcta tattttagtt gtagagctga aaaaaattgg aggaaaatat    80460
tccctcagaa aagagaagaa aaaaaaaaaa aaaaagagc tgcatgtctt gacctttccc    80520
agatagaatc tccccagtca taggtacggg ccctgaagct aaatctcatc taataatgat    80580
agcttcaaac ctacaaacaa aacacagatg ctagggaacc cttaagagtc taagcaggag    80640
gccataagta gactaaactg actacaccca agaggatagt tgctacttgt tgggtgctaa    80700
gacctagaaa gctgactgtg gcaagtaaaa ggcagaagta ctcctgatgt aatgggtgag    80760
gaagagaatc ttaacctcct ataagttttc aaattgtccc cttcaaaagt caaactgtcc    80820
ccttcttctt tgttatgttg gataaagtcg gctcttcttg ccctcatcag cagttgtaca    80880
cgattgtaca caaatgattg tcctacacac tcaaaatttg gggtttacaa tacacatctt    80940
tgcaaatggg gtatgtccaa ctgctataag tggccaaacc acaggtcacc caccatgagt    81000
cctaccacta agacaccatt gtcaaactgt gggctgtaga gtttccttat gcaaagaaac    81060
tctgccttat cttgattttc tgtggtacaa atgtagtcag gaaggaggca gataatgcaa    81120
gcaaaccaaa tcaattaaat caggagcact gaactgatga cattagatgg taagcttccc    81180
ctctctcaaa tctgatatcc attcacccct cttcagcctc cctcccaaca cacgcataca    81240
cacatagaga ccacacgaaa gaacctagca gcatgcaagc acaagaagct tgggccacac    81300
actcatacat gcacccaggc aaaactccag agagaccctg agcaggatcc atctttccat    81360
ccataaaata aagataataa aacttatctt ggagatttct tcctaggatt aaatgagata    81420
cataatatca gtggctgtc tcagggtagg ttctcaaatg ttaattgtct ttctcttcct    81480
tctccctgag atgagacaat ttgcctgtcc agcattccaa acccttggc atgccaagca    81540
aagaagtatg agtcattatc ttgcctcagt cacaagcaac aagtacctgt ggagcaaaat    81600
attaccagga aagtagagag tgcaaaagaa gcggtgagca ttcttgctgc gaatgcatat    81660
ctgttctact gaaaatcata acttaaatct gctgaagttg tacataagga cctggagggt    81720
agaagctaac aaggtaacag agttatgctt ttatgtggaa cttggccaaa taatgccatg    81780
ctgtagccag gaagtatgtt tcccctgcac cctatttaaa actgctttgg tggtttgcat    81840
cagacctaaa taatatccac gctactctag agtaggcagt ggtggctaca agaccacact    81900
tcccttcaac caacgctgct tcacccttat aaaccaaaac ataaacccca atgaaaaaag    81960
aaacttaaaa aataaattta gattttagca cttcattcgt aataaaattc tctttccgac    82020
acccttctat gaaaaaaaaa aaaaagagga atcagtatct actggataat tcctctggtg    82080
actttattta aaattttgca gtggctttca aggccctaca ctgattcaaa atttatggct    82140
aaaggaattg catgaaaact tctagcagct ttccatcatg tttgtcagaa gttgaaacat    82200
cttttccat atttcatgag aatacaagaa ccaattccat acttcaaaaa cagtcaaatt    82260
acttattgtg atcagaacta aaactattct aactgaaagt aaagatttta ctatttggac    82320
caaacaccta acaaacagtg actgcttagt taaatgctcg acctcagttg cattagatac    82380
agtaggatga agtggaggct cagctcagca cttcctgggt gctaaatgat gtgtcaggca    82440
ctgccagaga tcccagagat agaaaactga ataagattga gaggattaaa ggtataatgg    82500
gcaagagagt tacgtaaaga tatgactttg gcttggtatt gttaccagct aagtgagagg    82560
```

```
tctgtatctc ataggagaca tttacctcaa actgggacat tcaaagcagg tttcctcaag   82620
aagatgacac ttgaactacg tcttaaaaga tgagtgaaaa ttagccaggt agcaggagtt   82680
ccagacatcc tgaacaaagg aacagctgcc taaattgctc acattgtgtg tatgtgtagt   82740
gacacaaata gactgggaaa atgtgggctg tggtgggatg tgaagcagca gagtcaaatg   82800
ggaaccaggt cagaggcccc tggtaagccc aattaaggag ttaatagtaa taacagaagc   82860
tgatatttat tgagcattta ctatgttgca ggcaccatgt taaatacttt aaaacaatat   82920
tttatttaat cctcaccata actccataat cctcatttta caaatgagac cagggatgac   82980
tagtaggtaa agcaactaca acaggctaca cagccagtac atggcaagtg ggtctggaac   83040
ccaggacggc ctgattccaa agtttatacc ctacactctt ctaccaccag cctatcctca   83100
aagagagcac taaatgaacg cattgggtcc atcatgctgg ctatggaatg gagaatgcaa   83160
ttaaaggctg cccaactggg gctccgtgac aaggcaggga taggaaagag acaacaaatt   83220
gattcaaaaa tacattcaat gggacctaga aggaaacatt caacatgcac atcctcctag   83280
tgcatacaac aacaaaaaaa aatgaggctt ttgaaaatga ggtgtagaaa ataaaacacc   83340
agtattccat aatgctttca aatataaaca gttaaaacac gtatccttt  ctttacttat   83400 aacatgctcc cagctgttaa attcaatggc aaagaccagg tctgtcttat tcatctgaga   83460
tggtatccca ggtctgagca tcctgcctgg caagagatac tcaataaata tggttgaaaa   83520
ggtagaagaa aaaatgccca gttttttgcaa tgatatcaga ggtgccttat tgatccagag   83580
ttaaaaacta accttactga aaaaattaaa aagtcatgtt cataactgag tagaaaacat   83640
gtagtagtta tgttgactac atagacaaca gtcatcatta gggaatgcta cattgaaaag   83700
aaggcaatga gttcaaaatg tgattagtat tttgtataaa tcataactca ttaaaaataa   83760
gatgttgagt ggcctaaagg tggaaatgtg tttttatgag gcggaaaaaa agcacgagta   83820
gactgaagat cagatttggg gcctaatgat gtctagtctc ttaccctgac aaaataagca   83880
ggttattaaa gtgatgtgaa gaacctgatc actatgacac ttttacaaat tctttgtcct   83940
caataagaat ctatctactt ccaggaacct gaaaagtcat attttttcaga cctgaagagt   84000 tattgtgcac tttacagttt tccccaaaag agtcatttct taattttgat catttaggaa   84060
gagtgaatct attaagtcaa aaacgaagaa aaaaaaactt tctatttctt agtgaaattt   84120
gttcttttat ttaaatcctt tgcatactac taaacagaag tacagaagct actaaacaga   84180
agacagattt ttgggccttt ttaggtgacg taaaaggagc ttgttgttta ttaaacaatc   84240
tcattacctg atatattatc ttgcattaag atattttgaa aaaatgtttt cagtttacca   84300
attacgttag agaaattctg aaactatttta cttacatgaa aaattaaaat gtaagtagaa   84360
ttaggtttct cgtcttcaat atatctgtct tcaaccattg gccaactttg aaaatttaat   84420
ttgaatcaaa tgaatacaaa ttcaaaatga ttcattaatt caaccatttt gaaacttcag   84480
ttctataaaa atatgaaatc tgtgggcctt gtaaaactgt ctaaatacccc aaataaaaag   84540 ccaccacgtt tttaagctaa ttgttttaaaa gtgtgtatat tgatgaaatg aaagtgactc   84600
gtgaactatt gggtctggaa tttgcaaatc ataaccttta tccttgtaaa cagaacctaa   84660
ctaacaacat cagggcctgc taatttcctt ctttttataat ctggaacaaa agttgtaatg   84720
atttttaaca tccacagaaa attaagggtg ccattttaaa tatttattag caaaatgtca   84780
cttaggtttt aaaagtctgg aggaaaatga gagacaattg aacattctgg tactgcaatg   84840
caggaaaaac gccaagaacg aaacactaag attttattaa aaccatagga ctcaaatgtg   84900
tgtcaagact ttttgcttgc aatagtgcct cttcctaatt tgattaaaag cttccatctc   84960
```

```
catgccacct tcaatgtatg ccataatttt taaaaagttc ccaatccact tcaaacactc   85020
taaaatttac aactgaccgt gatgcgcatt ttttctagac aaacctaaag gtaaatctgc   85080
ccatgtccct ggataaataa aatgagtgcc tccgggtgat gtggactgtc aactcctcta   85140
catttcatcc aaagtctaca tgggtcatct ccaagtcacc agaagagcca ggggaaagga   85200
ggggaggggc acgatacgta agatgttaaa catgaagatg atgtaaaatt acccagattc   85260
aagctggcca ttttacagat gaggaaacta aggcccagaa aaagctctat gacttgccca   85320
aatactcggt tacccagacc acagctgcag atactgttat ttggatcata gctgcaaaaa   85380
gtctaacttt tggccgggcg cggtggctca cgcctgtaat cccagcactt tgggaggcca   85440
aggtgggcgg atcacgaggt caagagatcg agaccaccct ggccaatatg gtgaaacccc   85500
gtctctacta aaaatacaaa aattagctgg gcgtggtggc acgcgcctgt aatcccagct   85560
actcgggagg ctaaggcagg agaatcgctt gaacccagag gcaaagttgc agtgagccga   85620
gattgcgcca ctgcactcca gcctggtgac agagcgagac tccgtctcca aaaaaaaaaa   85680
atctaacttt tgaagtctca gaggttttac actttccata acaaatagtt aagaaccccc   85740
attcctgcat gcatatatat attaatatta tatatattta tatatataat tatatatata   85800
tttatatata tataatatat atatatattt ttttatttt attttttcct taaaaacctt   85860
cagagacagc gatcaggtgg gtagcctagt taggatttta acccttcggt ttccaacaaa   85920
cgataattgc atagaaccat caactccctg aagacaggac tatcttgttc caggcaaaat   85980
ctacagcctc tagcacccag taggcattca gtgagggatt ctcggtttca cctgagcatc   86040
tccactccct atccatccat gccaaggcgt cagtggagcc agctaacttt cttttggaaa   86100
tcgattattt tcttgaaact tgtttccaaa aactccgggc caagaagccg gcctgaggga   86160
aagcgtggcc gtctccagga gctaaggact gaggagctgg cctttgaac gggtggctca   86220 gaaagagctg ggtgggcacg cggcatcgcc atgggcggag tggcccaggt gcgctggctg   86280 cttttggcagc tcaggctgcc gctccgggcc gctgctcccc ggccgccttc agataaccaa   86340
cttctcaaac ttcccttcc gggggtgggg gctcgcctcg aacgcggcca acacaacgcc   86400
tttcctgctc gcacaaaggg gaccaaacgt gccccgcgcc ccttgcaact gaactttcct   86460 tctcttttc aagaaaaact cacaatccct gcagctacgg gagtcgggct gcgtgagtgt   86520
cgcgggggaa actttcctcg tttccgcccg ggggccgggt gccgggccc gactgtcaag   86580 cgcagcggag aggcggggac cccaggaaga cccccggcgc cccgccgagc ccgggctggg   86640
gaccactcac ccgacttctg aacgtgcggt gggatcgtgc tggcgatacg cgtccacagg   86700
acgatgtgca gcggccacag gcccctgagc agccccccgac ccatggcaga ccccgctgct   86760
cgtcatagac cgagccccca gcgcagcgga cggcgccttc ccggacccct ggctgcgcct   86820
ccgcgccgcg ccctctccgg accccgcgcc gggccggcag cgcagatgtg cgggccagat   86880
gtggcgcccg ctcgccagcc aggaggggc ctggaggccg cgcgaggcgcg gggaggcccc   86940 cggcggccga gggaagctgc acaggagtcc ggctcctgtc ccgagcgggt gcacgcgcgg   87000
gggtgtcgtc gctccgtgcg cgcgagtgac tcactcaact tcaactcagc gctgcggggg   87060
aaacaggaaa ctcctcgcca acagctgggc aggacctctc tccgcccgag agccttctcc   87120
ctctcctcga cgtccagccc ctagctctct cgtagctgcc aatcatgttt cctagaccag   87180
cccctccgag agctttggcc gactttcagc tgcccctcac cgccctccca ccactcag    87240 gagttcctcg ctccaagtat ttactcaaga atgactaagt gcacacagtt cacaaagtaa   87300
caacagaaaa cgtccacgtt ttccctagta gatcagaaca tctgccgcct cccctcagct   87360
```

```
ttcttcagat tgctcctagg tgctttagag atgcgttttc aaattgcaag ttgagatcca    87420
ggagtgaata ctccaatcta ttgagtcgcg agcacatttc tttcccaaat aaaatagtaa    87480
cggtaaattc tacttcatta aatttgtgct tcagttgtgt ctatatgcat gtatgtatgt    87540
gcatacactg tcaagttgta aaatgttttt ctttaggtcg aagtctagag gttttttctca   87600 agttttaatg tacatattga tcacctggaa atcttattta aaaatgcaga ttctaattca    87660
gtaggtctag gaggcaggca gagattctgc atttctaatg agcacctgga tagagcgtcc    87720
cattttgcac cgcctcttcc cgggactgag tcagtgagta attgtaaatg atcacctatc    87780
acgaagtgat agtggtggga aatgtaattt tcagaatgta tagagtatag cagaaactgt    87840
aaaattaaaa gtgggttggg agtcacctga atgcttgtgc ttttattccc ttaatgcagg    87900
tgaagaaaga gaatacttac cctctcatgt gcaaacgggg taacatggga gcagaacagc    87960
ataaactttc aaatttcctt tcttgctagg gcaaccagat ttgcccaaga cattcctggt    88020
gtacatgttt tgtagtttaa atattaatag aaccccctttt ctctttcaga tatgtcctga   88080
ttggataata aactatgtga tcaacctact tcccactctc aaagatatga ttctgtacag    88140
ccctctggtc agtagatctt ctagcaattc atttaatgaa ttcctttacc tgagaggaag    88200
attgcagagg caagggtttg tgccagggtc tccagggaat aaaggtaaat agccctcccc    88260
caaacccaac tcccaaatct ttcctgtcat tctaagtgtt catttgcttc atcctggaat    88320
tttaactcat gctccaccta gcacccaagc tgcctctgga tgttttgcca cttcccagta    88380
ctcatgttga agatgcagaa agtgcagtga aatcaggagg gctaggcatc ttcttttccca   88440 ccaattaatt gccttgccaa agctggagtg actttgtcaa tggaggaaga ttgagttcca    88500
aatcttctcc ctattccctc ttctgccacc agcccatgcc actgccatgg cttgtgtagg    88560
agtctcccag gagtcaccct cagccacggc cgttctgggc tctttcactc agtttctcaa    88620
acgagagctg aattcagctt tcaaaatac aaaactagtt ataccaaccc tctgattaaa     88680
atcatttaat ggcttcccac tgctcttgag ataaagagaa gataaaaacc agatccttga    88740
acgtgtcttc aagcctccaa ctctcccgta aactttcatt tggcttctcc ttgcttactg    88800
aaagccttct ccaaatttcg tgaatatgcc tctgtaatcc tcctacccttt tatgcttaga   88860 gccttcccca gtgtggactt ccttcctctg accttttttt cttcacccag ccaactcctg    88920
gtcttcgtgg attgaatcat aacttctttg atgggcaagc tttccctcac ctccatgagt    88980
agatcttgta ttacacgttc tcttggcacc atat                                89014
```

<210> SEQ ID NO 2
<211> LENGTH: 4636
<212> TYPE: DNA
<213> ORGANISM: Homo sapiens

<400> SEQUENCE: 2

```
tttttttttt tttttttctag gaatgggaac aggaggcagg atgctcacct gagtattttg      60
ctttattcaa tctaataaac attttattta tgtaaaagac aaacaatgca tagaataaaa     120
ataagtgctt gagacttttg atataaaaag agtatatagc attcacattc ctatttttaat    180 acatgagtac agctgaagtg ttccataaaa gaataaaact ttcccttttat gtatagtagt    240 gaaaaaagtc agtattttta ggaactacag aatgttattc cttggtcttt tttcttgaat    300
aagaaaaaaa aacataaaca aaacaagcca cagtatcctc tgacactaca ttccagttta    360
tgctgataac ccagaagtga gaatactctt gaatcttgaa tatctcatga atggaccagt    420
attctagaaa ctcaccacta gaggtcaatg ggcaacagct attgggatgg tatcagcatg    480
```

```
ccctacggtg caagtggaat ttctaggcgc tctctatgcta ctgcagccac actgtcttta    540
actctcagcc cacccacact gaggagggtg cctagaggtt ctatttccaa acctttgcat    600
gtatcttaaa aatctcaata aaatgagacc ttccaccatc caaacagagc tgatattctc    660
actaccagtc cctctctaat attcctattt ggctgaaaat aagtagcttc aaaaagtttt    720
aaaaaagaga ttacttgcag cattaacact tctttgttga ttaacaagtt tcctatggag    780
ttttaaagct catactttgt tcttgtcctt gtggacacaa attttctaac tgcaaatggg    840
acctttgtgt cccacattca aatcctctct agtaatttct gcaaaggttg agaaggctgg    900
catgatggag agaacggtaa ccatgaggaa agcttcttgg agtaaagcac tcctctctcc    960
aatgcagagg gtaaaactat taacatataa gcaaaagaaa cttgggctaa ctgagaccct   1020
taaaggagtt cccctttagt ccaataaaag gccaacttca atcttaaca ccagataagg    1080 tagtcaaaat catattatat acccagaaa tgactgcttg aatggacatt tcttacaagg     1140
gaccttggtt aggtgcagat ttaattccta gactgggtcc aggtaggcag tggaaagagc    1200
taatgtttac agtgagaagt gaggcagctt tgtaagtgtc tccacacctt cacattttgt    1260
gaacgtggac tggagataac tgaaaaccat ctgctatcct tacctgggga tccagatttt    1320
cctgcaaaat ctccaaatat ttataaagtg gcttcactt ttgaaacgct gtgctgacca    1380
aacaaaacat atgtttagag tgcctgaggt catagtcctg acaatgatag tattgtgtag   1440
ttgaaatcct cttcatcagg ccaaactgtg cttgagcaat caggagccca gaaagatgga    1500
acccattggt gtttgtatag aaaactagaa aatcaagtca agtgtaatga aaagtaaac     1560 acgataaagc ctagagtgag aatttgctcc ttttttagaaa aggatgaagg ctgggagcag   1620
agaatagtaa cataagtgca ggggaaagat gaaaaaaaga acaatttttc attagtagat    1680
ggtggggcaa tcgcatggat ggggacatct gttctgattt ttctgcaacc catgaaggta    1740
aaaagtgggg ttcaaaacat tcaaggtatt aaagatgggg tagagtttct aaactaggtt    1800
gagggagagt ttctaaacta gccccccaga tttggggctt ggagcttaaa tgaaaagtcc    1860
aggagaaata agggcacaca ggaaccccgg gaacactggt cctcaaacag tgccactgta    1920
cttagttcca tggccagaag agaagtgcta ggcagggaat gattattttg caaaagcaag    1980
tgcaatgtgg tcatagctgg ctgtgagaca tggagcctct ttcctcatgc aaagttcact    2040
gttttacagt cagagaacca ctgcatgtgt gattgtcaaa tgctaatgct gtcatgggtc    2100
ccttccttct ctgcttggtt ctggagttct ccaataaaac caatttcctg ggaatatttg    2160
atgtttttcc ttgtctcttt tcaaggtatg gctatatata tagagctata gacatatata    2220
gatatatata tatatatata aaacatagct attcatattt atatacaggc attaataaag    2280
tgcaaatgtt attggctatt gtaaaaatca atctcatttc ctgaggaagt gctaacacag    2340
cttatcctat gacaatgtca aaggcataga atgctctatg tcacccactc cctgctgctg    2400
ttgtttctgc ttatccccac agcttacagg gaggggagtg accccttgg ttttccagga    2460 agcatcagtt caggggcagc ttcctgctgc ctctgttctt tggtgagagg gcagcctctt    2520
tggacatggc ccagcctgcc ccagaagagc tatttggtag tgtttaggga gccgtcttca    2580
ggaatcttct cctccgagca gctcctcccc gagagcctgt ccagatgctc cagctcactg    2640
aagcgttctg ccacacactg ggctgtgaga cgggcctctg ggtcgtggtc ccagcactca    2700
gtcaacgtct cacacaccat ctggatgccc tggtggttga ccagaagct gggaatttct     2760 ggtcgccctc gatctctcaa cacgttgtcc ttcatgcttt cgacacaggg gtgctcccgc    2820
accttggaac caaatggagg ctcataatct tttacttctc ccactgcatt acagcgagat    2880
```

-continued

| | |
|---|---|
| gtcatttccc agagcaccag agccatggag tagacatcgg tctgcttgaa ggactcaaca | 2940 |
| ttctccaaat tcatcctgga ttctaggact tctggagcca tgtatcttgc agttcccacc | 3000 |
| tgcccactgt tagccaggtc atccacagac agagtagggt ccagacgcag ggaaagccca | 3060 |
| aagtcacaca ggcagcaggt taggtcgttc ttcacgagga tattggagct cttgaggtcc | 3120 |
| ctgtgcacga tgggcatctt gggcctccca catggagtgt gatcactgtg gaggtgagca | 3180 |
| atccccgggg cgagggagct gcccagcttg cgcaggtcct cccagctgat gacatgccgc | 3240 |
| gtcaggtact actgtaggtt gcccttggcg tggaaggcgg tgatcagcca gtattgtttc | 3300 |
| cccaactccg tcttccgctc ctcagccgtc aggaactgga gtatgttctc atgcttcaga | 3360 |
| ttgatgtctg agaagatgtc cttctctgtc ttccaagagg catactcctc atagggaaag | 3420 |
| atcttgactg ccactgtctc aaactgctct gaagtgttct gcttcagctt ggccttatag | 3480 |
| acctcagcaa agcgaccttt ccccaccagg gtgtccagct caatgggcag cagctctgtg | 3540 |
| ttgtggttga tgttgttggc acacgtggag ctgatgtcag agcggtcatc ttccaggatg | 3600 |
| atggcacagt gctcgctgaa ctccatgagc ttccgcgtct tgccggtttc ccaggttgaa | 3660 |
| ctcagcttct gctgccggtt aacgcggtag cagtagaaga tgatgatgac agatatggca | 3720 |
| actcccagtg gtggcaggag gctgatgcct gtcacttgaa atatgactag caacaagtca | 3780 |
| ggattgctgg tgttatattc ttctgagaag atgatgttgt cattgcactc atcagagcta | 3840 |
| caggaacaca tgaagaaagt ctcaccaggc ttttttttt ccttcataat gcactttgga | 3900 |
| gaagcagcat cttccagaat aaagtcatgg taggggagct tggggtcatg gcaaactgtc | 3960 |
| tctagtgtta tgttctcgtc attctttctc catacagcca cacagacttc ctgtggcttc | 4020 |
| tcacagatgg aggtgatgct gcagttgctc atgcaggatt tctggttgtc acaggtggaa | 4080 |
| aatctcacat cacaaaattt acacagttgt ggaaacttga ctgcaccgtt gttgtcagtg | 4140 |
| actatcatgt cgttattaac cgacttctga acgtgcggtg ggatcgtgct ggcgatacgc | 4200 |
| gtccacagga cgatgtgcag cggccacagg cccctgagca gccccgacc catggcagac | 4260 |
| cccgctgctc gtcatagacc gagccccag cgcagcggac ggcgccttcc cggacccctg | 4320 |
| gctgcgcctc cgcgccgcgc cctctccgga ccccgcgccg ggccggcagc gcagatgtgc | 4380 |
| gggccagatg tggcgcccgc tcgccagcca ggaggggcc tggaggccgg cgaggcgcgg | 4440 |
| ggaggccccc ggcggccgag ggaagctgca caggagtccg gctcctgtcc cgagcgggtg | 4500 |
| cacgcgcggg ggtgtcgtcg ctccgtgcgc gcgagtgact cactcaactt caactcagcg | 4560 |
| ctgcggggga aacaggaaac tcctcgccaa cagctgggca ggacctctct ccgcccgaga | 4620 |
| gccttctccc tctcca | 4636 |

<210> SEQ ID NO 3
<211> LENGTH: 16
<212> TYPE: DNA
<213> ORGANISM: Artificial sequence
<220> FEATURE:
<223> OTHER INFORMATION: antisense oligonucleotide

<400> SEQUENCE: 3

| | |
|---|---|
| cagcccccga cccatg | 16 |

<210> SEQ ID NO 4
<211> LENGTH: 20
<212> TYPE: DNA
<213> ORGANISM: Artificial sequence
<220> FEATURE:
<223> OTHER INFORMATION: antisense oligonucleotide

```
<400> SEQUENCE: 4
gctgatgcct gtcacttgaa                                              20

<210> SEQ ID NO 5
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 5
gccatggagt agacatcggt                                              20

<210> SEQ ID NO 6
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 6
gcaacagcta ttgggatggt                                              20

<210> SEQ ID NO 7
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 7
gtgcagggga aagatgaaaa                                              20

<210> SEQ ID NO 8
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 8
gtatcagcat gccctacggt                                              20

<210> SEQ ID NO 9
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 9
ggatccagat tttcctgcaa                                              20

<210> SEQ ID NO 10
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 10
ggagaagcag catcttccag                                              20

<210> SEQ ID NO 11
<211> LENGTH: 20
```

```
<212> TYPE: DNA
<213> ORGANISM: Artificial sequence
<220> FEATURE:
<223> OTHER INFORMATION: antisense oligonucleotide

<400> SEQUENCE: 11
gagctcttga ggtccctgtg                                        20

<210> SEQ ID NO 12
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 12
gagaccttcc accatccaaa                                        20

<210> SEQ ID NO 13
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 13
tagctggctg tgagacatgg                                        20

<210> SEQ ID NO 14
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 14
ttttgaaacg ctgtgctgac                                        20

<210> SEQ ID NO 15
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 15
tcagccagta ttgtttcccc                                        20

<210> SEQ ID NO 16
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 16
tcacacaggc agcaggttag                                        20

<210> SEQ ID NO 17
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 17
tcaggaatct tctcctccga                                        20
```

```
<210> SEQ ID NO 18
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 18
tggtagtgtt tagggagccg                                              20

<210> SEQ ID NO 19
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 19
tatccccaca gcttacaggg                                              20

<210> SEQ ID NO 20
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 20
agcctctttc ctcatgcaaa                                              20

<210> SEQ ID NO 21
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 21
atgtcatttc ccagagcacc                                              20

<210> SEQ ID NO 22
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 22
aggaatcttc tcctccgagc                                              20

<210> SEQ ID NO 23
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 23
agccatggag tagacatcgg                                              20

<210> SEQ ID NO 24
<211> LENGTH: 20
<212> TYPE: DNA
<213> ORGANISM: Artificial sequence
<220> FEATURE:
<223> OTHER INFORMATION: antisense oligonucleotide
```

```
<400> SEQUENCE: 24
atgctactgc agccacactg                                                    20

<210> SEQ ID NO 25
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 25
ccttctctgc ttggttctgg                                                    20

<210> SEQ ID NO 26
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 26
ccaggagaaa taagggcaca                                                    20

<210> SEQ ID NO 27
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 27
cagcagctct gtgttgtggt                                                    20

<210> SEQ ID NO 28
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 28
cccactgtta gccaggtcat                                                    20

<210> SEQ ID NO 29
<211> LENGTH: 24
<212> TYPE: DNA
<213> ORGANISM: Artificial  sequence
<220> FEATURE:
<223> OTHER INFORMATION: antisense oligonucleotide

<400> SEQUENCE: 29
cagcccccga cccatggcag accc                                               24

<210> SEQ ID NO 30
<211> LENGTH: 23
<212> TYPE: DNA
<213> ORGANISM: Artificial  sequence
<220> FEATURE:
<223> OTHER INFORMATION: antisense oligonucleotide

<400> SEQUENCE: 30
cagcccccga cccatggcag acc                                                23

<210> SEQ ID NO 31
<211> LENGTH: 22
```

```
<212> TYPE: DNA
<213> ORGANISM: Artificial sequence
<220> FEATURE:
<223> OTHER INFORMATION: antisense oligonucleotide

<400> SEQUENCE: 31
cagcccccga cccatggcag ac                                              22

<210> SEQ ID NO 32
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 32
cagcccccga cccatggcag a                                               21

<210> SEQ ID NO 33
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 33
cagcccccga cccatggcag                                                 20

<210> SEQ ID NO 34
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 34
cagcccccga cccatggca                                                  19

<210> SEQ ID NO 35
<211> LENGTH: 18
<212> TYPE: DNA
<213> ORGANISM: Artificial sequence
<220> FEATURE:
<223> OTHER INFORMATION: antisense oligonucleotide

<400> SEQUENCE: 35
cagcccccga cccatggc                                                   18

<210> SEQ ID NO 36
<211> LENGTH: 17
<212> TYPE: DNA
<213> ORGANISM: Artificial sequence
<220> FEATURE:
<223> OTHER INFORMATION: antisense oligonucleotide

<400> SEQUENCE: 36
cagcccccga cccatgg                                                    17

<210> SEQ ID NO 37
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 37 gcagccccg acccatggca gacc                                             24
```

<210> SEQ ID NO 38
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 38
gcagcccccg acccatggca gac                                              23

<210> SEQ ID NO 39
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 39
gcagcccccg acccatggca ga                                               22

<210> SEQ ID NO 40
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 40
gcagcccccg acccatggca g                                                21

<210> SEQ ID NO 41
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 41
gcagcccccg acccatggca                                                  20

<210> SEQ ID NO 42
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 42
gcagcccccg acccatggc                                                   19

<210> SEQ ID NO 43
<211> LENGTH: 18
<212> TYPE: DNA
<213> ORGANISM: Artificial sequence
<220> FEATURE:
<223> OTHER INFORMATION: antisense oligonucleotide

<400> SEQUENCE: 43
gcagcccccg acccatgg                                                    18

<210> SEQ ID NO 44
<211> LENGTH: 17
<212> TYPE: DNA
<213> ORGANISM: Artificial sequence
<220> FEATURE:
<223> OTHER INFORMATION: antisense oligonucleotide

```
<400> SEQUENCE: 44 gcagccccg acccatg                                                     17

<210> SEQ ID NO 45
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 45
agcagccccc gacccatggc agac                                            24

<210> SEQ ID NO 46
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 46
agcagccccc gacccatggc aga                                             23

<210> SEQ ID NO 47
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 47
agcagccccc gacccatggc ag                                              22

<210> SEQ ID NO 48
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 48
agcagccccc gacccatggc a                                               21

<210> SEQ ID NO 49
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 49
agcagccccc gacccatggc                                                 20

<210> SEQ ID NO 50
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 50
agcagccccc gacccatgg                                                  19

<210> SEQ ID NO 51
<211> LENGTH: 18
```

```
<212> TYPE: DNA
<213> ORGANISM: Artificial sequence
<220> FEATURE:
<223> OTHER INFORMATION: antisense oligonucleotide

<400> SEQUENCE: 51
agcagccccc gacccatg                                                 18

<210> SEQ ID NO 52
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 52
gagcagcccc cgacccatgg caga                                          24

<210> SEQ ID NO 53
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 53
gagcagcccc cgacccatgg cag                                           23

<210> SEQ ID NO 54
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 54
gagcagcccc cgacccatgg ca                                            22

<210> SEQ ID NO 55
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 55
gagcagcccc cgacccatgg c                                             21

<210> SEQ ID NO 56
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 56
gagcagcccc cgacccatgg                                               20

<210> SEQ ID NO 57
<211> LENGTH: 19
<212> TYPE: DNA
<213> ORGANISM: Artificial sequence
<220> FEATURE:
<223> OTHER INFORMATION: antisense oligonucleotide

<400> SEQUENCE: 57
gagcagcccc cgacccatg                                                19
```

```
<210> SEQ ID NO 58
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 58
tgagcagccc ccgacccatg gcag                                          24

<210> SEQ ID NO 59
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 59
tgagcagccc ccgacccatg gca                                           23

<210> SEQ ID NO 60
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 60
tgagcagccc ccgacccatg gc                                            22

<210> SEQ ID NO 61
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 61
tgagcagccc ccgacccatg g                                             21

<210> SEQ ID NO 62
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 62
tgagcagccc ccgacccatg                                               20

<210> SEQ ID NO 63
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 63
ctgagcagcc cccgacccat ggca                                          24

<210> SEQ ID NO 64
<211> LENGTH: 23
<212> TYPE: DNA
<213> ORGANISM: Artificial sequence
<220> FEATURE:
<223> OTHER INFORMATION: antisense oligonucleotide
```

```
<400> SEQUENCE: 64
ctgagcagcc cccgacccat ggc                                              23

<210> SEQ ID NO 65
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 65
ctgagcagcc cccgacccat gg                                               22

<210> SEQ ID NO 66
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 66
ctgagcagcc cccgacccat g                                                21

<210> SEQ ID NO 67
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 67
cctgagcagc ccccgaccca tggc                                             24

<210> SEQ ID NO 68
<211> LENGTH: 23
<212> TYPE: DNA
<213> ORGANISM: Artificial sequence
<220> FEATURE:
<223> OTHER INFORMATION: antisense oligonucleotide

<400> SEQUENCE: 68
cctgagcagc ccccgaccca tgg                                              23

<210> SEQ ID NO 69
<211> LENGTH: 22
<212> TYPE: DNA
<213> ORGANISM: Artificial sequence
<220> FEATURE:
<223> OTHER INFORMATION: antisense oligonucleotide

<400> SEQUENCE: 69
cctgagcagc ccccgaccca tg                                               22

<210> SEQ ID NO 70
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 70
ccctgagcag ccccgaccc atgg                                              24

<210> SEQ ID NO 71
<211> LENGTH: 23
```

```
<212> TYPE: DNA
<213> ORGANISM: Artificial sequence
<220> FEATURE:
<223> OTHER INFORMATION: antisense oligonucleotide

<400> SEQUENCE: 71
ccctgagcag cccccgaccc atg                                           23

<210> SEQ ID NO 72
<211> LENGTH: 24
<212> TYPE: DNA
<213> ORGANISM: Artificial sequence
<220> FEATURE:
<223> OTHER INFORMATION: antisense oligonucleotide

<400> SEQUENCE: 72
cccctgagca gccccccgacc catg                                          24

<210> SEQ ID NO 73
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 73
atgtgaagat gggcaagacc                                               20

<210> SEQ ID NO 74
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 74
atctccatgt gaagatgggc                                               20

<210> SEQ ID NO 75
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 75
aacggcctat ctcgaggaat                                               20

<210> SEQ ID NO 76
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 76
aacatcgtcg agcaatttcc                                               20

<210> SEQ ID NO 77
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 77
aatccaactc ctttgcccTt                                               20
```

```
<210> SEQ ID NO 78
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 78
aaacctgagc cagaacctga                                               20

<210> SEQ ID NO 79
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 79
agggcgatct aatgaagggt                                               20

<210> SEQ ID NO 80
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 80
agtgcacaga aaggacccac                                               20

<210> SEQ ID NO 81
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 81
acactggtcc agcaatgaca                                               20

<210> SEQ ID NO 82
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 82
ttcctgttga ctgagttgcg                                               20

<210> SEQ ID NO 83
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 83
cactctgtgg tttggagcaa                                               20

<210> SEQ ID NO 84
<211> LENGTH: 20
<212> TYPE: DNA
<213> ORGANISM: Artificial sequence
<220> FEATURE:
<223> OTHER INFORMATION: antisense oligonucleotide
```

```
<400> SEQUENCE: 84
caaggccagg tgatgacttt                                            20

<210> SEQ ID NO 85
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 85
cacactggtc cagcaatgac                                            20

<210> SEQ ID NO 86
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 86
ctgacaccaa ccagagctga                                            20

<210> SEQ ID NO 87
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 87
ctctgccatc tgtttgggat                                            20

<210> SEQ ID NO 88
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 88
tcaaaaaggg atccatgctc                                            20

<210> SEQ ID NO 89
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 89
tgacaccaac cagagctgag                                            20

<210> SEQ ID NO 90
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 90
tgatgccttc ctgttgactg                                            20

<210> SEQ ID NO 91
<211> LENGTH: 20
```

```
<212> TYPE: DNA
<213> ORGANISM: Artificial sequence
<220> FEATURE:
<223> OTHER INFORMATION: antisense oligonucleotide

<400> SEQUENCE: 91
ttcctgttga ctgagttgcg                                             20

<210> SEQ ID NO 92
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 92
ttctccaaat cgacctttgc                                             20

<210> SEQ ID NO 93
<211> LENGTH: 20
<212> TYPE: DNA
<213> ORGANISM: Artificial sequence
<220> FEATURE:
<223> OTHER INFORMATION: antisense oligonucleotide

<400> SEQUENCE: 93
ggagagttca ggcaaagctg                                             20

<210> SEQ ID NO 94
<211> LENGTH: 1512
<212> TYPE: DNA
<213> ORGANISM: Homo sapiens

<400> SEQUENCE: 94
ttacattttg atgccttcct gttgactgag ttgcgataat gttttcttaa tccgcaatgc    60
tgtaagccta gctgctccat tggcatacca acattctctc ataattttag ccattactct   120
caaggcttca cagctctgcc atctgttttgg gatatttggc cttaacttct gttcacaaac   180 aactttctc atttcttcaa ctgatgggtc agaaggtaca agatcataat aaggcagttg    240
gtaatcttca tgaattccac caatggaaca tcgtcgagca atttcccaga atactaagcc   300
cattgcatag atgtcagcac gtttgaagga ttcaaaatgt ttcatattta tggaatcatc   360
gagaacttca ggggccatgt acctttttgt tcccactctg tggtttggag caatatcaat   420
ggtatctgtg gctgaatcat gtcttactgc cagtcctaag tctgcaatac agcaagttcc   480
attcttcttt accaagatat tctttgattt caaatctcta tgagcaatgg ctggctttcc   540
ttgggtacca acaatctcca tgtgaagatg ggcaagaccg ctcgccgtgg acagagcaag   600
ttttatcatt ccttccacag taactgtgta tctgtttaag taatcaaaaa gggatccatg   660
ctcatgataa tctgacacca accagagctg agtccaagta ccattgtctt tattgtctgc   720
tgctataaat cccaggatgt tttcatgacg taacattaca gtttgataaa tctctgcctc   780
acggaaccac gaacgttctt ctctagagga gaatatctta acagcaactt cttctccccg   840
ccactttcct ctccaaactt ctccaaatcg acctttgcca atgctttctt gtaacacaat   900
agttctcgca attgttctct gaacaagcaa tggtaaacct gagccagaac ctgacgttgt   960
catatcataa attaagtctt tcaacgtagt accctctgaa ataaagggc gatctaatga  1020 agggtcctct tcatttggca ctcgatggtg aatgacagtg cggttgtggc agatatagac  1080
catcaacatg agtgagatgc agacgaagca cactggtcca gcaatgacag ctgccagttc  1140
cacaggacca aggccaggtg atgactttac agtagttgga agttctattt tattgcaatg  1200
```

| | |
|---|---|
| gtcctgattg cagcaatatg ttgtagtcac agacccagtt tttgaagagg gtgcacatac | 1260 |
| aaacggccta tctcgaggaa ttaagtcaat ttcagctata cacatgctgt tgtgtataac | 1320 |
| tttgtctgtg gtctctgtga cagagacaaa gcagagccca tctgtcacac aagtaaaatt | 1380 |
| gtcttttgta cagaggtggc agaaacactg taacgccgtc gcccccggga gcagcgccgc | 1440 |
| cgccgccgcc gccgccgccg ccagcacgag gaggagcagc cggggacgcg gagcagcgac | 1500 |
| cgccgcctcc at | 1512 |

<210> SEQ ID NO 95
<211> LENGTH: 2308
<212> TYPE: DNA
<213> ORGANISM: Homo sapiens

<400> SEQUENCE: 95

| | |
|---|---|
| aaacactata ggttttaaca tagagacttt cagcaattct actcatttcc attagaaaga | 60 |
| cacagaagtg gcacttactg gtatagtaca atcccatttt gaaggcatgt aatgttctga | 120 |
| ataagtgaaa gaacaataat agtatacaaa atacaattgc atgaattatg ttcctcacta | 180 |
| ctatatgagg tcattttag actcaagata agagttttat aagtgttagt tttaagatcc | 240 |
| tgaaaaacta tagaacagta cattcaaagt ctgaatcaag gaaactctag tggttcagaa | 300 |
| tcctctgaga atgtactaac caggagtaaa tcactttctt tagtaataag acatgtttca | 360 |
| ttgtaattca gcaatccaac tcctttgccc ttaaagatga tctccagcac agcagagtta | 420 |
| cctaaagtta agaccagcaa tcatcttttt aaaaaacaag ttttgttaat aaaaaataaa | 480 |
| ggtagactac acattttctg tcctgggaaa gaagcgttca tagtgcacag aaaggaccca | 540 |
| catggctgtt tcctgggtcc aaagaaatcc tgggaagttt ttaattgact ttattacact | 600 |
| gctgcaaaag gaagcaatat ccttctgttc cctctcagtg aggtagaaca attgacctcc | 660 |
| caaattaaaa cccaggagca gatctgaaga aaaaaggaga gttcaggcaa agctgtagaa | 720 |
| ttacattttg atgccttcct gttgactgag ttgcgataat gttttcttaa tccgcaatgc | 780 |
| tgtaagccta gctgctccat ggcataccca acattctctc ataattttag ccattactct | 840 |
| caaggcttca cagctctgcc atctgtttgg gatatttggc cttaacttct gttcacaaac | 900 |
| aacttttctc atttcttcaa ctgatgggtc agaaggtaca agatcataat aaggcagttg | 960 |
| gtaatcttca tgaattccac caatggaaca tcgtcgagca atttcccaga atactaagcc | 1020 |
| cattgcatag atgtcagcac gtttgaagga ttcaaaatgt ttcatattta tggaatcatc | 1080 |
| gagaacttca ggggccatgt accttttgt tcccactctg tggtttggag caatatcaat | 1140 |
| ggtatctgtg gctgaatcat gtcttactgc cagtcctaag tctgcaatac agcaagttcc | 1200 |
| attcttcttt accaagatat tctttgattt caaatctcta tgagcaatgg ctggctttcc | 1260 |
| ttgggtacca acaatctcca tgtgaagatg ggcaagaccg ctcgccgtgg acagagcaag | 1320 |
| ttttatcatt ccttccacag taactgtgta tctgtttaag taatcaaaaa gggatccatg | 1380 |
| ctcatgataa tctgacacca accagagctg agtccaagta ccattgtctt tattgtctgc | 1440 |
| tgctataaat cccaggatgt tttcatgacg taacattaca gtttgataaa tctctgcctc | 1500 |
| acggaaccac gaacgttctt ctctagagga gaatatctta acagcaactt cttctccccg | 1560 |
| ccactttcct ctccaaactt ctccaaatcg acctttgcca atgctttctt gtaacacaat | 1620 |
| agttctcgca attgttctct gaacaagcaa tggtaaacct gagccagaac ctgacgttgt | 1680 |
| catatcataa attaagtctt tcaacgtagt accctctgaa ataaagggc gatctaatga | 1740 |
| agggtcctct tcatttggca ctcgatggtg aatgacagtg cggttgtggc agatatagac | 1800 |

-continued

| | |
|---|---|
| catcaacatg agtgagatgc agacgaagca cactggtcca gcaatgacag ctgccagttc | 1860 |
| cacaggacca aggccaggtg atgactttac agtagttgga agttctattt tattgcaatg | 1920 |
| gtcctgattg cagcaatatg ttgtagtcac agacccagtt tttgaagagg gtgcacatac | 1980 |
| aaacggccta tctcgaggaa ttaagtcaat ttcagctata cacatgctgt tgtgtataac | 2040 |
| tttgtctgtg gtctctgtga cagagacaaa gcagagccca tctgtcacac aagtaaaatt | 2100 |
| gtcttttgta cagaggtggc agaaacactg taacgccgtc gcccccggga gcagcgccgc | 2160 |
| cgccgccgcc gccgccgccg ccagcacgag gaggagcagc cggggacgcg gagcagcgac | 2220 |
| cgccgcctcc atggtcccgc cgccaccgcc tgtggcccgg cccggcccgg ccgcgccgct | 2280 |
| gcctcacccc agcaaacctc gcctcgcc | 2308 |

<210> SEQ ID NO 96
<211> LENGTH: 48775
<212> TYPE: DNA
<213> ORGANISM: Homo sapiens

<400> SEQUENCE: 96

| | |
|---|---|
| cctaggatgg gcagtataaa caactgtgtt tttaaatgac aaaattatta ctctaatcaa | 60 |
| atttatctgc agttatcgac agtaatcatg atccatccca ccttttaagt ttctttcatt | 120 |
| ttcaatatca gccaattgtg gtttatcaaa ccatccctag ccaaaaaagg aattaactgc | 180 |
| agtaatacgt aaagtcaatt tagaactaaa ctccaacttt aaaaaaattc cctgattcat | 240 |
| caaaagtaca tttatccac ttaggtaaga aagtatataa tgtaactcaa tctttgattc | 300 |
| aataaaaaat atcttcagca aagtggata accttacatg aaagtgagaa atcatgtatt | 360 |
| acaactttaa atcagacaac ttttggtata ttcttaaaat tatataaaaa tagtttttagt | 420 |
| gataaaatgc attggtcccc tggatttcat aaagcagatc tggtaggctt agaaatggcc | 480 |
| caaaacaac aacaaaaaaa aaaaacaaa aaaaaaccc ccacaaaaaa agtacctgat | 540 |
| cacagaatta gagattatta ttaaacaagt aatacaacac aactataaaa acaaacctct | 600 |
| caaactcatt catttgcttc aatgaaatta tggtaactac agaaaaaaac tcaactttgt | 660 |
| agtcaaaata gtaacctcta agcattttc ccatgatgtt tttaaacaca tgaaattgac | 720 |
| actaaattcc tatgtaatat gtcactcatt ctaaaattac tttggtttta agatcaaata | 780 |
| gtctttcaaa tttattctac gtaagagaa taagacatta tcagaatgca actcattcag | 840 |
| tgtaaatggc cactttctct tcctgaccaa aatactgtat gggttactct gaccctgtat | 900 |
| cggggaactg atagcactat aaagtcgaag tcttgcctca gagctatgat agttttttct | 960 |
| ccctcagaa taagatcaca gtgataaaag gacttcgaaa actgtaaaag ccctgcagag | 1020 |
| acttcatagc attggaagta aaaccagtt attataagct agtttcaact taatgtaaga | 1080 |
| agaccatgac aagtttgctt tcaatatttg accaaagaca tctgtaaatg gagaaaaacc | 1140 |
| tatactcaga atgttcttta gctaccacct ctcccaagta acaagggtgc actgaatgca | 1200 |
| ttacataaat tacatgtaag cagttgcaat gtacgcacac ataaggaaac actgaattaa | 1260 |
| aagctgcctt cctcaaagtg tagtgagacc tcaaaaccac actagctcta acctcagtta | 1320 |
| caaagacaga ggatccaccg aacgttact cctacataca taacaaatgt gactttcttg | 1380 |
| cacatctgtt atctattcaa attattaact accttcgcct tcctagaaaa aggcctatta | 1440 |
| tttaatatta accatattct aatttttaaat gtaattcatg tcttaaaaaa taagtctttg | 1500 |
| aacagataaa gaaaaaaatg gcttacgaaa taccacataa cttttcacaa gcagctagac | 1560 |
| agactttccc ttttagaaaa attagtctgt atgctacaaa tattaaagta ctataagcat | 1620 |

```
ctagagtgcc acttgatttt ttaaaagtat acttagacaa cacaattaaa atgcaaaagc   1680
ttgatgtgag aatattcaaa catgaccatg ctaataattt actaattaat gccacttcat   1740
ttctttagtg gcttaagcac attttggtag gagaaaggca ttttcagaat agaataccaa   1800
atgacatacc acaaaaaccc ttccaaaaac aaaacagaaa aagtttgggt tacccagata   1860
aataagcttt ttgaattcaa acactatagg ttttaacata gagactttca gcaattctac   1920
tcatttccat tagaaagaca cagaagtggc acttactggt atagtacaat cccatttttga  1980 aggcatgtaa tgttctgaat aagtgaaaga acaataatag tatacaaaat acaattgcat   2040
gaattatgtt cctcactact atatgaggtc atttttagac tcaagataag agttttataa   2100
gtgttagttt taagatcctg aaaaactata aacagtaca ttcaaagtct gaatcaagga    2160
aactctagtg gttcagaatc ctctgagaat gtactaacca ggagtaaatc actttcttta   2220
gtaataagac atgtttcatt gtaattcagc aatccaactc ctttgcccctt aaagatgatc  2280 tccagcacag cagagttacc taaagttaag accagcaatc atctttttaa aaacaagtt    2340 ttgttaataa aaaataaagg tagactacac attttctgtc ctgggaaaga agcgttcata   2400
gtgcacagaa aggacccaca tggctgtttc ctgggtccaa agaaatcctg ggaagttttt   2460
aattgacttt attacactgc tgcaaaagga agcaatatcc ttctgttccc tctcagtgag   2520
gtagaacaat tgacctccca aattaaaacc caggagcaga tctgaagaaa aaggagagt    2580 tcaggcaaag ctgtagaatt acattttgat gccttcctgt tgactgagtt gcgataatgt   2640
tttcttaatc cgcaatgctg taagcctagc tgctccattg gcataccaac attctctcat   2700
aattttagcc attactctca aggcctacaa gaaaatataa aaaaaaaaat taatgcatgc   2760
accattttcc attggtctgg ataagaattt ttacgtgtaa attttctttt taaatgacat   2820
atacacttgt tattgtttaa gcattatttg taatagcaaa tgagtagaaa ttacataaat   2880
ttccatcaat agggtactgg tgccagtgct ggaaagcagg tggacaaaga gtgactcatt   2940
tagcaaacct gaaaaggccg aatcctaaac cagagctggg caaagcaaag aagaaatctg   3000
acctcacact gaaattttaa gtttgtactt tgaagtattc acatcaaatt tttctttctt   3060
tttttttttt ttgagacagg gtctcactct gccgcccaaa gtggaatgca atggcatgcc   3120
ctcagctcac tgcagccttg acctcccagg ctccagcaat cctcccactt cagcctccca   3180
agtagatcaa atttctaaaa gacaaaatct agcagcactc tcatttatta aactatgtca   3240
catgcaaatt ccttaagcat gctgaaatac atttttattta tttgggcctg gagatgtgat   3300
tttgttggag gtagcaagct ctcttgctta tcagaggttc tgctgagtcc tacaatagtt   3360
taagacgtaa aatcaactac tgaactgaac agcttttttat agccttttta agctacaaat   3420
cttcaaacct ggaggaatat gctctgcttc accaatattg taatagtaac agctagcaat   3480
taaggagagg ttaaataaaa ttcatcttac gaatctttaa atttacaatt acaaaaacgt   3540
ttctaaaact ttttgttaga gctgaagttg agcagctcag atactgctgg aaaaaagcat   3600
tttccctaaa ttcctggtta acggttatct gggcaatcag atgaataaaa cggaaaatca   3660
tttgaaacac ctttgtaatc accttatctg agttcctcac cttgcaaagg gatattaaag   3720
tccagagaac taagggatt tgttcagagt cagaccttg aaatggtagc caggctggtc     3780
tagaatacag ggctcctcat tcatgtccgg taactgtcta gtgttctggg ttgccccggc   3840
tgaagggagg cattcattta aaaatatgtg ccttagttcg cccggcagat ctaaactatg   3900
ttctgataca ctaaaggcca ctgcaaatgt tccatggccc tttcaatgtg cttacaattg   3960
aatatgaaaa ccaaattatt ctgtttttaa acattggttt gactgctatg aaaaagaaaa   4020
```

```
ttcttaaaga aaagttttcc ttaaagaaaa gtagcaaact tttgcttact aagcagaagc    4080
agtttagaaa attgcctaat atcaaaaga  aatactcact tcacagctct gccatctgtt    4140
tgggatattt ggccttaact tctgttcaca aacaactttt ctcatttctt caactgatgg    4200
gtcagaaggt acaagatcat aataaggcag ttggtaatct tcatgaattc ctgtatcagt    4260
ttaaaaaaaa ttaaattttg atgaatttat tcagctaatg ccaaggcatt aaaagatcac    4320
ctgagagacc tattacagtg tttcattact aaagtaggta tgtggaacag agattacagc    4380
tttctctatc tcatccacat ctgtatccac aagccacttc cctgagttga tattccaccc    4440
acaccttgaa actaagtatt gccatgagat caataaagcc tatttgaaat gacagtaaac    4500
tatgagctgt gatgaccaga ttgacatttt cccctagaac cctattgtgc agcaaatgag    4560
attctattct gtaagtgcac aggctctcac ttgcacaggg atatatatac cctatcagtg    4620
agacttgaat cttatgaggc aagtttaagg tgccaagtcc ctttctctac ttgcatctgt    4680
caataatata tcctatttac tacaatacag agaaatactc tgtccctcac tgcttcaaaa    4740
acctaaggca ctaggtctca gccaagtcta ggtccccaag cctaagagac tgtttcctga    4800
gtaaacatta aaagtactcc atctaaaaag ctagaagtta aaacaaacta actctagaat    4860
acaacacaat ggtaacataa ttgtattctg tgtatgtaac tgtaactatc aagttggaga    4920
aaataaccac aatctcaaag aaaaaaaata agtttgacac ccaggtacat gctagaaaca    4980
gcttcctagg tgagcctctc aagcagctgt ccattctaaa gaactatatt ccaatataac    5040
aaggggttgg gttctgatga gtctccagat tcaaatggaa acaggaagag aatacactag    5100
gctagagctg tgcatgtgca caccatggca ctgtcccctc ccaaaggttt catcgccttt    5160
gttttctctg gcactcggtg acatcctgtt tcagataatg gactgtacat aatttcattc    5220
aattaaaaaa agaagacaat tcttgaacaa cttctgctca tgacaaacta ctgggggaga    5280
ggagagcaat ttaccaccaa tggaacatcg tcgagcaatt tcccagaata ctaagcccat    5340
tgcatagatg tcagcacgtt tgaaggattc aaaatgtttc atatttatgg aatcatcgag    5400
aacttcaggg gccatgtacc taaaaaaaat ttgcaaaaag aactttgaaa atcatcccct    5460
tactgccata tttggatgaa cctccttca  gacatttctt tatacataga catatgtaca    5520
caatattaca taacaaatat tagactcaag aaaaatatta aatatccaca ctggtttgca    5580
cattaatgat gtcaactaaa tcccacaaaa tgctaaaata gcagtttcac actatctgcc    5640
tcatgatctt ggtttccaat gaaagacata cataacaatt gtgactgtta aaggtgtcct    5700
aatgtacacc acctatacac gtactaggta gaaaccatgc attttaattt agaagtcttc    5760
tcactgagga tgaaaggaag ggcacgaata tactccaggg aaaaaaataa tagatacaaa    5820
agaatgccag tcctcatact gaagcttcaa aaacctacca aaattatggg tcaggaccca    5880
cagagaccta cagcaaccac tgacaaggac cccttagctg gttgagaatt gagagtcatc    5940
tacggccata ccaccctaaa cacgcccgat ctcgtctgat cttggaagct aagcagggtc    6000
gggcctgctt agtacttgga tgggaaaatt gagagtcccc agggaatcca gaaatctcaa    6060
aattatacat gcaatttgaa tagactaatg ctgctggctc tccagctgtc tccaaggcca    6120
agacagtagt ttgaaaaaat gctgtgacag cttgtgataa ggggtttggg tcagaaatgc    6180
ccaggttcaa atctcagctc ttcggcttat catccacatg aagctggcca tattatttaa    6240
cctcctcaag gtggtttcct catctgtgaa ttaagggta  ataacaccta cctaattaag    6300
ttcttttgaa gactcatgga ctcaacaaat atctactgag gatctaccat gtattaggca    6360
ctgtgatgga tgctgggaat acaaggctgc tctcaagcag cttgcaccta atagaatata    6420
```

```
taggcaaata aataaacagt tacaacataa cgcataagtg cctcaacggt cccagttcag    6480
tgtgctatga cagtccctgg cagggactcc taagattttt gaggactaga aaaaacttcc    6540
tacgggaaag gtgggtatga ggctgagaaa cagtagggta agtatgctc caggagacag     6600 catgtgcaaa agttctaaga aagcaagaaa ggcatatttt taggaactga aatatgaaaa    6660
tagcagggct agctactgca cagtatttga aagggatta aatgaggtaa tatacgtaaa     6720
agacctatta gacgattggc acatagtagg tgccctataa acgttagtta ctactgttat    6780
tataattaac atgcctaatg atattttctg gaagggcaac cttttcatcag caggcatctt   6840 tttaagtcag gtaactctgg cttcagagca ggcaagacca tgagatcttc ttacctgttg    6900
gcaatctaat aaagtgcaag tttaagctga gtttcagcaa tgatatgtat atatgaaaga    6960
gaagggaaaa aaggtgattt cagaagatat taaatatagt tgttcaaaag tataccttt    7020 tgttcccact ctgtggtttg gagcaatatc aatggtatct gtggctgaat catgtcttac    7080
tgccagtcct aagtctgcaa tacagcaagt tccattcttc tttaccaaga tattctttga    7140
tttcaaatct ctatgagcaa tggctggctt tcctaaagaa tcaaaaatta acatgactg     7200 cttaaaaggt aataccaatc acaactcaca tctttaggtt caaaagtctc ttctcccaac    7260
ccaaattatc aaagcatttc agcccacatg acctacaata cttacgggca ttattaaact   7320
caagtgaatc actacaccaa aagtcactga atttatattt cttaaagaa atgtgggaca    7380 ataacatgct ttaaaagatg aacaactcaa agactggggc aaaaaaaaag ttatcagttt   7440
atctgttggt gccttatgaa ttctttttaa gaaacttagc catagactga tattccagca   7500
gcccaggaac caagcatgta gaacatcact tccctatcaa ctgcaatgta ctcagtatta   7560
agtatattat ctttgatgct aaccactaga aaatgttatt aaaaaataat aattataatg   7620
tggaaaacct ggaaccttca tacactgctg gcaggaatgt aaaatggttc aggcactta    7680 agaaaatagt atggcagttc ttcaaaccat taaatagagt tatcatatga tacagtaatt   7740
caactcctag gtatataccc aagataactg aaaacatgaa actacataca acttgtacac   7800
aaatgttcac tgcagcatta gctacaatgg ccaaaagaaa caaaccaaat gtccatcaac   7860
gaacggatat atgacatatg ccatatccat acactgaagt attacttagc catcaaaatg   7920
actgaagtac tcatcgtgc tacaacataa atgaaccttg aaaacatgct aagtgaaaga    7980
agccagtcac aaaagaccac atattgtatg attcatttat ataaaatgtg cagaataagc   8040
aaatctacag acaaaaagga gcagttgttg cctagggcta aggagtttgg gaggaaaggg   8100
gagtgactgc tagtggctac agggtttctc tttggagtga agatattcta aaattgactg   8160
tagtgtttgc tggctgtaca actcttgagt attctaaaaa ccactgaatt ttacacttta   8220
agtgggtgaa ctttatgatg tgaattataa ctcaataaaa ctgttacaat caataataat   8280
aataactaca aagatggagc taagatgtga actagcactt atgctgtatg taaagtgggg   8340
agtgggggag ccattgggtt gcaagtggac aactgctaga gcagagagat atactggcat   8400
ctgaaatccc acatgcacaa aaactacagc atacaaatgt cataactaaa acttagtatt   8460 taattttca actgtaaaac tatctcatgc agtctcctta tctcaaggtc aaatataatt    8520
attagatggc cagataacag ttacctagca tgttgatgtt tacaaagcac tttcacattt   8580
catttgatac tacacataaa aatatattca gttggacctg aattctgaaa ctgagatcct   8640
caaaaatcat aagattgaat gctacttttα agaactcaaa aaaaatcaca gttttgttac   8700
aacgactaga gaatctctaa acaaatttcc agattcctag ctctacctga aattttgaac   8760
tgaaagataa aatgttctca tctaaaaaat ttgttttaaa tatctccagt taggccacct   8820
```

```
actgttttg  tttttgtttt  tttttctgag  acagggtctc  tctctattac  tcagctggga   8880
gtgcagtggc  atgatgtctg  ctcactgcag  cttcgacctc  ccaggctcag  gtaatcctcc   8940
tacctcagcc  ccctgagtag  ctgggactac  aggtgcatgc  caccatgccc  gactaatttt   9000
ttgtatgttg  gtagagatgc  ggttttgtca  tgttgcccag  gctggccatg  aactcctgag   9060
atcgggcgat  ctgcccacct  cagcctccca  aagtgctggg  attataggca  tgagccacca   9120
ggcccagcct  ccaccttcta  ttttcataga  cattattcat  gaaaatttaa  agcttaaata   9180
atagaactgc  ttatagaatt  accttgggta  ccaacaatct  ccatgtgaag  atgggcaaga   9240
ccgctcgccg  tggacagagc  aagttttatc  attccttcca  cagtaactgt  gtatctgttt   9300
aagtaatcaa  aaagggatcc  atgctcatga  taatctgaca  ccaaccagag  ctgagtccaa   9360
gtaccattgt  ctgtaaaaca  gaattaacat  ttcggttggg  ctgcagacca  tttatgattt   9420
atttgttcaa  tggttattac  tttttactct  caatcctgag  tcacacactg  caatataatg   9480
ccaccttaag  tctgtatttc  cttcacattt  tcttctacat  tgtttgtttt  atactttat    9540
gtacacatcc  tttagttcct  cagagtaagc  ccctcttctt  gagataaggc  aagtataatt   9600
aatcccattt  aagagacaaa  gatggtgact  tttttgagtc  ttcacagata  attggtatca   9660
gagctggcac  tcttaagtgc  ctagaaaaat  ctctgggtcg  ggttgggtgc  tcagtggctg   9720
ttcctggaag  gagagaaggt  taaaaaaaag  gaaggaacag  agagggaagc  aaggaggtga   9780
gaagtctccg  gagaccagtg  tggccacagt  gggaatggaa  gagtatggga  caaaactgaa   9840
agtgagtttc  aacaagaaat  gacaagcttt  agtgacagat  tgtgtacaca  gttcacaaag   9900
acgcaagaca  agatgattat  gattccaagg  ttgctagctt  agaaaaacag  aaatagtgat   9960
acctctaaca  catggggaag  ctgaaatagg  aactgaaatg  tcaggagcaa  aactggaaaa  10020
gctgggacta  aactcaaaca  acgaggaacg  tgggttccaa  aatttcctct  gtaagccaaa  10080
acacgagttt  aaaacatgtt  ttctcatagg  aataatggta  aagacactag  ctaggctcct  10140
aagctagact  ggtccacgac  aatctaattt  aacctagaag  tagctggaaa  accacatgct  10200
taattaagcc  atgaagaaaa  aaagcattac  aacattagga  gacagcacaa  tccagtaaaa  10260
gatggacgct  tagagtcatt  ctaacctggt  tggaatccac  ggcctgcctg  ttactgacaa  10320
ggagcctgtt  tctccttta   tacaagaata  aagtcttact  ttgtaagact  gttaagattt  10380
aaaaaacgga  atgctagatt  ctttaggtaa  gaagtacata  aactgtgctc  tttctttccc  10440
tgctggttgt  aaaccaaaag  aaaaaatcca  tattgacatg  aaacagcttc  tattttgaag  10500
gtatttggtt  gaagaagaaa  accaactctg  attagaagag  attaagaaag  gaatagaaac  10560
ttttcagaag  attctggagg  agatttctgg  gtacatttaa  aaggacttag  tattaatttg  10620
ttcttcatga  actttataaa  ctgattctga  ccaaactcgc  accttgctt   ttccttgata  10680
taggcacatc  actagcttat  ttgcatgcct  cttaaccatt  actgaatttt  gaaaagctca  10740
caaatacaag  aaacaaagtg  gaagacaggc  agatggaaga  aagggaaacc  acaggttatg  10800
gacaagatag  aaggaaggtt  atatgtaagg  ggccataaat  ataaagggct  gccggggggtg  10860
gaattaacta  aatcaggaga  agataaagga  actgaggtgg  aggggctagg  ctcagagaaa  10920
gtacattaac  ccctgacaaa  gaagaaagaa  ggggagtagg  gaagagccag  tagggtcagc  10980
tagttcccat  ggtgaccacc  agatgacagc  atcagcctgg  ttagaagttc  agggcacaga  11040
ctcaccaaca  ttttgtgctg  ctgtgtttgt  aacttggaat  gtgacaaaat  ccagaccctg  11100
ggtgaggttt  aagcttcaa   atggagattt  gagagttgcc  aacatggtag  agtttgaaac  11160
catgaatgtg  gctatgttct  taaggaagaa  attaccactt  ataaaatcag  taccttcata  11220
```

```
tgaaccagtg agaagagtaa gagttgagaa aacaaagaca actatgaaga agtaagaagg  11280
aacaaggaaa gtctagggtc atcaaacaca gtaaataaag aaaaggttgt tttaagagtt  11340
gggggaggaa ataatggtg ataaaggcag aaacgaaaat gagaactaag gatttggtca   11400
gactgattac tattttttgt tttgttttgt tttgttgttg tttttttttt gagacagagt  11460
ctccctgtgt cgcccaggct ggagtgcagt ggtgcgatct cagctctgac tgcaacctcc  11520
acctcccagg ttcaagcaat tctctgcctt agcttcccaa gtagctggga ttataggcac  11580
ctgccatcat gcctggctaa ttttttttgta tttttagtag atgggggtt tcatcatctt   11640 ggccagccag gctggtcttg aactcttgac ctcgtgatcc acccaccttg gcttcccaaa  11700
gtgctgggat tacaggcgtg agccactgtg cccggcctgt tttgttttta acttaagagg  11760
tattacattg tcaggtgcca ctgataatcg ctacctacat tcatcatata cctcactgcc  11820
ccgtcttaat caaacactat acacctccac atatgatgca ataggatgta tataatatcc  11880
ttagtatgta ttttgagaaa accaataaaa ctccaattag gtttagcttc taaatctaac  11940
taccagtttt cagaaaagat agaagaacaa gttaagagac actatggaaa tgcaatcagc  12000
aaaatccaga atgtgatagg cccttcagga taaacaatcc aatttcttca acaaataagc  12060
tgcgagagga gaaaaagat gaaggggga cctaaatttt aagacacata agagaaatat    12120
caactaaata taacttgtgg acttagaatc ataatttgaa taaataattt ttttaatagg  12180
agacaattat agaattgaac ctaactggat atttgataac atttaaaaaa ctgacaatgg  12240
tagtgtggtt gtttcataaa aacatttcct catcatttga agatacaaat tacatttat   12300 aagtgtttac agatgaaaac atattgtctg ggaccagctt caaataacac agttagggca  12360
gagtaggtgg gatcagacat caattatgat tggcagtgac ctgacaactg ttgaagctgg  12420
acgatgaggg atcactgtaa ctactctgct tttctacata ttggaaattt tctacaaata  12480
aaagtcaata acaaaaaaaa gcagtacatg cttgtaaata aatttgaaaa cccagagaag  12540 ctaaagaaa aataataaaa atcacccata attaccaact gaggttaaac actgttaata   12600
tttgaataaa taaatattgc tgaagtaaat ggaaggtggg agaaggaaaa agatgactac  12660
aggtctggcc aagctaagag ataatgacag cattttttttt ttttttttaaa taggaaagct  12720 gggaaataca tttgattcag gggtagggat gacaagagtg gagctgaaac acaagtctct  12780
gacagaggca gtaaaaatag gaatcgtggg ggctgggcac agtggctcat gcctgtaatc  12840
ccagcacttt gggagggtga ggtgggtgga tcacgaggtc aagagatgga ggccaacctg  12900
gccaacatgg tgaaaccccca tctctactaa aaatacaaac attagctggg catggtggtg  12960
cacgcctgta gtcccagcta ctcgagaagc tgaggcagga gaaccacttg aacccaggag  13020
gcagaagctg cagtgagccg agattgcacc actgtactcc agcctggcta cagagcgaga  13080
ttccatctca aaaaaaaaaaa aagtaggaat catgggcata aaggtattaa cggaagctaa  13140
gaaagtggca gcagcacagt ctaaggtcac tgcttgcagt ccccactcat tctgactccc  13200
tgctgacagg cttccttcct tcttcagcat ctgacctgac actgggcctc aggcaccagc  13260
atgataggca gaaaagtgtc cgtacagtta ccagggtggt tgaagaaaca atttatctct  13320
ttgagtttgc cagaagattc atctatttag cccttggcaa ctcagaacac tgacaagtta  13380
tttttactct ccccattaat aaggtcaata gtccatattg aaacatccta ctggtcagga  13440
agagattaaa aggaaacagc tatctgagcc ctattctcaa aattttgagc aagtttatat  13500
atcttttcta tatcatgagt actctcaata actaactgcc ctaaactaaa ccaacaaagt  13560
acatggcttt ttaaaatagc tctttttatat tttataaaac attaagagat tttaggaatg  13620
```

```
ctatcaagag tcaagaaaat cttgaagaag ttcctagttc taaaagttac taatatattg   13680
tattcgactt aatgggtcta atctacatga gagacatcta tgtctcatct actttgatga   13740
tggttagtca ccatatctgt aaagacttaa agagatcttg ttatatataa cataaggaaa   13800
agcaaatgtt acagaccttt attgtctgct gctataaatc ccaggatgtt ttcatgacgt   13860
aacattacag tttgataaat ctctgcctca cggaaccacg aacgttcttc tctagaggag   13920
aatatcttaa cagcaacttc ttctccccgc cactttcctc tccaaacttc tccaaatcga   13980
cctttgccaa tgcttccttg taacacaata gttctcgcaa ttgttctctg aacaagcaat   14040
ggtaaaccta aaggtaaaaa taaatagtac tcaacacaat caacaatatt acatgtttca   14100
aacatcatga taggcactaa tgagtgaccc agaaaactga tactttaagc tatccctta   14160 ggaatttatc tcactgggga gatattatat ttgcaataaa ataactaatt aaaaaaggaa   14220
aataagataa taaatataat aaaagaatcc agaaactcct gctagagggt caaggtaggc   14280
tttgtaaaag taagttgaat tttgactatc ccttaagtac ggtggttagg caggaagaat   14340
gtgcaggcaa aggtagaggg aaatgaatga cacatttta gggaagcagc ttgggcaatc   14400
agagagagga tatatgtggc aaagcagtga aaagagaaag taagctgtca ccagaagatg   14460
aagagtactg aataccaagc tcaaaataac caatgaagag ctttaggtaa aagaggaacc   14520
tttaaagatt tctgagaaaa agggccatgg ctggaagcaa gataatttta aaatcttatt   14580
ttagaaagat gaatctcgta acagtttcac tgatgggagg aaaaaaggat gtgaacgcag   14640
aaacacagaa gtaaattctg ctttttgat aagtcagtaa aaatcaccac agaaactatt   14700
tcaaggaaag caatttactt gctgacaact ggctacatag acaacactag tatcttgaag   14760
aacaaggcta agtaacttac cttggtaatg gagcactgtt tttccactaa tggaacttgg   14820 cttctccaa aatatgtatt tttaagtatt gccatactta cttcatttaa aagggtttac   14880
taacttacct gcaacattta agtggcacta tatgtgagac catcacttaa tatcctatcc   14940
accatccggt aagtgtcatt ttaaattaca ttgacactaa caaagaaaat gccagtgtac   15000
atcatgttcc tcactcatat cttatttata caatctatgt acatataaat tggtgtcatt   15060
tataatctat actcaaagct gcttactaga tcaaattaac ccaatgacag taaatgaaat   15120
tatctgctct ctttggttcc ctgatgtgaa atgcttataa atccaaacgt taaatctta   15180 aagcgatcag aagctcttct tcttaagttt ctcaaacggg tcctttcttc ctcttgctct   15240
accctcccca cctcctgtaa agtagttagc agtataacta taaataactg tttgtgttta   15300
taaggaggct gctagttaga aacagatctg tcagaaatcc ttatttaaat catagagctc   15360
tttcgcacta tgtataatca attctaatta tgttgtttag tgtagatact aatttattac   15420
attttatgaa agccttgtag agggccacac cacagactta aaagtacact taagagttaa   15480
tttcaggaga ctaatctgga aattgcaaag acaagtaata aaaagaaaa aggaatcaca   15540 aacacaaatt ctgaaaacac ctgacaggtt caggacttgt gtaaatggta tggtcaagaa   15600
aggccaacag gacgaggaaa ggttttgtct tcccctttat cactggattc tagatgtcaa   15660
ttaaaattaa aaagcaaatc ttgatccact gtattatcta tattggatta cttcacatga   15720
atagttgagc atttttaaaa agttaacaat tggccaggca cagtgactca cacctctaat   15780
cccagcactt taggaggccg acgtggttgg atcactagag atcaggagtt caagatcagc   15840
ctggccaaca tggtgaaacc tggtctctaa taaatataca aaaattagct gggcatggtg   15900
gtgcacacct gtaatcccag ctactcagga ggctgaggca ggagaattgc ttgaacccgg   15960
gaggtgaagg ctgcagagag ctgagatccc accactgcac tccagcctgg gcaacagagt   16020
```

```
gaaactccgt ctccaaaaaa aaaaaaaaaa aaagtaacaa ttttcttcta aagacaaaac   16080
tgaataggcc taatttagat ctctatattc tctgctctac tcttctgtac ctttagaact   16140
gtttgagaga aaacttcaaa agggaaacag ggactccaca gctttacatg cagtgaacag   16200
gaaataagac ccgaacaaca tgcatatatt acaagagctc ataagctgca cacgccataa   16260
caaacactgg cctagaagac tcacttacaa aagctggcac atatgcacat gtgcacactc   16320
acacacttgg cgtacagctg ccagaaccca gctcttcatt gtattccctg aagttcccaa   16380
gttaaaagca cagtctttag aggtagagac agggcctttc cttaattatg gtcacggtac   16440
taagtaataa acatatgaat tcagaatgtg aaatgcttat acctttttcct caattaatga   16500 aagaactaaa aacagagtat tacaaacaca cagtttactt attcacaggc actagtctca   16560
tgcctaaggt ggcattaagg atttataatg aatagaaggg aaacagatgg cattttctgc   16620
tattattcac cagaagatgg cttctgcctg gataggtttg gagggaattc agtacacaat   16680
gaactatgac aggcaaagga ggccttaaac taagttttgt acaatgtggt caactgatac   16740
tgtatgttag attttttcctc caagtatgtt ttcaataaga gtaacacttg tcatttggac   16800
ataactctac aatttaccaa gtgctttcat gcaaacattt tgtcttgctt gaactcacaa   16860
caatccaatg atgtgcacag aatccatcac tttcatttta aagatgaaat aactcaagca   16920
tgagacattg gttaactgcc caaagccaca gagctagcaa gcaatgcaga caagtttttg   16980
cagggtaagg catcaaagga gggagagaag cttcagaga acagagagct atggtccctc   17040
atggatctag aaatatatat atatatatat atatatatat atatatatat atatatatat   17100
ataatggaaa cagaattatt ccattgtttc tcatgtttat atcttaaaag gttaatgaag   17160
atattcttat ccagtaatca actgccaccc acccaccaat tcctttaatc agttaggtgg   17220
gcttattcca ctgtggcaag tggcatgagt gctgtgtctt tccggagtat aagtttagaa   17280
acaagagaac aggtttgagg gattaattcc aaatatctgt agccatcctg attttctgtg   17340
actctggtcc ttgattatca cagttttgag caggatgact tccagaatga gcaaaatctt   17400
tttgaagatc tgaactgaga ataaatggga agtcccagga aagctctaaa ataacctctg   17460
tccaccaggc ctgcctaaag actatcacac cttcagtact aagactgctt catctaagtc   17520
caaactctca ttgtcttcct tgcacaactg tttcaggaat ccctaagctt gccttctggg   17580
acgtgagctc cagtgcgagc ctgtgtgtgt cctagtagtc aaggagagag ctctcttatt   17640
gaatacatat ggccaaattc tatagaagaa taattcaggt aataaaatca gtttcttcat   17700
tcttaaatga atggatatgc atacatacca atatatattc atttccttaa aataaataga   17760
catttgtcat tatatgagct ttctgcaaca ttagatgtga ttttatgctt cagaattata   17820
ttcttaccca gtcacaactt ctgctttaac attcctttaa tatcactcaa ttataaaatt   17880
agtgaaaatt ttttttttt tttttttta gatggagtct gtttcccagg ctggagtgca   17940
gtggtgcgat ctcagctaac tgcaacctcc accccccagg ttcaggtgat tctcctgtct   18000
cggcctcccg agtagctggg actacaggcg catgccacta cgcccggcta atttttttgc   18060 attttttaata gagatgggct ttcaccaaaa ttagtgaaat tttcattata tacgctttac   18120
aaattttcac tttattcatg aatttagccc ttatttgaag atgactcata cttttcaaag   18180
gatagtacat ctcatttaaa agtcttaaca aaccacttga agtgttttta tcaacagtat   18240
gggttccata ttttttgatga ggaaacagaa gcccaaagag gaaacatgtt ctaaccaagg   18300
ttatacagcc aatcaatgac aaagcttgcc ttgaaaccta gatctattta ttcttcacca   18360
agtgtcaaat tctaaaaaca caggggatag gagtgttcct ctcttaatat ttttccaaac   18420
```

```
cacatacatg caagaaaaag taaaagataa cccccttttca gtttaaacat gaagcactgc  18480
tatgccaaaa tccaccttgg gatgactctg acaattagct catctacttc tgatgccaca  18540
aatatcaaca aatagaactg agaaaagaaa acgtcattag gggccaaaac tacattaaat  18600
aagaaggtgg ttagacattt ttctcaagtg agaaaatgac ataagagttc attagtttaa  18660
ttttaaaaaa ccaggcctat acgaaagaca atttcatata atgttttaaaa agtaaataac  18720
cttcacaatt ctgaatacat ttctgtcatg cctgttttca aatgtaaaca tcaagctgct  18780
aaacaatcct gaatagaatg ggttagctgc agatcatgtg aatatctttg accttcagct  18840
tcatctatat gagaataatt gttcttatcc tttctacctc acagtgatga aaagcaaatt  18900
agattataca agtgagaacg ctttgaaatt tataccacca tggagctgac ttattgattc  18960
gctttaacag ttaaagttaa gttccaatct attttaaacc agccacagtc atatatacat  19020
caagcttaaa gatttttatt aggttcaaac ctgcaatatt atttatacta tctcacattc  19080
tagcaagttg gcttattaga aaactaataa aataagtatc gcttaatttt aaaaagatgt  19140
cttaggaaaa aggagaaaca attatgttac ctgagccaga acctgacgtt gtcatatcat  19200
aaattaagtc tttcaacgta gtaccctctg aaataaaagg gcgatctaat gaagggtcct  19260
cttcatttgg cactcgatgg tgaatgacag tgcggttgtg gcagatatag accatcaaca  19320
tgagtgagat gcagacgaag cacactggtc cagcaatgac agctgccagt tccacaggac  19380
caaggccagg tgatgacttt actgaaaaag ggcctcgagt gaaataaaca tcaacaacga  19440
caaaaacact gtaggtggca accccatttt tcccaatcct acacaattcc tgcagctggc  19500
cactgccacc acttagccaa agagcctcat tacagcagtt tacagggctc aaacccagaa  19560
caagtgaatc agtcttctcc cactaggcct cctttatgc acaccagctc tgtcagcacc  19620
cacttactcc tgtattcttc agccatcatt acaaggccaa ctgccgccaa tatcatagga  19680
ccttccccac ttatcacatc aggtcactaa taccaataac ctgtaacaat acctattaac  19740
atctccttaa aaatcatatt ttttttaatg tttggcttgt cttcttgttc caaggccagt  19800
acatgctcat agcaagaaaa acaacaacaa aaaaaacaac aaaatatcaa aacaagcgaa  19860
aaaaaaaacc acatacatct tcatcacttc taaacaactc acatttcagt atatatctct  19920
ccaccaattt ttttttttt tgagatggat tttcactctt gttgcccagg ctggagtaca  19980
gtggtatgat gttggctcac tgcaacctcc gcctcccggg ttcaagcgat tctcctgcct  20040
gagcctccca gtagctggg attacaggca tgtgccacca cacctggcta attttttgtat  20100
cttaatagag acggggtttc accatgttgc tcaggctggt ctcgaacccc taacctcaag  20160
tgatccacct accttggctt cccaaagtgc tgggattaca ggcatgagcc atgcccggcc  20220
aataggtcca ccaatttttt aaaggcagaa catatctttt actttttttt tttaacagag  20280
tttgcatata tactttttt atactatctt aacctcctgg acttttaagt ccagatcatt  20340
ttcttgtaac ttctattaat aattaagatt ttctggttgt ttcagaaaat tacaattatt  20400
ttgacattca tcctgagtct tactggttta ctgcttacca ccatttcttt catatcacat  20460
ctttcccatt cttaagatct tcagtagatt aatctcttat catacagaat cctatttcta  20520
gtaatttctt tcaggaagag tccatgcacc cttgtacact gaacttagtt gtggcaagaa  20580
ggctgttgcc tttgtatatg aaaaatcttg gcctatttca agaattttag gtgatcgtaa  20640
aaatgttcca tttgcccttt gatatttaag cagaaaatct gaacctgttt ttttttttca  20700
ccttttacag gtaaccaatg tttatgtgtg ttaaatgctt atataattct tttattcttg  20760
aaattgatac ttttttattat atgtgtttgg attaatattt tttcattaat tttgcctggt  20820
```

```
attctgtctt ctttatgatt tcatgccttt ttctggaatt ctgataataa gcatattgga   20880
tcatctaaat ctgttcccta tatctcttaa tatgctcacc aactgtcttt tctctgaatt   20940
gtaacacagt ttcttaaaac ttgtcccaaa cttgactata aaattatggc atccagtctg   21000
ttgttcgctc tcaatagtgc attttttaaaa acattcatca gttgggcttt tcttctgaaa   21060 gcaacctttta acaactgtga aatgttctca tttcatagtg aataactgaa aatagaccct   21120
gtactgtttg aaagttcttc cctatcatgt ggtaaaccta tttcacagga tgacatctaa   21180
tctatctagt tcagactact tcttttgaac tcctaacttt tcattggtaa tttttttgctg   21240 tttgcttatc ctagagctgg aaatgagaag tttatatatg ttcattagaa acatgagaaa   21300
taaggtgact tcttcacaag gttttgtaaa tatctattca gatatttcaa gctcaaatga   21360
tggaaatggg aaattctgga attatccttt tctttgccac attataactg cagatgcttt   21420
catcaaagtc acaaagatat tgtagtccga ccaaccctta ccacagggga gctgcattat   21480
catgctgaac aggtggagga ctggcctttt ccttctgcgc tacagcagtg cttcctcctt   21540
taattagcac aaggcctgga ccaactttga gtggagagtg agcaactgtg tctgctcctc   21600
tgagcactga agccaggtgc ttcctaaaag ggaactgaga gtttgccccc atacccctaac   21660 ctcacccccc aaatcctttg tctaagttat tggctggact tttcgatgac taacctttct   21720
tatatggcta gtcaattctt tactagtctg gtgtcatctg tactgtaaat tgcagaagtt   21780
cctcacaagt gctggcatgt gggtggcatt ctaccattaa tcccactagc attaatacag   21840
gttgccctca tttttatatt cctttgggat ctggggaaag aggtaagagt taaatacatg   21900
tgctcagact tccatattaa accggaatct taaaattaaa aagtttatga agtcttcaaa   21960
ctgctggttc tgccaggaaa ttttatttat ttatttatta tcttttttttt ttagacagag   22020 cctcactctg tcacccaggc tggagtgcag tggcacaatc ttggctcact gcaacctctg   22080
cctcccaggt tcaaagattg ttgtgcctca gccacccaag taggtgggat tacaagcatg   22140
tgccaccatg cccagctaat ttttgttatt ttagtagaga tagggttttg ccatgttggc   22200
caggctggtc ttgaacttct ggcctcaagt gatctgccca cctcaggcct tccaaagtgc   22260
tgggattaca ggcatgagcc accgcaccca gccccaggaa attttaaatg taaactacag   22320
gtgaaggacc aaaaatctag aaatcatgta taattaattt acgcaaaaag atcataaaac   22380
aagctgaaat tacaaaatga aaacatctag actgttaagt gctgctctga atccccactc   22440
attaaaagac tgtgattgct ttaaaagata ggagcattat acaaggaaga agaaattcac   22500
tctgagaaca aagtagagac aatctgaaga tgttgttgtg ggctttgtca gagtttgctt   22560
ttatctatcc ttttaggtat aacagacctc agaggaagtc cacccctggaa ccaccttctt   22620 aaacaacaca tacccaggag gcaggatctt ggttactctt ataagtctgt aacaatggac   22680
aagtcacttc ttgcctctaa acggaatgag ctggattaga caattttttat gatcccttcc   22740 agttctaaaa tcacagagta tgaagagttt ttcttgtagt atctaggaaa aaaattttat   22800
acaacttacc agtagttgga agttctattt tattgcaatg gtcctgattg cagcaatatg   22860
ttgtagtcac agacccagtt tttgaagagg gtgcacatac aaacggccta tctcgaggaa   22920
ttaagtcaat ttcagctata cacatgctgt tgtgtataac tttgtctgtg gtctctgtga   22980
cagagacaaa gcagagccca tctgtcacac aagtaaaatt gtcttttgta cagaggtggc   23040
agaaacactg taacgctgga aaagagaaa gattcttaga aaaatctca aggttaacag   23100 tttgaaatta tccaatattc acctctaata atacattctt gatcctatta tcacacaatt   23160
tctatgcact gtttgttgct cttagaagca aaaaacaact atttgttgct cttagaagtt   23220
```

```
tcaaattata ttaagaacca catacacgtg gaagcccaag gaaatgtagc aacatttgga    23280
cccaggtttt ttcctgaagt ttttttgcttc caagtataga aaaattttgt tatgttcaat   23340
ttcatcaaag caaggcaagc atttgccttc ccattagaaa caaagtacat ttaaatttgt    23400
aatggttata ctttttttttt tttttttttt tttttaccag gcccaaacta acattcaca    23460 tactcctcct ttgagaagca atgtgtgaaa acactaccac ccattaagtg taggctaatg    23520
ccatttcagt ggctttctgg ataatggagt aacggaaaca gatttgtact gagccagaca    23580
ctctctattc cccttggtgc aaaccctaaa aaagacatgt atattctggc caggactggg    23640
gcattctctt agggaagcca agcagactac acctgtaaca atacatacat gctccaacca    23700
cataggcaac ctaactacag aaatgactgg cagcaaaata ctagcttcat gcccacttgt    23760
atctacttga tctttatggc tcaacccag gagtgacctc tttagggaag ccttctaatt    23820
atcaccaaca ccttctcata cacacagata caccttcaac catgctctct gatgaagtta    23880
agtgctctcc aaaacacata ctgcttacca gaattgctag ttttgttttt ctttctccta    23940
tgaaactgta aactccttga ggccagatac ctgtattagt catttctgtc aatctgccat    24000
ctaacaccat gcctcatgca cagcagcatt caaaaaatac ttgttgaatc acaatgatag    24060
aatgtgtgca taatttcacc atggtcacat gaaattgcaa agcacagaca tgttcttaaa    24120
tccaaacatt ccaattactt gttggcaaag gaataaaaag gagtctaggt acacggaatg    24180
gccatctatg acgtgaacag caaggtccac tctacctaga aaaggagtgg ctaggcagac    24240
aggggcagga tagacagagc taactccctg aagagctaac ttgctgtaca agaaagggtt    24300
aactcagcag gactgagttg ctcaaaccct gcatattccc aagaaagact tgtcttcaaa    24360 actgccttg gctggctcct ggtagatgag ctctgaacct ttggaatatt ctccctgata    24420
agaatatttc tgtatgcctg aggccttggg tcacatggta ccaattttgt cagacagctt    24480
attctaacaa tgtgatttac agtgaacacc tattactgct ggggggccgg gtaggagaag    24540
tctgaggggc tgaagcctgt catgcagatg ctgcaagcct aagtgactga ccaacagtaa    24600
aaaccctgga caccaaggct caagcgaact tccctggttg acaacttcgt gcatgctgtc    24660
acacattgtt gttgagagaa ttaaggccat ctatgctatg ccactggaat gggacacctg    24720
gaaacctgtg tctgatttct cctagacttc accccgggtg ccttttgctt ttgctgatgt    24780
taactgtatg gttttgctgt aatacactat aaccatgact gtaacagctt ttctgagtcc    24840
tgtgagtcct tctagcaaac caagtctgag gatggccctg cagactccca actcacttgc    24900
tcaactcaaa ttcaggaatg tcaggttctc cctcaagtag ctgtttcttg gttgctggct    24960
taattcacat acttgtctat tatctttaca gaccagtaaa gttttacctt aatcattatt    25020
aaaaacgctt tctttattca tagacaggtc agctatttgc ttcctaagta tgaaagaaac    25080
tcaaggaaat gacaagaaag agacacaatc gtaataaaga ctgctaaaag agacagtaat    25140
tattcatgac aaggtgtgat ggtgatggct gtctgggtat gatttcctaa ggaggaattc    25200
tgaaccagga attcatggac tggcttcaga ggtacatgaa tcccataaaa ctataagcca    25260
aatgttatat gtatttacat tttcaaggaa aagcttccca agtcaatcac aatggagtct    25320
gtgacccaca aagcattaaa actaccaccg aaggacattg tcataattct ctcctaaatc    25380
ctctttactc atgattagtc attcaaccca tgttttctaa gcattacttt tatcagttac    25440
tctaccaaaa gcttagcaca caaagattaa taactaatgg tcacagcact tgaagagctc    25500
caatgacaag tgaaggagaa cactgtaata caatgtggta accgctatac ataaaaaata    25560
ttgccctgaa tactctccca gttctcagat caccatggct cccctatgct gatgagataa    25620
```

```
gggctaaaca cctagcctaa caagactttt agtttggggt tccaatttac ttctcacatg   25680
gcaaatgcta tctagggcca cacacctctc accattataa taataatgtc tttcatgacc   25740
ttggtcttta catataccat ctctctgtct agtttaaacc tatcttctta tctgactcat   25800
cctttaagac cctatttcaa caggatcttt gccattatgt gctctaaacc tcgcccttac   25860
cttcacaata attggtatct cctttcaata tgttccatag tgctctttgc atacctttag   25920
aacagcacaa atcaatctat ttatagcttg ctgttaaagg gtctttcatt gcctcaggaa   25980
gggccaagct tgttttgttt ttcacatctc tgaatcctgg ctccttagat agtgatcaga   26040
aaaatatttg ctaaaacaat gtctcccaaa tatgctggga gaaaaaaagg atgtataagt   26100
tgggtacaag gtttgagaac atattttcac ttcaaagata atctaaaaac aaggataaac   26160
attcaagatc atgagtagcc actgtctcaa cactggcact aggctttcac tgctgcttct   26220
tcagctgtgt gaagatcccc ttcaggccaa atgtccttgt ggcacactac acacagcata   26280
agtttcatgg tcattgtaaa agaaagagta aaaaataaag ggaatttgaa tcgaccatat   26340
ggcaatacag gcatggcatg catattcaaa agccaatagc ctaacagcca ataccatata   26400
tgtactttat tatatgcaag tgctatatgg gtcctacatg tgtagtacaa tttgcaaaca   26460
tttgttagca gtaaatataa ttgtaggtat gcaatgtttt tccattctca tttccagcaa   26520
taactggttt agaaaatcat ttaatgaaga tttcaataat gtcaagatat taaccttatc   26580
ttccaatgaa caaatggat gacatctcag taaaacttat aagcctgtat ttgaggaatg   26640
cttgctgtca agtgttttgg ttaggtatga tgtctcatcc tgaacttacc aacaaggcct   26700
tgaagtcatt aatgccctcc tgcataacat tactgatgag aagaggcact actcacagct   26760
tttattatca ctgaagttaa aatacagaaa cacatttaaa atggaattag acctaaagct   26820
atttttttct actgcaaaac ctaaacatca tctgtcacat ggaataattg tattcatttg   26880
aattttgttt tttttttgtag ttgtcttttgt atttaatttg cagatttggt ttatagtggt   26940
gtatgagcca agaacataag ggttttatat ctagtttcat gtctacagaa tttaagtaac   27000
attatgaaaa atacactctg tacttctcct ttcaaagagg tcattacatt acggtaaatt   27060
tgaaaaagtc agtactaaag ggttttttctt aactactctt tcaatcagaa gaggtcacta   27120
gacaaataaa aacatcaaga taacacaaag cttaactagg taaagatttc tctcttcagg   27180
gaattaaaaa attccatttc accacttgaa gtcagtcttg attgactaca agactgctgt   27240
tatgtgatac ggcaagatcg tttagggaaa aactaaaata agaacttaat ttttttccatg   27300
aacatgagtt ttaattgcca tttttttttaaa aaattcaaat ttatttttatt aatagataga   27360
tttggcccct ggatactgcc ccccccaacc ttttattcaa ctaggtttta aatttttaaa   27420
cgcatataca tggcaaaatt tcaatctaaa aaacgtaaac gaagacacct ccttccgcca   27480
gcccaaagcc caagttctcc tcactctgca acacatcacc ttgactcttt catttaattc   27540
tgcaattatt cactaagcat ctctatatgc caggtacagt gtgggctatg aggtgcagag   27600
atgagtaaga caaggtattt gcacttgagt agttcactag ggtggaaggg aaaggcatta   27660
aacagataat taaaatcctg agtcctgaga agaatgatca aagtgtttct actctgctgc   27720
ggtagaagag attatcaaga aaagcttcac cagcattcaa gtcagaactt ggagaatatg   27780
tacaatttgt tagatagata agggtgagaa agctttcctg actgggtttt ctttctcagt   27840
ggcaggattt catccttagt ggctggcata ccaagtaaga tgatcaaatt taaattgttc   27900
aagatgctaa ctacgatgtt ttatttcatc aggaaaataa acataatacc tctctgacct   27960
atttcatcat ctgagctaat caaatgagat actgtacttt attaacacat ttggaaacga   28020
```

```
acataaatga ttatataaac acacagaatt atcccatatg ataaatggca ttgtgccaat    28080
gtggttttta ttcgtaggcc accaaaggta aacttcttcc caaaagtagt gacaaaattc    28140
cactgtagaa tcccagacta acagaaccac atgaaacttt gaatatcatc taggcaattc    28200
agttctgtca ttttattaat gtagaaacca aaacttaaga aaagcaaaac aattttaaaa    28260
attttaaaaa gaaaaccaaa aaaccaaaat gatttataca aatattctac ccagattaca    28320
ggcggatgtg aatcctcact atattatcac cagcccacga gtgaaaccta cgcaactatt    28380
tgctatacca ctatccccat gctaagtaac cctgaacttt aaagactccc aggtggacct    28440
gatttggttt agactcctac agttttgact cttctgcttg atagcaaaaa taagaaccaa    28500
atcccctgtt taggacccttt ctactacact gtccaacttt gtttccatgc cccagtcttt    28560
aacagtgggc atagctttct taatcttgag atgcacattt ctctaagctt tacatttcta    28620
aaatctgaat acaatttaca atcaaagtaa aaagaaaact ccagcctcca gactgaaagg    28680
ttaagacatg atgggttgtt gtaacctatg tatgtgcaaa cttggctata catagaaaag    28740
attacaagtt gagtatccct catgcaaaat gctcaggacc agaagtgttt tggatttggg    28800 attttttttca gattttggaa tatttgcata tacataatga gacatcttgg gaatgggacc    28860
caagtctaag tataaaattc attcatgttt catatatgct ttatatatat agtctgaagg    28920
taatttaata taatatttga aataattttg agcatgaaac aaaggtcatg ttaagtactt    28980
atgtgcagaa ttttccactt gtggcatcat gttggtgtgc tcaaaaggtt ttgaatttca    29040
gattgggatg tttgacttgt attcacttca ccatcactgt aattatttgt cttgatagct    29100
cccttgcaac tataacttag gttaaacaag gatttcagtg tgattcagca ctaaaaggaa    29160
aagctactgt gtacacagaa aattatatca gaaccatgcc aggaaataca attactagca    29220
gtgaaatttc caaatattgc agaataaatc agaattttca aagtttgcag atgttagcat    29280
ggtgacagtt agtaccaaag gaagtgacat gaggaaaaag agacaacagg acccttgggg    29340
ttattattca tggtattata gtatcggggt aacaactctc ggggtaacat atcccaagtt    29400
gagatcttgg ctcttggtcc caatataaag gatttccttg gttgcctcat ttcagtacgt    29460
ctcgaggtca catatggaag cactattaat tctatctaat gccagggcta cccagggtta    29520
attcacaagc ccatatgtct tgctagaaaa gctgagaggt aaacagttgt gtatagtatt    29580
aatatatgga acagatattt ctatcaccct tgttaaagaa ataaaaatta gcaccgaaac    29640
cttgtcttcc caggcttagt gtgtcatcat ctacacaacc tacccgtagt cttttttatgc   29700 atacgcttga atactctttc ctttttcaac ccttgttact ggccctctcc agccttctat    29760
cacccatctt cctccagttc agagctcaac tgaaatctct ctttgaaatt cactagcaat    29820
gcccttctgg tcaaattcaa tattcttttc aaaacgtttc aggatatgag acagagtacc    29880
accctttctt tattagtttt tatatgacac taaacttccc aaacttactt tgcacttggc    29940
cctttggtac atctcagatg tacatctcca agcctcttgg ccttttacct gtgctccaag    30000
cttgtatttt aactacatcc aggaaacact ctgcttggct tacttatcta tgcaaagtca    30060
agcagagtgt tgtaatccag ttttttcatc actctgactt tgctggtgat gacccttatt    30120
ttcctcaccc tacccactac agcacaacta tacttttctt cgcagtgaga gtatttccaa    30180
atattacaaa catgtaccaa caggcaagta aaagacctaa catgcacaat gtcctttatg    30240
cagtttgctt cactacagct gaaagcagat cacatcactg ctggcaaagg tgaaggcaaa    30300
agttggaagt tatttaaaaa aaactttcag ggactaatgt cagcccctttt tatcatccaa   30360 cctattcttc taccccagtt cttctgagta atctgcctta cccctttttct ccattctcaa   30420
```

```
cacatgcccc cttctcaagg agacgtgtcc tctttctcc ctcatccagc tttggagtaa    30480
agcatactat atagattctc cttttctttt tattaaatat gttgcttatc tctgtataca    30540
tggctaaaac cctgacctcc aattccctcc agcctactat cctaggtttt gttcctcaaa    30600
atactcagtt cttctcaatt caaccctcct ggggctacct tgcagcagta atatcaaagt    30660
aagcttgtca aaatagagaa caccatataa tgtacataaa attttcctct agtccagata    30720
atatttcacc cctgaattta gggcatcaga ataaacgcct gattttttc cagataaatt    30780 ccatttactt ctgccacttt taaagaattt aagatgcatt gtttatcatt taacccacat    30840
cacatcttaa aagaacaggg cactcccaaa ttcacaagct cttgttttc cacattatct    30900 tcattttcca gtctcctagt ttctatggaa ttagccaata taatgttaac tgatatcaga    30960
gaaaacacac taagaatagg ctgcccaaat ggcaagatgg gatttaacag ggtaactaat    31020
acaaaggctt tcacttagat tcgaaataaa tcacacaagt acagcataaa gatctggtta    31080
gcagatctga ggagtttaac aacacatttt agaagagtca gagcctttaa aaagtatctt    31140
ttaatccatc aattctacta cttacagttg tctgaggaaa caataggtga gagcaaaaat    31200
ctaaacttgc agatgttcat tacagtattt tatgattgaa acaacctat gtgaatgaca    31260 atacaatgac agaatgaatc cttatacaat cataaatgaa agactatata gccattaaaa    31320
ctggtatttt agaagcatgt ttaaggacaa gggaatggtc ctactactaa agggcaggaa    31380
gtaaagctgt atagtgtgat tacaattaca gtcctgtcaa gtgaccttgt ttttgttcca    31440
cttcaatgag ttgaggggat attttaatat acagagcaga tgtgcacact ttgccttacc    31500
ccaggccctg aaaagaaatg gagaaacttc tatgtctaaa ggtgagtgct aaaacaataa    31560
ccaaatttct tatttcctct caatctaagt atgcttttac acagtttctt attagatttt    31620
aatttgacta gtgggtaggt attataagga tatggtagtt aagttgatgg aactcagaga    31680
cagaaaaact taagttaaaa tcctatcttt gccagtcagg cactgagtaa tcctgaggaa    31740
gtcacttaac ttatttgaac ctaaatttct tcaacttact tcctaaattt ataacatact    31800
aacaaacagt accaatctca gaaggtttga gggttaatga aataacatac atagaatact    31860
tagcacagtg cccagcacat aataaaatgt tcaaaaatta gtttatgcac ttttttcaaca    31920 agtatttctt tggagctcct attacgtgcc agtctctggt ctagatgcta gacagagaat    31980
cagagctaat gttgagacag ctctggtagg caatactgac acagaacaca atataaacca    32040
tatgcatata caacagtgaa tgttcatggt acctatcagc tctttctcct tcataaatat    32100
tcatacagtt tttcaacaat atgactgaac agacctggct caagaacttc actacagtag    32160
cagtaggcac acacagaaag tatattttca gttccaaccc aaattaacag tgtagggaca    32220
cacccagtgt gtatatgtaa tatccctaat aaataagtta atatctaatt agccataaaa    32280
tgttcatgct ggaaggaata tgaacagaaa tatcagatcc cagctccttt agagatgaag    32340
aaacagaaat gtcctaacag ttacatcaac ataatctaga tttattccaa aagtacacaa    32400
agaaaaaaag gattacttga taatctacag tgatttccac ccctactccc cacaacccct    32460
cacgtaggac aaaaccgaaa atttcaacct ttcccttgg aaagcacgag tggctgtagg    32520
agagactggc ttggttgcac agataataag gtgtaataat gaacgtaaat gaaagtggct    32580
gatcatcctg ggctagggga atgacataca aaacagaact gtggtagaga aggaactgtg    32640
gtaagagaag gaagtggtaa ccactcccag ctgccattga ctcggggcag aggagagcaa    32700
tacctggggc agcaaacagc gaaagatctg ttggagccac agttgaagaa atgaactgat    32760
ggtcctgggc agttagtaat tttagaagca gaaagcaagg cctgaacacc ttttctcaga    32820
```

```
acacaacagt gaatgtaacc tgtgtaggaa gaaagaaaaa acctttagga ggatagagat  32880
aattaggatt gagattcctg ccctcagatt cacaatgcag agaacacacc actgataaat  32940
gatgatgcaa agtgcacaga tcagaggaca gaaaagggag atttctctga aatatgacac  33000
ctaaactaag acttaaggaa agctagtgaa gaaaggaaag tcattttagg tagaggatat  33060
acaaaaacat tgtacaaaag atgccaaaat aaaagtttga gccaggtgtg gtggcacgca  33120
cctgtagtcc cagctatttg ggaggctggg gcacaaggat cacttgagcc ccaggagttt  33180
gaggctgcag tgagccatga tcaggccaca gcactccatc ctgggcaaca gagtgagatc  33240
ctgtctcaaa aaaaaaaaa aaaaaagaa agaaacagt aagggagttt ggcagtttag  33300
gtgatgtaaa caaaaacaaa aaaactgata aaattcaaca gctattcatg atttttaaaa  33360
atcttagtaa actgataaaa ttcaacagct attcatgata tttaaaaatt tcagtaaatt  33420
gcagaattta aaaaaaattc tgaaataatc agattaaata aaaggcataa agtaggcat   33480 tacatttaat gttgcatgac tgtcattttc ccttgaaatc acaataaga aagagatatc   33540 catcactact tctcaacatt gtattagaag tctgagtgta gtaagtcaga aataaacaaa  33600
aggaagatag actggaaaga cacagaacta tcattacttg cagaggacaa ctatgtacat  33660
ggaaaatcca aaagtgacct acagatcaac tattagaatc aattagtcaa tctagcaagg  33720
tcactaatat aaggttactc actataccaa aaaaaattaa attaaaaaat cattcttaaa  33780
ccagtaataa atagaaaacg ttttttaaaa atctaaaaac taggaataaa cctaacaaaa  33840
gacaggtaaa gacctctgca gagaaagctt aaaaaatatt acttattgat agaaattaca  33900
aaggagataa aataaaattt taaaatgtat ttataaatgg agaaaagtga caagttccta  33960
actggaagat tcaatactgt aaagaggtca atattccata aagtgatctg tagattcaat  34020
aaaatcaaat cagaatcccc acagggtttt tttattcagt gggaactgac aagttgattc  34080
tgaaatttat atgaaaaac aacatcgcaa gaataaccaa agcaatcttt gaaagactta  34140
acactactcg atatcaagac tcctaacatc ataataatta agacagtatg gtaatggcac  34200
aaggacaaat gggcaaacag aacagagatt acagagaaac agaccctcac atatacaacc  34260
tcttgattta tgatgaaggt gattgtacac tgggggaaaa aaggttttac caataaatgg  34320
ttctgagtca accagatatc cgtatttaa aaataataaa atctcatac cataataaat   34380 aaccaactcc agatacatct caatgtgaga ggtaaaacca atcttttaaa tgaaaacaca  34440
ggaaaacatt tttaaaacat tgggtcaga aaaagtaagc aaacaggatt ctaacttaaa   34500
gcaaaaaatt gaaggccggg cacggtggct cacgctgtaa tcccaatact tgggaggcc   34560 gaggcaggca gatcacctga ggtcaggaat tcgacaccag cctggccaac acggtgaaac  34620
cccatctcta ctaaaaatac aaaaaaaaaa aaaaaatag ccaggcgtgg tggcagatgc   34680
ctgtaatccc agctacacgg gaggctgaga caggagaatc acttgaaccc aggaggcaga  34740
ggttgcagtg agccaagatc gcgccactgc attccagcct gggtgacaac agtgagactc  34800
cgtctcatct gaaacattca tctcccttgt caaacaaaat accaaagcaa agcagttaaa  34860
ttgtggttgc agtctcctag aagaacacag ctgaattgaa ccaagcaagg acagaaaagc  34920
ccaccaaaag gaaggagctt ttgtattatt tctatatttg catttttata atattttaa   34980 tcattaaatt ttggactccc ttggagccta agatataag catctagtgt tgactgaact   35040
cctttcaggg aaacatttgc cctttgagac taaactatgt gtatatgaaa acttaggctt  35100
gagatgtact gtaccaagc taataaagtt ttcagacctc aaaatctaca tgccgagact  35160
tggcattagg aatatgggtt tccaattgct ggtagcattg atacagtagc atcatggcta  35220
```

```
ctgaagaaag tgggggttg gttattaaaa gataaggatc tatcaggctc agaggcataa    35280
gggtcttgat gttatttata ccttggataa ctgatgatac aacaccgaag actatcttgc    35340
agaattatga aatctatatg taagtcaata atcactagtc tctagataat agtttagaat    35400
ggttcacagg tgattatact catttcttcc ataagatttt ccttttccc agttacagag     35460 actaagctaa atcagatgga agcacccaat tgcttagggc aactacgcta tttcctcagg    35520
gacacaccat ctgtttgcaa tgcacagcta attctgagcc tgttggtcct cgcagagttt    35580
tcccttaaga cttctgcctg atgcctaaaa tcccttaaaa ctcctccctc ctttcccttc    35640
tcccatggta aggcaagagc aggctggatc tgacaaaact taaatgatag atgagatcta    35700
cataaaatac ttatgtggcc tttttttttt ttttaagaa taaagtgaag aaacaattat     35760
gatcatgggg agaaagaatg tgagagcaga aaggctcaag tttatacatg catcgaaata    35820
agagggaaga aaacaaaagg acaatgcacc atggaaagaa ggaaagcaaa ataatggaaa    35880
gggagaaaaa aggagcatct cttcctagga aagtaatcta caatgctgtg ttaatctgcc    35940
aacgctttgg tgggactggc aatcagaaat tgtctttcct cactgacaaa catgaccaga    36000
ctctggcccc tgatttgtaa tttttttccc aaatgtaaaa tgagacaaaa taactaaaac    36060
tactttaact tgtttatttt gataaaataa ttatatataa ttattgttga aggaaatcta    36120
caatacacaa tcttgggtgt ttttatttaa atctatcaca cattgaataa caaaattaaa    36180
atgtcagttt ttcaactgga gaaagtactc aaatcaacaa ccacgtgctg aacaaagaga    36240
cccaattaga gcacattata gtttgatttg gaaatgaata catcaagcaa aaaataaaaa    36300
acccatacat atatcgtgtg cttgcataca aatgaaaggg cagttgctgc ttttctatct    36360
ctgtatgtct tttcaagttt aactctatcc tccatgttca gtgctcccaa atatctatat    36420
tagtcctagt ttctcgcaga aaaagccatt cgttttttgcc ttttccctgg ggacctatt    36480 gtaattcaat gcatatttaa gaatcttata atgtagaaat gtaacaggat gcctgaagaa    36540
ggtgtcctag aactataaat atacactatt atgtaatcag tgaggtttac acctaggaaa    36600
tctagatgga atggttttcc tgaagcaaat gaacaaaaat aaggaggttc agtcttggtg    36660
gtgagaacaa ggaaacactg aacagacct gaagtagtac agcaactgca gaaaaagga    36720 aaagtgaatc cttacaaatc atgagtgata aacccgaatt gttcacttta tttttcaatg    36780
gcccatgtac aaagacttct ataaaagctt ctgctcaaga acagagagaa gcttgttttt    36840
cccaatgaaa tcagaatgct tctaaccaca gaatgccctc atgctaatgt acgtgcctat    36900
cttttccatg aatactggga ttactgtgag accagtacag tagggccaca ctctcagata    36960
agtgtggtct ctcctaaagt aatcattccg aacgtccatt actcagaaat gaagcagttc    37020
ttcaaacaag aaacccaagc aaagacactc tggatcttac tgacttgcac ctgtttgaag    37080
gtaaatgtct ggctctgcct ttggtagcag tactctgatg aagtgtatca aatggagaca    37140
caccaaaaga taagggcatg agaaaaatgt ctttgtaagc cagactaaat agtttcatgt    37200
tgctctctat tcattatcct ccagcttta gcaaagcttg atttaaatgt cctagcctta    37260
catcagctgt tccattggca ttagggaaag actaatgtgt tcatacttgg atcagagact    37320
taaactggag aagaaagatg gaggcagcag cactaaattg aaccctcaat acgtgttaaa    37380
ggggaagcct cagaacaaga atcagattat tgccagatcc agcaataacc ccttaccact    37440
tggagattct ccctgtatga caatcttggc atttggggct ccactttatt aaggaaggtg    37500
gcagtctcct catgaattct cgataggcaa tgagatctat gcaaattatc agtcttcctt    37560
acttgccttg gttaccagaa aactcagagc taagtattgt gttcaacttc taaagctttc    37620
```

```
ctcagctaaa cttacggata attgttctct ttttctttcc cttttttgact tactgattct   37680
tatcttttgt ggtcagtaga tttggtctta ctgaatttgc tattatttca agcttccaaa   37740
atccttttt  ggaaaatgac caaaataaaa gccaatcaat ggataaacta acttttctcg   37800
tataatacag gagcaacaag atactgctca tcttgaagcc atgaatccta gggatattta   37860
gactatattt ggctaaaacc agtaagcaag gaagcttgga ttatgcccaa aagtacagaa   37920
ttttagagga gaaacagagc ttagagataa acaagtccga cctcctacct aatgtaagaa   37980
attccttcta caatttctca gacagaaggt tatctagcct ctgcctgaat agttccaggg   38040
tgacagggaa catactacct tacaatgttc cattttgaca gctatggtag agagtcattc   38100
cttacattga gctgaattct gcctttcagt ctaccaatta attctagttc ttcattacac   38160
agacatgtat ttcttctttc agaagacatt ctttcactta tttaaatata taataattcc   38220
cctttattga acacctactg gtgtcaggct atgtactaag tgtaaatact actgtacact   38280
atcttcacaa cgatcaggta aattaggaac tatcctcttt tgaaaagtga gtcacagata   38340
cactgattag actctaatta cagccagata tgttggtgct tatatactac tcctataaac   38400
aaatatttca ttaaatttct gacaaccaag tcacatgaat ttaatctgcc ttcaaaactg   38460
aaagaaaaac ttaagttaga tcaatccaaa tagaaaaaga gagatggtct agggatacaa   38520
ctgcaccagt gtttggttca ttgagaaaaa caacaggaaa agcatttaaa aggatagcca   38580
tcagggagct ccaggagata gtaaagctga cacctgtaac atcagcaacc atgacctgag   38640
gcctaggccg caagcaggaa acttcctctc ttttatctca gccaagaacc acactcccaa   38700
aagatcaaac gcattactgc agagaaagca gcactgtctg aaggttaatt tcaatacaac   38760
cagaagatca caagtaattc tgaatatata catctttact aagagaggtg ggggaaaaat   38820
agcatgaacc tgcaaaacag gaaagaacca tatcccagca aacggaccag gactccagat   38880
acaagctagg acttcagggt ctaaataaaa actccattta aggtagcgtt ttaggacact   38940
agaatcctcc tacccccaaa agagaaagac agagagagag agagagaata tgaggtgaat   39000
gctagatgct agtagccatt tctttgctta aggtgctctc ccatttccaa ctaggttcca   39060
ttttttttta atctttgctg actactgagc aattttattt ggctaccttc acctcaaact   39120
caacatgctt aaaccagaat tcgtctcccc ttaatcctcg tgccaaatta ctcattaagt   39180
taaaggcatt atccagccta aaaaagcttg gagtcattct ttttctttc  atggagtcac   39240
tctgaatttc tgtactccac ctcttttacag ctaagaccta ctgccactca acaaatattt   39300
actgagtgcc taggatgcac caggcacttt ccatacactt gagatacatt agtgaacaaa   39360
acgaagacat ccactttcac aaagcataga atgataggaa ggagacaata aacagtaaat   39420
aagtacatat gataagtaaa taaatacagt atgttagaag gtattgttac agagaaggaa   39480
agcactgtag gatgatgaca atattttaaa aggtggcagg ataagcctca ctgagaaaaa   39540
ggtgtcatct gagcaaagac ttgcaggagg tgagggagga agccatgcag gtatgtgagg   39600
gaagagcaca caagcaaggg aacagccaca cacaggccct actactaatt cctctgattt   39660
ctttgtttca aatgtcatac agtcaccatt tcaccccgtt ctcaatgcca tcaaaccaac   39720
tgggtagcca ccctgatcca ttccctctgc ggcacaatta gacattcttt ttccacatta   39780
aaaccactct cctgattttc aaggcccata attctctgag cccaccctt  acaccatgaa   39840
cttccatttc tcctcttaga aatcctgaaa cttagaatgc tctttctcca cacatgccat   39900
cctctccagc caagaagtgc ctcctttcca ccacacatcc actcaaagcc ctatcctcct   39960
gcaaggcaga gagatcaagt cctacctcct ctgtaaagca gtccctgtgg ttgctagtac   40020
```

```
tgagtctgta gtcatatttc ctcagcatca attttttcaa aagcaagact gcctcttact   40080
tttcctatat ttctcatcat gttgatcact actaaatatt tgctaagaat agatgagcta   40140
tttcctctgt aaactgaagc tctttcctct gtaaactgaa gctgtttgtc aatttaaaca   40200
cttttattag ctttcataaa ctgctgaaat agaatgatta agaatggtt  tgttgctgtt   40260 tttttgtttg tttgttttg  ttgagatgga gtttcactct gtcgcccggg ctggagtgca   40320
gtggcgcaat ctcggctcac tgcaaactcc acctcctgag ttcaagtgat tctcctgcct   40380
cagcctccca agcagctggg attacaggtg cctgccacta cgtccagcta atttttttgtt  40440 attttttagta gagacagggt ttcatcatgt tggccaggct ggtctcgaac tcctgacctc   40500
gtgattcgcc cacttcggcc tcccaaagtg ctgggattac aggtgtgagc tactgtgccc   40560
agcccaagaa tggttttta  tactcaaaaa aaaaaaaaa  aaaaaaaaa  aaaaagcatg   40620 ggtgcaggat atgccaaatg ttaataatgg ctggtgatgg tttttttcct ttctctaata   40680
caaattttca gtcctgtgct tatgtaactt ttagaagaaa agaatttgct atgaatatat   40740
gtataaatca atacaaatag taagtgatca actatcactg gactcgtcag gaagattcaa   40800
attacctaaa aatataatgt aaagaaaga  ctgttagtat ctgaatggcc tgcagttgca   40860
aagaaatagt aaaactgtaa tcaaggcaat ctgaagcaaa ttctcatggt ttgcaaaaaa   40920
gggaaaggaa actttcctgc tgaagtggct ctaacaatgt atttactcta tatgaaagga   40980
gcatggacgt acgtgacccc atcataagta gaggagcatt tgtataggaa aagagtacat   41040
accctggagt gcttaactga aggctccacc tttcattaac agcataactt cagtttcctg   41100
gtctataaaa tggaaacaaa gagggtcttc tttcatagat atgaactagg ttccaatctg   41160
agcaaaattg tgtcaattct gcctgcccag gcagatgggg tttatggtaa tacaaaatca   41220
tttgagtctc agtggctgaa ctactgttag tctacatctg tgccattcaa agcagtgtct   41280 ttctttata  tatatattta cgattagacg atgaaaaaat actaacaccct ttggataatg   41340 tttagagttg aaaagaatct tggggtagag ccgatgttat caaaacctac agttatcttc   41400
tgagcactgg tcacctgtat ctgggaacaa atgggcttaa gagtttggaa attaagcagc   41460
aaataagtaa gaagttttgg tactctatac aactaccatt caaggttggt tatgagaact   41520
aaatgatgcc gtattagcca tggtcaaaga aaaaaaaga  gagaagagag aattaaacga   41580
gacaagacag atagaatatg tagcatattc ttgcaaccct tcaagaaatt tcaaagcaac   41640
ctgtgtgtat actttgcaag tcaattttt  ttaagttaga ttagaaattg ttctttgagg   41700
gagcagcttt ataaaagact tgatctgatc tataaaattg gaccataaaa ccaactgaac   41760
ttagtccact agtatttaag aaagtgatgt ctgagatgaa taattacaag tctaccaacc   41820
aattttcttc atgatgaaga agggtagcca taagaaactt acctggaaag caaacaaaac   41880
acataaaatt ggatctaatt cagagtggta aacaatttta atgtttatgg agactgcctg   41940
gatttgacat tgagaaaatt cagctaagaa tggcattaaa tgtaatccta agtattggag   42000
ttaggctggg tcaaaactga ccataaaattc tgaagagact ccaaaacttt tcctcaagct   42060
agttctatgg gacaaagcat taaaaaatcc ctgaaaata  tgccagcatc tgccctcaat   42120
tccaaaagca ggaagcaaag atgtgaccca atcacatgat atcaaaccac agtccatctg   42180
ttcagagaac tctgtgttac gtaagccatg accaaggaag aactgcaaaa ggcaagaggt   42240
gtgtcgacat ttgcaagggg ctctgtggtt tgaagagaca cgttctcaca tcagaagggc   42300
catccatagg ataatggcat tttcaaaatt ccatttatta cacatgaaca tatttggtgc   42360
aataaaatga cactacaaga atggtgttga gtccctgtaa ctgctcaact aaggcctaga   42420
```

```
accttttgac aggggtcttc cctacatgag cggccctcct cacaggaaca agatttatct   42480
tcctcttgat tatttttatg tcaattcctc tcttaatttc aacaacaaag cggatcatct   42540
aatattctaa accaaagcct tctaactaca ccccaattca attaactgta cttactcaag   42600
accatcttcc aaactactat aggcctactt ttctcaatca ataagtatat accaggtcct   42660
tttatcagca attaaaaaaa aattgacctt ttccttgaga actttaaggc tttaatcatt   42720 cccctccct tccaccttta gaattcactt ttcataaatt ctgtgaagtt caaggcctac   42780
ttcacttaag gaagtcactc atcccttcgt ggatgccaac cacctatccc aaccctgtcc   42840
cactcccacc tccaagtcct tcacatttta aagcaccata tagggcacaa gatatggaat   42900
cagaaaatca aagttcctgt ctctgttctg cccctgtgcc accctaagaa attcacctga   42960
gtcgtttttt catctgtaaa ttgaagtgat aatatactta ggacttccac catttgaatg   43020
cctagtccta ctgggcatcc cataatgtta ttctccctca ctcattccac tttgattact   43080
tttatgtttt gtttccagct atgtactata gcttttagga ttggggaaaa aatgatagag   43140
gttaatacat ccaaattcca cagtacagaa taaggaacct aactctgaag agtaacttgc   43200
cagtcagtca gtaaaagcct tgtttcctcc cttggagtag gccccaggac agttggggac   43260
acaacttcaa aagaactttc acactcatca aatccccctc tgaattctac ccaccttca   43320 aagtcagtgt aagtcctaaa gtgtccaaga agcctccccc aatcattcca gcttacacta   43380
atcatttccc tttttgaata ctaatgcctc cctatagaaa tgatattaaa aatatttaac   43440
aactggcact acaagggtac caaccaatca gaaaggatgt ttaaccaaaa cacacatggc   43500
ccagtgggaa ctgcttattg aacatcagtc ctgctcttta gcaacaacac agaatagcaa   43560
cctcaaactc aaataccact ttctcatgtg atcttcacaa tctcatgaat taggcaaaag   43620
taggtattgc cccattttct gcataactgc tggtgaaggt aggacaaata accaattgct   43680
ttcaacacgc catacaactt ttcctgatta tttatacgga attacaagtt aatattgcat   43740
aaactggact tacataaaac agtataaata ttaaaggaat gctcaaatag aaatcaacaa   43800
gcatttatgt ggaatagaat ataaaacaca gtgctaagtt ctgaggccac aaaagaaaga   43860
aatggcatga atcttgtcct ctgggtacct ataacgcatt caagtagagt taagtagcag   43920
cacaggcagt agaaatggac aacacaaact gttaagtgtt gcagagttct ggaagacaaa   43980
gaattcaaga actaaaccag cacaggaagt cagggctgag aacttctcgc actcccaaaa   44040
aaaggggcaa aactaaatgt gtagtgaaaa ggctgaacag tcaggagtca gtgagaaaga   44100
gaaattgctc gaaggtctgc agtaatgaga aatgagatcc ctggtaggat actcagagat   44160
ggccccaatc ataagctgct aagtgttgtt ctaagtgctg aatacaaatg ggaaatctta   44220
taaaccttca cggggaaggc tgaggaagat tagtttggca gtagccatag aaaagcctag   44280
atgagaaaaa catgggaaag caactagatt tggaggataa caggcaggat taagctgaag   44340
gctgcatacc aagaaaggag gagacattca agaggcattc atagaagagt tggattgggg   44400
gcacgttttc aaagaaaaaa agttatgaaa tggcagaaag gaagcaaata gcattctcag   44460
atgggatata catatagaca tagtggtact aaactgtgca ctaggataa ggaatcaatt   44520 tccctagaga aacctatgtt ggagacagaa gttgggcaga gaacattaaa acatactcag   44580
aacataaaaa ggtgcaagtc tttaaaaggg aagccaagtt acagaggaaa taaaaagcat   44640
ttgacctttt tcagaatgtt ttttaagggt ggactgaggc atcatcataa ccaacagggg   44700
aggcagacaa gctgaggcag tctgggctta gagtaataag cacctggaca gctttgtatt   44760
ttgtgcatac catggagact gtaaactcct ccaggacatg gactgagcaa tgttctgtgt   44820
```

```
cttcaactaa gtccactact gttacttgaa tacatgaacg cttcttgtgc tacttctggt   44880
ggaaaagagt gcactgtgtt attcaagtta atagcggtgt ggaaatgtta cctgtgtttc   44940
atgcctaact atactgattc tcccaaatgt ccacacagtt atcctgcctt cctccctagg   45000
ccaatgtcaa aaatccattg tttcctctaa tgcaggccca cgtgaaggga ctcaacaatg   45060
tgctaagagt cggaatgaag cctatctgat actcaaatca tgaggacaga atccaaagtg   45120
gataataaag accaattgct catcagacga ctgaagaaga aaaatgggct acgccagata   45180
gtatgatgta tacatattta tatatatata tgacatacag gtttgggaaa ctgagatctg   45240
agtgaaaatc ctagctttag cacttaagtt attgggtact taacgtgtct gtaccccact   45300
ttgcacatct gtaaagtggg gcaaatgcca ctactcctgg gagtttactt gtggtgatta   45360
aataatgtaa ttatacaata gtgtatgcat ttacatcgta gtaatgcaca atacatagac   45420
ggtagctatt aggactgatt ataatcgtca ccgtcagtct tgattttta aaaaaatttc    45480 aacatctttt gtccagtttc agaaacagaa atgtactttc actgcatttt agttgctaac   45540
actgaggctg tgtattttag cttctagtgt ctcagttcag ctgctaacga agttttcac    45600 tcatcccttt gtggataccca accacctacc ccaacctgat ttactatttt gaaaaatcca  45660
gccaacagtc ttccttgaaa accagctata cagatgtctg aatcaaacta ttaactgtca   45720
ctcaagaaaa ggaacaacgt gagtgatgtt ccttcgagga aataaaaagc gtttaatcaa   45780
ttcacagtcg ttcccaaaat ttccaaaacc cgcagaatga gcaaacgttc aagtttccac   45840
tatgaaaaca atccgtagcc gtctggttac tggactcact tcaacactcc ccagacgcac   45900
gaaagaagaa acattccgcg catctccgcg cttccttctt ctcacacaaa gcccccctgg   45960
ctggaggagc agcccccttcc agcagggtcg gctcgggtcg agccgggcgg gagtcagggc  46020
ggcctgcgga cccaggggtc tcaccacacg tcgccccga ctcccactgg acgaagccct    46080
agaggctcgg agctcacacc ccgcccggga gccgccttcc accccaacct caaaccccgc   46140
cccgggttcg gcagcctctg gcacggaccc tcttggggcg ggggtcccca gaacaaggtc   46200
acgccgtgcc caggggggcgg cggcgggcag ccacggctct gccagtcccc gccggcctcg   46260
cactctccgc ccctggccct cgcccactca caccccagag ggcagccccg gacctcggac   46320
gactccgccc gactccacct ccccggggag tcccgagcgg ggcggcctcg ggcagccgga   46380
cacgtccgcc cgcgcccgga cacacgcccc tgccccgcct ccgctcccccg cttgcggttc   46440 gcccggcagc cgccgagccg cgcggcgcca cgagagcccg gcccgggccc cggcgccgcc   46500
acctgcgccc ccggccccgc gccatgtttg agaaagagca ggagcgagcc agaggccggg   46560
tccggcccgc gcgccccgca gtcgcccgcc cgccgcgccg ccgctcaccc gtcgccccg    46620 ggagcagcgc cgccgccgcc gccgccgccg ccgccagcac gaggaggagc agccggggac   46680
gcggagcagc gaccgccgcc tccatggtcc cgccgccacc gcctgtggcc cggcccggcc   46740
cggccgcgcc gctgcctcac cccagcaaac ctcgcctcgc cccacctccc tagccgccgc   46800
ggcggcctcg ctccggccct ttgtaactgc tcggaggacg cgcgtccatt ggctgccggg   46860
ctcccgccgg ccccgcctcc ccgccgccgc gagctgccaa gcgggaccca gccgggagcc   46920
ccgcctgcgg gcccgccagg cagccaatcc gcagccgcga gcgccggttt ctggccacgc   46980
cccacgctcc ccgggggctg ggccgccaga ccccagcccc ggcccgatcg gctcccggct   47040
ccgagaggcc gcgtgggggc ggggtctgcc agcccagca ccgctcagcc gctagccccg    47100
gagggccggg tagagcgatg ggtgtgtctg tgtgagtctc tttcggaaaa aggctgtggc   47160
cgttcgacgc tctttcttc taacctcctc taggcgcgga agatctggta ctgcctcagc    47220
```

```
cccaccctga ccccattcac agctccgcat tggcaatccc agcacatgcc acccagatcc    47280
gctgcagcgc caggccctg catccacttc aacttcccct ctccaagtcc acgcatcaac     47340
ttcagcattc ccccgaagat ccctcctcag tgcccttcac atgcgactca ctctcctatt    47400
tcctcctgct cccagcggtc accccaaacc cagctcccc acccagttcc aaacccagaa     47460
agtcctcaga tcccagcgtc agacccagat cctgagccca acacacccc caaatagcct     47520 cccgcctccc tccagcacag atccaggatg gggatccaag ccgcactcct ctcaaacccc    47580
ttcccgatcc aggttggaaa gggaggatcc ccaccccaac ccctcaaagg aggggttccc    47640
ccttcttagc acccagctcc cgcggggcgg aggggagca gtcatcatta ctttgagctg     47700
tgtctgacac tgctgtataa taatcctgag gtgtcactaa aaaccaaat aaactctacg     47760 ttttcattct gaattcctaa tttactgcga gacgctccac ccaccttccc tctgcgacgc    47820
caaaatgagc tccagatttg taattcttcc tgtcagacta gtcctttctt cagacacaaa    47880
cacagccaag gaggctgtta cgtagaacag agaatatttt tccgcagaac cttttaagga    47940
ggaaatttta ttttctgtgt catttgagct tagaattaaa taaaccttga tagcaggaat    48000
cagaatggtt ctgattaatg ccaatttgtg cactacttta gagtcactgg gtgagcattt    48060
tccccacctg tgaaggcttc cttccgggag atgaaaaggg aaaaggcgtg gatattggag    48120
ctgggatctg agaccgcgc gctttctccc tcctgtctag gacacttact taagcaagtc     48180
agctaacctt tctgaacctc caacaggctc agaggcctgc aacttgctct acaccgcagc    48240
tccagcagcc tcagcagcaa actcccctct tgctcaggct gagggattcc agagagatgg   48300
cttctggcag gctccagtcc caatttgccc tctcagttcc agtttcttca atggagattt    48360
ggtggacttt gtgccacctg aggtccctag actgccttt tgctgctcta tttgcaatgt     48420 cttttcataag ataagagcta atgagatttt tattgtatga atgaatgaat gatctcagaa   48480
agtgactgtt tttctctggc cattagcttc ttcatctcta aaatgtaaat aataatagta    48540
cctaccccgt ttataaataa aagggattga atcacttgtc ttgggcccct taaatgacgt    48600
aatgtgtctg gtacagtgtc tggaacatag taaatattta gctaatgcca tttcttcgcc    48660 catcccttc cagctctgta tgattctaat cagcatgtat gttcatgtca gtctgtgcct     48720
ttgacgtacg gagcctagat taatcagtgt taatcacacc tccagttcct taaca          48775
```

<210> SEQ ID NO 97
<211> LENGTH: 21
<212> TYPE: DNA
<213> ORGANISM: Artificial sequence
<220> FEATURE:
<223> OTHER INFORMATION: antisense oligonucleotide

<400> SEQUENCE: 97
gatcttgact gccactgtct c                                              21

<210> SEQ ID NO 98
<211> LENGTH: 16
<212> TYPE: DNA
<213> ORGANISM: Artificial sequence
<220> FEATURE:
<223> OTHER INFORMATION: antisense oligonucleotide

<400> SEQUENCE: 98
catggcagcc cccgtc                                                    16

<210> SEQ ID NO 99
<211> LENGTH: 16

```
<212> TYPE: DNA
<213> ORGANISM: Artificial sequence
<220> FEATURE:
<223> OTHER INFORMATION: sense oligonucleotide

<400> SEQUENCE: 99
catgggtcgg gggctg                                                    16

<210> SEQ ID NO 100
<211> LENGTH: 16
<212> TYPE: DNA
<213> ORGANISM: Artificial sequence
<220> FEATURE:
<223> OTHER INFORMATION: missense oligonucleotide

<400> SEQUENCE: 100
catccccgga cccgtg                                                    16

<210> SEQ ID NO 101
<211> LENGTH: 16
<212> TYPE: DNA
<213> ORGANISM: Artificial sequence
<220> FEATURE:
<223> OTHER INFORMATION: general sequence
<220> FEATURE:
<221> NAME/KEY: X
<222> LOCATION: (1)..(1)
<223> OTHER INFORMATION: oligonucleotides representing group X
<220> FEATURE:
<221> NAME/KEY: Z
<222> LOCATION: (16)..(16)
<223> OTHER INFORMATION: oligonucleotides representing group Z

<400> SEQUENCE: 101 cagccccga cccatg                                                     16

<210> SEQ ID NO 102
<211> LENGTH: 34
<212> TYPE: DNA
<213> ORGANISM: Artificial sequence
<220> FEATURE:
<223> OTHER INFORMATION: oligonucleotides representing group X

<400> SEQUENCE: 102
acaggacgat gtgcagcggc cacaggcccc tgag                                34

<210> SEQ ID NO 103
<211> LENGTH: 33
<212> TYPE: DNA
<213> ORGANISM: Artificial sequence
<220> FEATURE:
<223> OTHER INFORMATION: oligonucleotides representing group X

<400> SEQUENCE: 103
caggacgatg tgcagcggcc acaggcccct gag                                 33

<210> SEQ ID NO 104
<211> LENGTH: 32
<212> TYPE: DNA
<213> ORGANISM: Artificial sequence
<220> FEATURE:
<223> OTHER INFORMATION: oligonucleotides representing group X

<400> SEQUENCE: 104
aggacgatgt gcagcggcca caggcccctg ag                                  32

<210> SEQ ID NO 105
<211> LENGTH: 31
```

```
<212> TYPE: DNA
<213> ORGANISM: Artificial sequence
<220> FEATURE:
<223> OTHER INFORMATION: oligonucleotides representing group X

<400> SEQUENCE: 105
ggacgatgtg cagcggccac aggcccctga g                              31

<210> SEQ ID NO 106
<211> LENGTH: 30
<212> TYPE: DNA
<213> ORGANISM: Artificial sequence
<220> FEATURE:
<223> OTHER INFORMATION: oligonucleotides representing group X

<400> SEQUENCE: 106
gacgatgtgc agcggccaca ggcccctgag                                30

<210> SEQ ID NO 107
<211> LENGTH: 29
<212> TYPE: DNA
<213> ORGANISM: Artificial sequence
<220> FEATURE:
<223> OTHER INFORMATION: oligonucleotides representing group X

<400> SEQUENCE: 107
acgatgtgca gcggccacag gcccctgag                                 29

<210> SEQ ID NO 108
<211> LENGTH: 28
<212> TYPE: DNA
<213> ORGANISM: Artificial sequence
<220> FEATURE:
<223> OTHER INFORMATION: oligonucleotides representing group X

<400> SEQUENCE: 108
cgatgtgcag cggccacagg ccctgag                                   28

<210> SEQ ID NO 109
<211> LENGTH: 27
<212> TYPE: DNA
<213> ORGANISM: Artificial sequence
<220> FEATURE:
<223> OTHER INFORMATION: oligonucleotides representing group X

<400> SEQUENCE: 109
gatgtgcagc ggccacaggc ccctgag                                   27

<210> SEQ ID NO 110
<211> LENGTH: 26
<212> TYPE: DNA
<213> ORGANISM: Artificial sequence
<220> FEATURE:
<223> OTHER INFORMATION: oligonucleotides representing group X

<400> SEQUENCE: 110
atgtgcagcg gccacaggcc cctgag                                    26

<210> SEQ ID NO 111
<211> LENGTH: 25
<212> TYPE: DNA
<213> ORGANISM: Artificial sequence
<220> FEATURE:
<223> OTHER INFORMATION: oligonucleotides representing group X

<400> SEQUENCE: 111
tgtgcagcgg ccacaggccc ctgag                                     25
```

<210> SEQ ID NO 112
<211> LENGTH: 24
<212> TYPE: DNA
<213> ORGANISM: Artificial sequence
<220> FEATURE:
<223> OTHER INFORMATION: oligonucleotides representing group X

<400> SEQUENCE: 112
gtgcagcggc cacaggcccc tgag                                          24

<210> SEQ ID NO 113
<211> LENGTH: 23
<212> TYPE: DNA
<213> ORGANISM: Artificial sequence
<220> FEATURE:
<223> OTHER INFORMATION: oligonucleotides representing group X

<400> SEQUENCE: 113
tgcagcggcc acaggcccct gag                                           23

<210> SEQ ID NO 114
<211> LENGTH: 22
<212> TYPE: DNA
<213> ORGANISM: Artificial sequence
<220> FEATURE:
<223> OTHER INFORMATION: oligonucleotides representing group X

<400> SEQUENCE: 114
gcagcggcca caggcccctg ag                                            22

<210> SEQ ID NO 115
<211> LENGTH: 21
<212> TYPE: DNA
<213> ORGANISM: Artificial sequence
<220> FEATURE:
<223> OTHER INFORMATION: oligonucleotides representing group X

<400> SEQUENCE: 115
cagcggccac aggcccctga g                                             21

<210> SEQ ID NO 116
<211> LENGTH: 20
<212> TYPE: DNA
<213> ORGANISM: Artificial sequence
<220> FEATURE:
<223> OTHER INFORMATION: oligonucleotides representing group X

<400> SEQUENCE: 116
agcggccaca ggcccctgag                                               20

<210> SEQ ID NO 117
<211> LENGTH: 19
<212> TYPE: DNA
<213> ORGANISM: Artificial sequence
<220> FEATURE:
<223> OTHER INFORMATION: oligonucleotides representing group X

<400> SEQUENCE: 117
gcggccacag gcccctgag                                                19

<210> SEQ ID NO 118
<211> LENGTH: 18
<212> TYPE: DNA
<213> ORGANISM: Artificial sequence
<220> FEATURE:
<223> OTHER INFORMATION: oligonucleotides representing group X

```
<400> SEQUENCE: 118
cggccacagg cccctgag                                              18

<210> SEQ ID NO 119
<211> LENGTH: 17
<212> TYPE: DNA
<213> ORGANISM: Artificial sequence
<220> FEATURE:
<223> OTHER INFORMATION: oligonucleotides representing group X

<400> SEQUENCE: 119
ggccacaggc ccctgag                                               17

<210> SEQ ID NO 120
<211> LENGTH: 16
<212> TYPE: DNA
<213> ORGANISM: Artificial sequence
<220> FEATURE:
<223> OTHER INFORMATION: oligonucleotides representing group X

<400> SEQUENCE: 120
gccacaggcc cctgag                                                16

<210> SEQ ID NO 121
<211> LENGTH: 15
<212> TYPE: DNA
<213> ORGANISM: Artificial sequence
<220> FEATURE:
<223> OTHER INFORMATION: oligonucleotides representing group X

<400> SEQUENCE: 121
ccacaggccc ctgag                                                 15

<210> SEQ ID NO 122
<211> LENGTH: 14
<212> TYPE: DNA
<213> ORGANISM: Artificial sequence
<220> FEATURE:
<223> OTHER INFORMATION: oligonucleotides representing group X

<400> SEQUENCE: 122
cacaggcccc tgag                                                  14

<210> SEQ ID NO 123
<211> LENGTH: 13
<212> TYPE: DNA
<213> ORGANISM: Artificial sequence
<220> FEATURE:
<223> OTHER INFORMATION: oligonucleotides representing group X

<400> SEQUENCE: 123
acaggcccct gag                                                   13

<210> SEQ ID NO 124
<211> LENGTH: 12
<212> TYPE: DNA
<213> ORGANISM: Artificial sequence
<220> FEATURE:
<223> OTHER INFORMATION: oligonucleotides representing group X

<400> SEQUENCE: 124
caggcccctg ag                                                    12

<210> SEQ ID NO 125
<211> LENGTH: 11
```

```
<212> TYPE: DNA
<213> ORGANISM: Artificial sequence
<220> FEATURE:
<223> OTHER INFORMATION: oligonucleotides representing group X

<400> SEQUENCE: 125
aggcccctga g                                                            11

<210> SEQ ID NO 126
<211> LENGTH: 10
<212> TYPE: DNA
<213> ORGANISM: Artificial sequence
<220> FEATURE:
<223> OTHER INFORMATION: oligonucleotides representing group X

<400> SEQUENCE: 126
ggcccctgag                                                              10

<210> SEQ ID NO 127
<211> LENGTH: 9
<212> TYPE: DNA
<213> ORGANISM: Artificial sequence
<220> FEATURE:
<223> OTHER INFORMATION: oligonucleotides representing group X

<400> SEQUENCE: 127 gcccctgag                                                                9

<210> SEQ ID NO 128
<211> LENGTH: 8
<212> TYPE: DNA
<213> ORGANISM: Artificial sequence
<220> FEATURE:
<223> OTHER INFORMATION: oligonucleotides representing group X

<400> SEQUENCE: 128 cccctgag                                                                 8

<210> SEQ ID NO 129
<211> LENGTH: 7
<212> TYPE: DNA
<213> ORGANISM: Artificial sequence
<220> FEATURE:
<223> OTHER INFORMATION: oligonucleotides representing group X

<400> SEQUENCE: 129 ccctgag                                                                  7

<210> SEQ ID NO 130
<211> LENGTH: 6
<212> TYPE: DNA
<213> ORGANISM: Artificial sequence
<220> FEATURE:
<223> OTHER INFORMATION: oligonucleotides representing group X

<400> SEQUENCE: 130 cctgag                                                                   6

<210> SEQ ID NO 131
<211> LENGTH: 5
<212> TYPE: DNA
<213> ORGANISM: Artificial sequence
<220> FEATURE:
<223> OTHER INFORMATION: oligonucleotides representing group X

<400> SEQUENCE: 131 ctgag                                                                    5
```

```
<210> SEQ ID NO 132
<211> LENGTH: 4
<212> TYPE: DNA
<213> ORGANISM: Artificial sequence
<220> FEATURE:
<223> OTHER INFORMATION: oligonucleotides representing group X

<400> SEQUENCE: 132 tgag                                                                  4

<210> SEQ ID NO 133
<211> LENGTH: 34
<212> TYPE: DNA
<213> ORGANISM: Artificial sequence
<220> FEATURE:
<223> OTHER INFORMATION: oligonucleotides representing group Z

<400> SEQUENCE: 133
gcagaccccg ctgctcgtca tagaccgagc cccc                                34

<210> SEQ ID NO 134
<211> LENGTH: 33
<212> TYPE: DNA
<213> ORGANISM: Artificial sequence
<220> FEATURE:
<223> OTHER INFORMATION: oligonucleotides representing group Z

<400> SEQUENCE: 134
gcagaccccg ctgctcgtca tagaccgagc ccc                                 33

<210> SEQ ID NO 135
<211> LENGTH: 32
<212> TYPE: DNA
<213> ORGANISM: Artificial sequence
<220> FEATURE:
<223> OTHER INFORMATION: oligonucleotides representing group Z

<400> SEQUENCE: 135
gcagaccccg ctgctcgtca tagaccgagc cc                                  32

<210> SEQ ID NO 136
<211> LENGTH: 31
<212> TYPE: DNA
<213> ORGANISM: Artificial sequence
<220> FEATURE:
<223> OTHER INFORMATION: oligonucleotides representing group Z

<400> SEQUENCE: 136
gcagaccccg ctgctcgtca tagaccgagc c                                   31

<210> SEQ ID NO 137
<211> LENGTH: 30
<212> TYPE: DNA
<213> ORGANISM: Artificial sequence
<220> FEATURE:
<223> OTHER INFORMATION: oligonucleotides representing group Z

<400> SEQUENCE: 137
gcagaccccg ctgctcgtca tagaccgagc                                     30

<210> SEQ ID NO 138
<211> LENGTH: 29
<212> TYPE: DNA
<213> ORGANISM: Artificial sequence
<220> FEATURE:
<223> OTHER INFORMATION: oligonucleotides representing group Z
```

```
<400> SEQUENCE: 138
gcagaccccg ctgctcgtca tagaccgag                                29

<210> SEQ ID NO 139
<211> LENGTH: 28
<212> TYPE: DNA
<213> ORGANISM: Artificial sequence
<220> FEATURE:
<223> OTHER INFORMATION: oligonucleotides representing group Z

<400> SEQUENCE: 139
gcagaccccg ctgctcgtca tagaccga                                 28

<210> SEQ ID NO 140
<211> LENGTH: 27
<212> TYPE: DNA
<213> ORGANISM: Artificial sequence
<220> FEATURE:
<223> OTHER INFORMATION: oligonucleotides representing group Z

<400> SEQUENCE: 140
gcagaccccg ctgctcgtca tagaccg                                  27

<210> SEQ ID NO 141
<211> LENGTH: 26
<212> TYPE: DNA
<213> ORGANISM: Artificial sequence
<220> FEATURE:
<223> OTHER INFORMATION: oligonucleotides representing group Z

<400> SEQUENCE: 141
gcagaccccg ctgctcgtca tagacc                                   26

<210> SEQ ID NO 142
<211> LENGTH: 25
<212> TYPE: DNA
<213> ORGANISM: Artificial sequence
<220> FEATURE:
<223> OTHER INFORMATION: oligonucleotides representing group Z

<400> SEQUENCE: 142
gcagaccccg ctgctcgtca tagac                                    25

<210> SEQ ID NO 143
<211> LENGTH: 24
<212> TYPE: DNA
<213> ORGANISM: Artificial sequence
<220> FEATURE:
<223> OTHER INFORMATION: oligonucleotides representing group Z

<400> SEQUENCE: 143
gcagaccccg ctgctcgtca taga                                     24

<210> SEQ ID NO 144
<211> LENGTH: 23
<212> TYPE: DNA
<213> ORGANISM: Artificial sequence
<220> FEATURE:
<223> OTHER INFORMATION: oligonucleotides representing group Z

<400> SEQUENCE: 144
gcagaccccg ctgctcgtca tag                                      23

<210> SEQ ID NO 145
<211> LENGTH: 22
```

```
<212> TYPE: DNA
<213> ORGANISM: Artificial sequence
<220> FEATURE:
<223> OTHER INFORMATION: oligonucleotides representing group Z

<400> SEQUENCE: 145
gcagaccccg ctgctcgtca ta                                              22

<210> SEQ ID NO 146
<211> LENGTH: 21
<212> TYPE: DNA
<213> ORGANISM: Artificial sequence
<220> FEATURE:
<223> OTHER INFORMATION: oligonucleotides representing group Z

<400> SEQUENCE: 146
gcagaccccg ctgctcgtca t                                               21

<210> SEQ ID NO 147
<211> LENGTH: 20
<212> TYPE: DNA
<213> ORGANISM: Artificial sequence
<220> FEATURE:
<223> OTHER INFORMATION: oligonucleotides representing group Z

<400> SEQUENCE: 147
gcagaccccg ctgctcgtca                                                 20

<210> SEQ ID NO 148
<211> LENGTH: 19
<212> TYPE: DNA
<213> ORGANISM: Artificial sequence
<220> FEATURE:
<223> OTHER INFORMATION: oligonucleotides representing group Z

<400> SEQUENCE: 148
gcagaccccg ctgctcgtc                                                  19

<210> SEQ ID NO 149
<211> LENGTH: 18
<212> TYPE: DNA
<213> ORGANISM: Artificial sequence
<220> FEATURE:
<223> OTHER INFORMATION: oligonucleotides representing group Z

<400> SEQUENCE: 149
gcagaccccg ctgctcgt                                                   18

<210> SEQ ID NO 150
<211> LENGTH: 17
<212> TYPE: DNA
<213> ORGANISM: Artificial sequence
<220> FEATURE:
<223> OTHER INFORMATION: oligonucleotides representing group Z

<400> SEQUENCE: 150
gcagaccccg ctgctcg                                                    17

<210> SEQ ID NO 151
<211> LENGTH: 16
<212> TYPE: DNA
<213> ORGANISM: Artificial sequence
<220> FEATURE:
<223> OTHER INFORMATION: oligonucleotides representing group Z

<400> SEQUENCE: 151
gcagaccccg ctgctc                                                     16
```

```
<210> SEQ ID NO 152
<211> LENGTH: 15
<212> TYPE: DNA
<213> ORGANISM: Artificial sequence
<220> FEATURE:
<223> OTHER INFORMATION: oligonucleotides representing group Z

<400> SEQUENCE: 152
gcagaccccg ctgct                                                      15

<210> SEQ ID NO 153
<211> LENGTH: 14
<212> TYPE: DNA
<213> ORGANISM: Artificial sequence
<220> FEATURE:
<223> OTHER INFORMATION: oligonucleotides representing group Z

<400> SEQUENCE: 153
gcagaccccg ctgc                                                       14

<210> SEQ ID NO 154
<211> LENGTH: 13
<212> TYPE: DNA
<213> ORGANISM: Artificial sequence
<220> FEATURE:
<223> OTHER INFORMATION: oligonucleotides representing group Z

<400> SEQUENCE: 154
gcagaccccg ctg                                                        13

<210> SEQ ID NO 155
<211> LENGTH: 12
<212> TYPE: DNA
<213> ORGANISM: Artificial sequence
<220> FEATURE:
<223> OTHER INFORMATION: oligonucleotides representing group Z

<400> SEQUENCE: 155
gcagaccccg ct                                                         12

<210> SEQ ID NO 156
<211> LENGTH: 11
<212> TYPE: DNA
<213> ORGANISM: Artificial sequence
<220> FEATURE:
<223> OTHER INFORMATION: oligonucleotides representing group Z

<400> SEQUENCE: 156
gcagaccccg c                                                          11

<210> SEQ ID NO 157
<211> LENGTH: 10
<212> TYPE: DNA
<213> ORGANISM: Artificial sequence
<220> FEATURE:
<223> OTHER INFORMATION: oligonucleotides representing group Z

<400> SEQUENCE: 157
gcagaccccg                                                            10

<210> SEQ ID NO 158
<211> LENGTH: 9
<212> TYPE: DNA
<213> ORGANISM: Artificial sequence
<220> FEATURE:
<223> OTHER INFORMATION: oligonucleotides representing group Z
```

```
<400> SEQUENCE: 158 gcagacccc                                                                9

<210> SEQ ID NO 159
<211> LENGTH: 8
<212> TYPE: DNA
<213> ORGANISM: Artificial sequence
<220> FEATURE:
<223> OTHER INFORMATION: oligonucleotides representing group Z

<400> SEQUENCE: 159 gcagaccc                                                                 8

<210> SEQ ID NO 160
<211> LENGTH: 7
<212> TYPE: DNA
<213> ORGANISM: Artificial sequence
<220> FEATURE:
<223> OTHER INFORMATION: oligonucleotides representing group Z

<400> SEQUENCE: 160 gcagacc                                                                  7

<210> SEQ ID NO 161
<211> LENGTH: 6
<212> TYPE: DNA
<213> ORGANISM: Artificial sequence
<220> FEATURE:
<223> OTHER INFORMATION: oligonucleotides representing group Z

<400> SEQUENCE: 161 gcagac                                                                   6

<210> SEQ ID NO 162
<211> LENGTH: 5
<212> TYPE: DNA
<213> ORGANISM: Artificial sequence
<220> FEATURE:
<223> OTHER INFORMATION: oligonucleotides representing group Z

<400> SEQUENCE: 162 gcaga                                                                    5

<210> SEQ ID NO 163
<211> LENGTH: 4
<212> TYPE: DNA
<213> ORGANISM: Artificial sequence
<220> FEATURE:
<223> OTHER INFORMATION: oligonucleotides representing group Z

<400> SEQUENCE: 163 gcag                                                                     4
```

INHIBITORS OF TGF-R-SIGNALING FOR TREATMENT OF CNS DISORDERS

The present invention relates to the use of oligonucleotides for the preparation of a pharmaceutical composition for the prevention or treatment of a disease, wherein neurogenesis and/or neuroregeneration has a beneficial effect, in particular a neurodegenerative disease like Morbus Alzheimer, Morbus Parkinson incl. Multisystem-Atrophy, Progressive Supranuclear Palsy, Corticobasal Degeneration, Lewy Body Dementia, Amyotrophic Lateral Sclerosis and other Motor Neuron Disorders, Huntington's disease, Spinocerebellar Atrophies, Creutzfeldt Jakob and other severe Prion Diseases, Frontemporal Dementia incl. Morbus Pick, AIDS Dementia Complex, Hallervorden Spatz Disease, Huntington's disease, a cerebrovascular disease like Vascular Dementia, Stroke, Traumatic Brain and spinal cord Injury, Retinitis Pigmentosa, Macular Degeneration, Glaucoma, Depression and Schizophrenia, and developmental disorders like Down's syndrome.

A number of severe neurodegenerative disorders have severe socioeconomic impact upon modern societies, e.g., disorders like Morbus Alzheimer, Developmental disorders with dementia (like Down's syndrome), Morbus Parkinson, Lewy Body Dementia, Frontemporal Dementia, Morbus Pick, Amyotrophic Lateral Sclerosis, Spinocerebellar Atrophies; Creutzfeldt Jakob Disease, AIDS Dementia Complex, Vascular Dementia, Progressive Supranuclear Palsy, Corticobasal Degeneration, Multisystem-Atrophy, Huntington's disease, Stroke, Traumatic Brain Injury, Retinitis Pigmentosa, Macular Degeneration, Glaucoma, Depression, Schizophrenia, and Multiple Sclerosis. The common pathophysiological cause is found in genetic, epigenetic or acquired defects—frequently resulting in aggregate formation or accumulation of cell debris—ultimately leading to progressive dysfunction and finally to neuronal or glial cell death and structural disintegration. Microglia cells and perivascular resting macrophages are attracted and activated, trying to clear the cell and tissue debris. This may happen in a very short span of time, as in Creutzfeldt Jacob Disease, or over decades, as e.g. in Parkinson's Disease or Multiple Sclerosis. The activated microglial/macrophage cell population releases a number of inflammatory cytokines into the extracellular matrix, draining these either into small venules or the CSF-space. Unfortunately, neurogenesis and neuroregeneration that could have an advantageous effect on the clinical course of these diseases described above (despite their individual specific pathophysiological mechanisms) is suppressed by so far unknown mechanisms. Thus, the technical problem underlying the present invention is to provide means suitable for treating or preventing neurodegenerative disorders or at least symptoms associated with said disorders by interfering with the suppression of neurogenesis and neuroregeneration.

The solution of the said technical problem is achieved by providing the embodiments characterized in the claims. The TGF-beta family of proteins, namely TGF-beta1, TGF-beta2 and TGF-beta3 with their specific cell surface receptors TGF RI, TGF RII, TGF RIII are known to act on several crucial aspects of embryonal and mainly mesenchymal/neuroektodermal organ development. They allow embryonal stem cells to differentiate into neuronal precursor cells, and are neuroprotective for injured mature neurons. It is further known that they have a critical impact upon hematopoetic stem cell differentiation, controlling proliferation and also differentiation. During the experiments leading to the present invention it was found that TGF-R, i.e. TGF RI and TGF RII are crucial factors involved in suppression of neurogenesis and neuroregeneration and, accordingly, a compound which is capable of interfering with this biological activity of TGF R or TGF RII is useful for the treatment/prevention of neurodegenerative disorders and/or neuroinflammatory disorders.

To summarize, as a result of the experiments leading to the present invention:

1. A physiological regulatory circuit has been recognized that accounts for the level of effective CNS-reneration by precursor-/stem cells, although of course the individual components have been known (TGF-$\beta$, TGF-RII, cerebrospinal fluid compartment, vitreous, endolymphatic fluid, neuronal precursor cells, etc). This circuit—with the crucial target molecule TGF-RII expressed at the ventricular wall—is responsible for the defunct neuroregeneration in the majority of CNS-pathology.

2. Interestingly the regulation takes places not via blood, lymphatics, or extracellular matrix but via fluid compartments (cerebrospinal fluid etc.), which have direct contact to neuronal cells and their precursors or stem cells.

3. A physiologically inhibitory circuit for neuronal/oligo-dendroglial or astrocytic renewal has been discovered as being an ideal target for strategies to repair damage within the CNS, overwhelmingly being applicable for almost all destructive pathology in the nervous system. From previous knowledge on TGF-$\beta$ it has been tried rather to increase than decrease (see 5) TGF-$\beta$ function in order to augment its known neuroprotective or immunosuppresive activities in the CNS: here we postulate to decrease its inhibitory function on stem cell renewal by blocking TGF-RII signalling at the ventricular wall.

4. Although for a long time it has been speculated that inflammatory processes play a significant role in neurodegeneration, and a relative large amount of preclinical and clinical data seem to support this idea, the master circuit is now being disclosed, that orchestrates all the single regulatory sub-circles, e.g. cytokines (IL-1, IL-6, IL-12) and others.

5. In addition, it might be noted that Nature has installed neuroprotection and an immunoprivileged CNS above neuroregeneration in priority: it has not been shown so far that the immunopriviliged and highly protected CNS (protected specifically against immune attacks and neuronal apoptosis), which is in significant part due to the TGF-$\beta$ system, has deficits in neuroregeneration due to exactly this privilege and due to the same molecule TGF-$\beta$. The evolutionary concept seems to argue in favour for acute neuroprotection of a highly sophisticated CNS and its most complex functioning; in this context, individual neuroregeneration seems less important for evolution than neuroprotection of the individuum.

The Regulatory Circuit

Physiologically neurogenesis of the brain allows continuous repair/replacement of malfunctioning or ageing neuronal, oligodendroglial or astrocytic cells by respective precursor cells. Neurogenesis for repair in the brain is regulated by the TGF-$\beta$-TGF-R (especially TGF RII, but also TGF RI) system, via the cerebrospinal fluid; the main orchestrators are micoglial/macrophage lineage cells producing TGF-$\beta$ and secreting it via extracellular space into the CSF (as well as within vitreous, endolymphatics) compartment, and neuronal precursor cells/stem cells, that receive this signal via CSF (as well as into vitreous, endolymphatics) through highly expressed TGF-RII or TGF-RI on their surface structures, or an ependymal lining with identical receptors. In the majority of CNS-pathology neurogenesis is severely impaired or malfunctioning. The regulation of neurogenesis is adjusted, usually suppressed (!) by the activation of microglial cells/macrophages from within the CNS, taking place in the context of any specific disease pathology. Activated microglial cells/macrophages by this route—CSF to subventruclar zone/other neurogenic zones—suppress the regeneration of the neurodegenerating, acute and chronic inflammatory, hypoxic, atherosclerotic or ageing brain parenchyma. Not only neuronal differentiation is affected, but also oligodendroglial and astrocytic cell lineages. All molecules that interfere with this circuit to improve neuronal/oligodenroglial/astrocytic regeneration are claimed as treatment. Methods for diagnostics, prophylaxis, prevention or prognosis of CNS pathology employing this circuit are also of high importance, conceivably for monitoring the effects of therapeutic intervention.

Adult rodent neural stem and precursor cell cultures were treated with 10 ng/ml of recombinant human TGF-beta1 for 7 days. On day 7 cells were dissociated, counted by Trypan Blue exclusion assay and TGF-beta1 pre-treated cells were reseeded in with or without 10 ng/ml TGF-beta1. This procedure was performed every 7 days. The data are expressed as average cell numbers ±SD from three experiments performed in triplicate.

Figure 3:
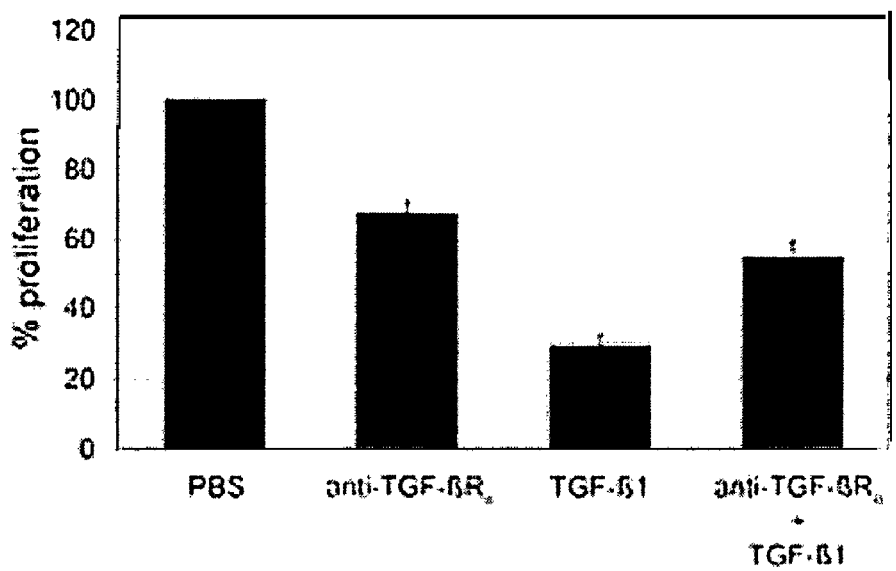

FIG. 3: Antibodies against TGF-betaRII can reduce TGF-beta1 effects on adult rodent NSCs Adult rodent NSC cultures were treated with 10 ng/ml of recombinant human TGF-beta1 for 7 days in the presence or absence of anti-TGF-betaRII antibody (10 µg/ml). On day 7 viable cells were counted by Trypan Blue exclusion assay in a hemocytometer. The data are expressed as average cell numbers ±SD from three experiments performed in triplicate.

Figure 4:
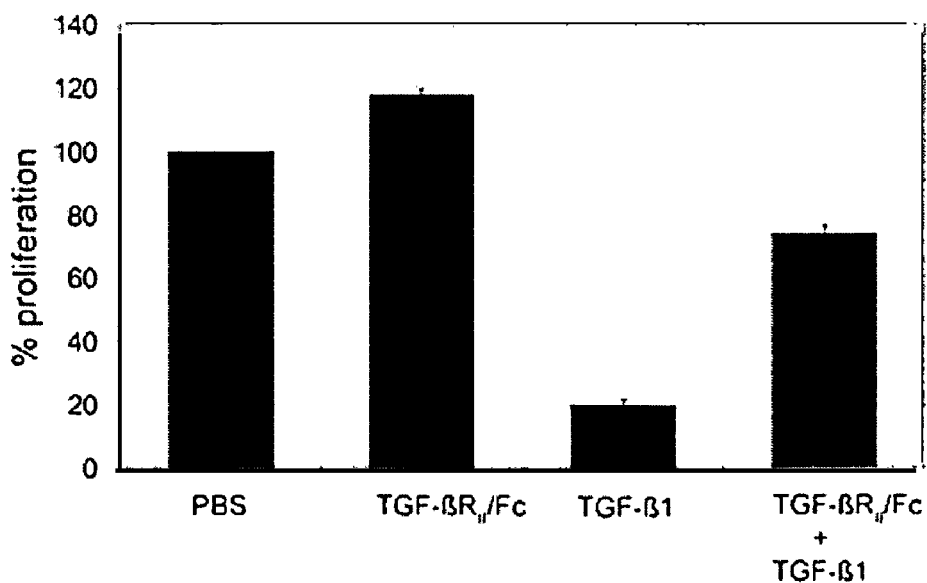

FIG. 4: Soluble TGF-RII inhibits TGF-$\beta$1-induced suppression of NSC proliferation Adult rodent NSC cultures were treated with 10 ng/ml of recombinant human TGF-beta1 for 7 days in the presence or absence of soluble anti-TGF-betaRII (500 ng/ml). On day 7 viable cells were counted by Trypan Blue exclusion assay in a hemocytometer. The data are expressed as average ±SD from three experiments performed in triplicate.

FIG. 5:

TGF-$\beta R_{II}$-expressing cells can be isolated using cell sorting techniques.

Adult rodent NSCs were prepared as described in example 1. Cells expressing TGF-bRII were purified using antibodies against TGF-bRII. About 20% of NSCs express the receptor and this cell population can be enriched by this approach.

Figure 6:
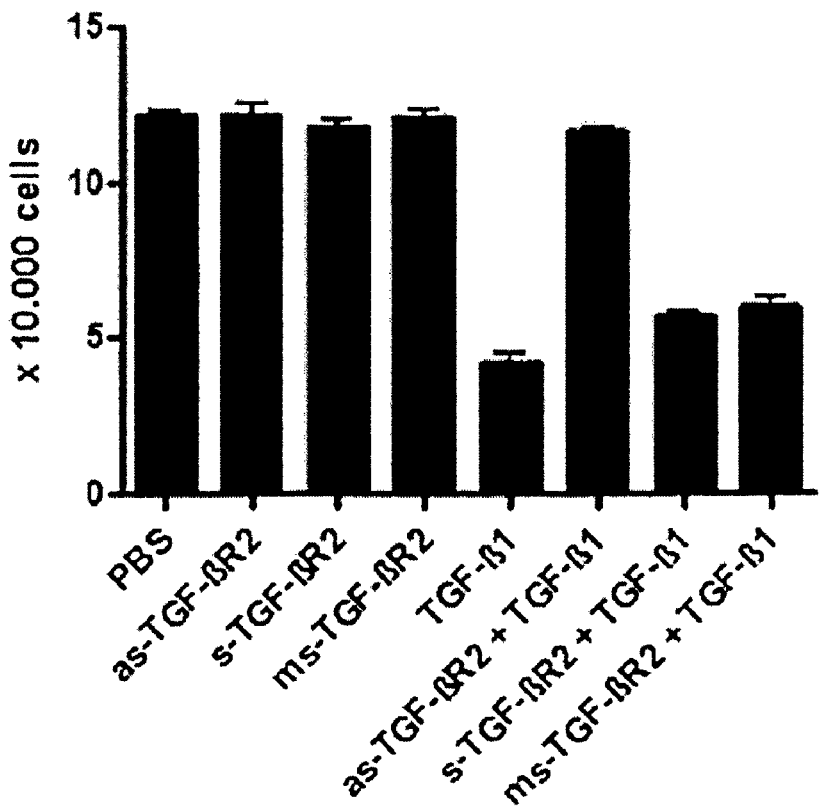

FIG. 6: Antisense oligonucleotides against TGF-$\beta$RII inhibit the TGF-$\beta$1 induced down-regulation of adult neural stem and precursor proliferation in vitro.

It was shown that the TGF-$\beta$1 induced inhibition of neural stem and precursor proliferation was completely and specifically blocked by the antisense treatment.

Figure 7:
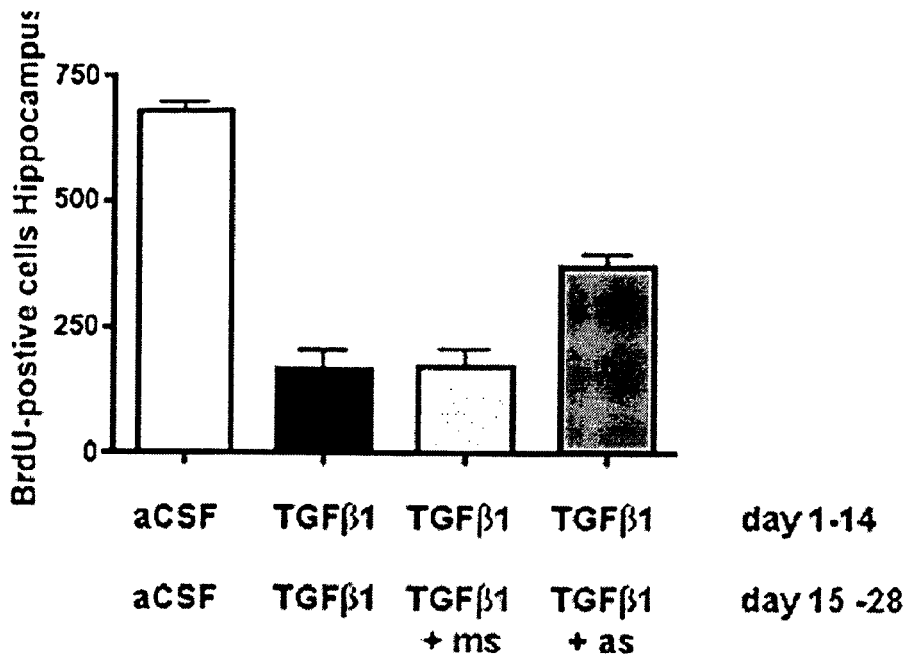
Figure 7:
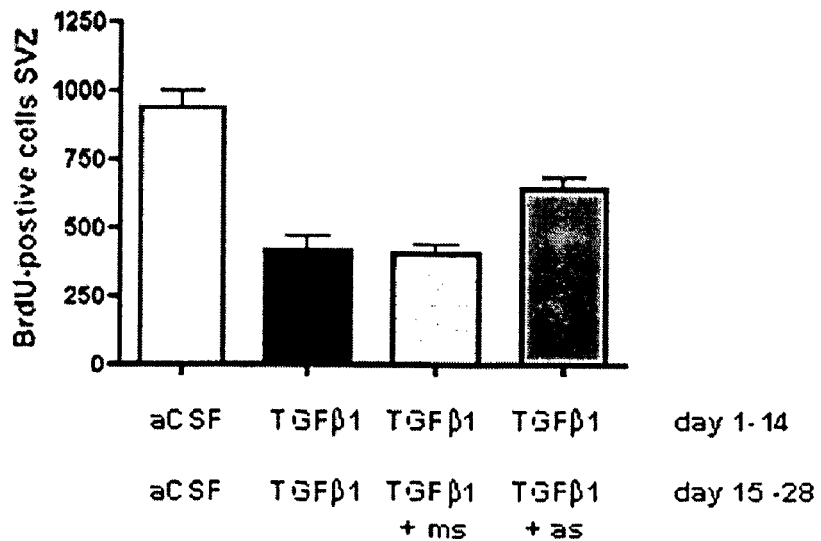

FIG. 7: In vivo treatment with TGF-RII specific antisense oligonucleotides rescues the TGF-$\beta$1 induced blockade of cell proliferation in the adult brain.

FIG. 7 demonstrates the TGF-$\beta$1 induced down-regulation of cell proliferation in the hippocampal dentate gyrus (FIG. 7A) and in the subventricular zone (FIG. 7B). Treatment with missense oligonucleotide did not block this effect, whereas antisense oligonucleotide treatment blocked the TGF-$\beta$1 effect (FIGS. 7 A and B).

Figure 8:
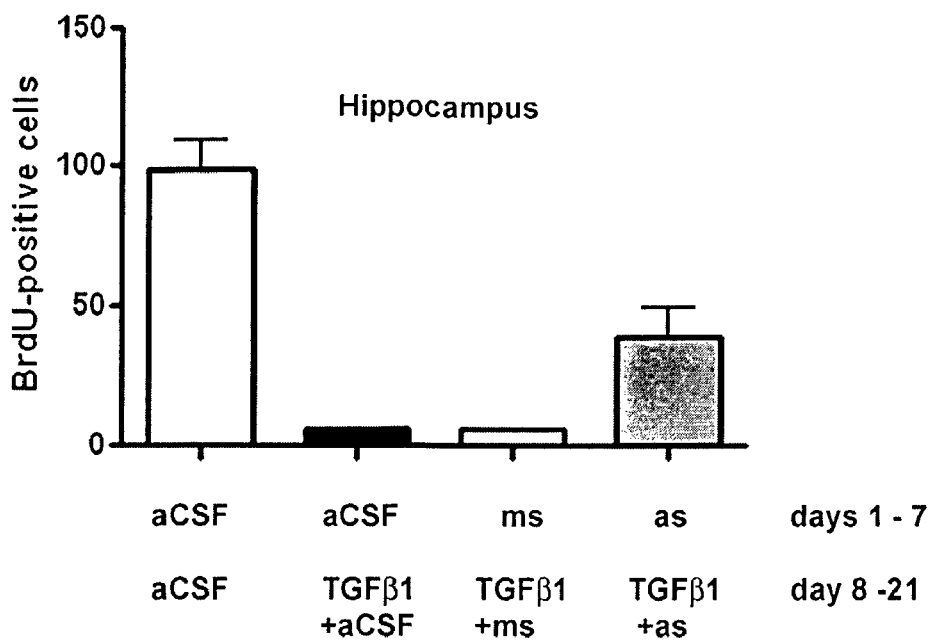
Figure 8:
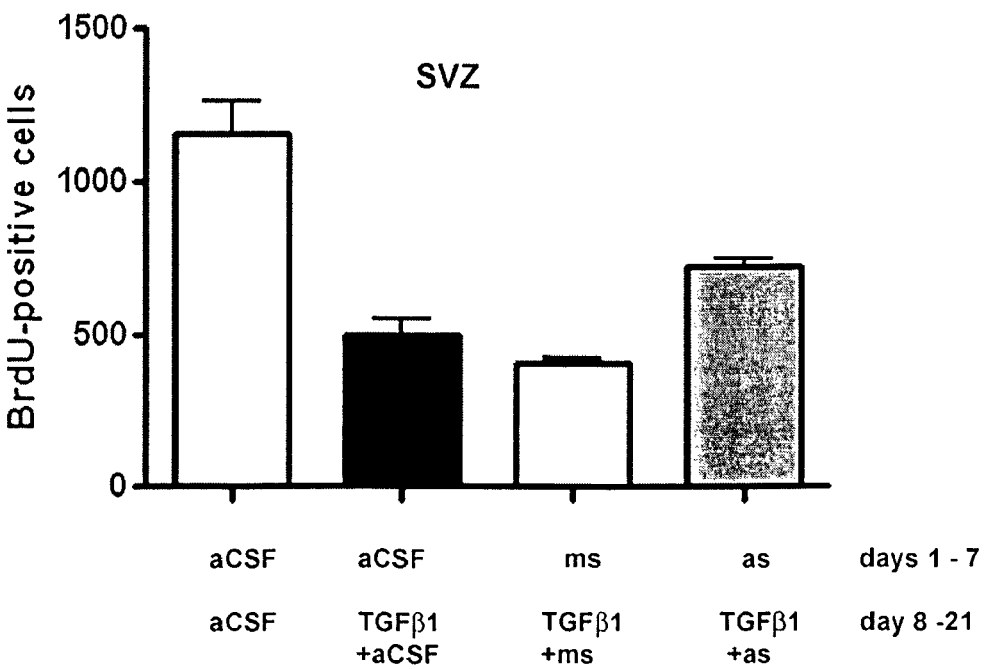

FIG. 8: In vivo treatment with TGF-RII specific antisense oligonucleotides prevent from TGF-$\beta$1 induced blockade of cell proliferation in the adult brain FIG. 8 demonstrates that the TGF-$\beta$1 induced down-regulation of cell proliferation in the hippocampal dentate gyrus (FIG. 8A) and in the subventricular zone (FIG. 8B) can be prevented by pre-treatment with TGF-$\beta$RII antisense oligonucleotide treatment.

In the disorders described above, microglial cells, and potentially perivascular resting macrophages, are attracted from protein aggregates, cell debris, inflammation, inflammatory response in atherosclerosis, or acute trauma/hypoxia associated cell death. This may be an acute, subacute or chronic process. During the activation process the activated microglial cell population (including macrophages from the vessel wall or other sources) releases a number of inflammatory cytokines into the extracellular matrix, draining either into small venules or directly into the CSF-space. These cytokines will reach the CSF-compartment and will be immediately available at all locations, which are surrounded to some extend by CSF. Among these cytokines is TGF-beta. It was demonstrated (Monje, M. L., H. Toda, et al. (2003). "Inflammatory blockade restores adult hippocampal neurogenesis." Science 302 (5651): 1760-1765) that neuroinflammation inhibits neurogenesis and that inflammatory blockade with indomethacin, a common nonsteroidal anti-inflammatory drug, restores neurogenesis after endotoxininduced inflammation and augments neurogenesis after cranial irradiation.

However, the prior art does not disclose TGF-beta as the main regulator down-regulating neurogenesis and neurorepair after injury or under pathological conditions. In contrast, the prior art considered TGF-beta as a neuroprotective agent preventing injured or lesioned neurons from cell death, and tried to up-regulate TGF-beta in CNS disease conditions.

Zhang et al. (Zhang, J. M., R. Hoffmann, et al. (1997). "Mitogenic and antiproliferative signals for neural crest cells and the neurogenic action of TGF-beta1." Dev. Dyn. 208(3): 375-386.) demonstrate that TGF-beta has an effect on developing quail neural crest cells. Here, TGF-beta inhibited proliferation of both pluripotent neural crest cells (and/or their immediate derivatives) and of committed melanogenic cells, causing a decrease in colony size. In addition, and in contrast to the present invention, neurogenesis increased significantly in the presence of TGF-beta. The number per colony of both adrenergic cells and sensory neuron precursors increased in TGF-beta-treated neuroblast-positive colonies.

TGF-betas have important roles in cell growth and differentiation, organ development, matrix formation, wound repair and immune function. While TGF-beta is a potent growth-inhibitory substance for many cell types, it stimulates proliferation of fibroblasts and osteoblasts. It is also a potent stimulator of extracellular matrix production by fibroblasts and osteoblasts, inhibits matrix degradation and up-regulates receptors for matrix interaction. TGF-beta1 has been implicated as a key causative factor in the pathogenesis of liver fibrosis and at least as one crucial mediator of both the beneficial and detrimental effects of cyclosporine A on the immune system and the kidney. In addition, various chronic progressive fibrotic kidney disorders in humans and experimental models have been shown to be associated with stimulation of the TGF-beta system.

TGF-beta1 down-regulates G1 and G2 cyclin-dependent kinases and cyclins in terms of both kinase activity and protein amount. TGF-beta1 also inhibits phosphorylation of the product of the retinoblastoma tumor suppressor gene pRb at multiple serine and threonine residues in human myeloid leukemia cells. The under-phosphorylated pRb associates with transcription factor E2F-4 in G1 phase, whereas the phosphorylated pRb mainly binds to E2F-1 and E2F-3. Because TGF-beta1 up-regulates p130 (pRb family member)/E2F-4 complex formation and down-regulates p107 (pRb family member)/E2F-4 complex formation, with E2F-4 levels remaining constant, these results suggest that E2F-4 is switched from p107 to pRb and p130 when cells exit from the cell cycle and arrest in G1 by the action of TGF-beta1. The "cdk inhibitor" p27 is both a positive and a negative regulator of TGF-beta1-mediated cell cycle control. Although TGF-beta1 has been reported to be a selected inhibitor of normal primitive hematopoietic stem cells, TGF-beta inhibits both primitive and more differentiated myeloid leukemia cell lines. Most attention was drawn on TGF-beta1's neuroprotective activity, its role in neural development and on its role in modulating immune responses. TGF-beta1 has been shown in a number of studies to be neuroprotective in vitro and in vivo. Agonist studies have demonstrated that TGF-beta1 reduces neuronal cell death and infarct size following middle cerebral artery occlusion (MCAO), while conversely, antagonist studies have shown increased neuronal cell death and infarct size after MCAO, suggesting that TGF-beta1 has a neuroprotective role in cerebral ischemia. Recent work with adenoviral-mediated overexpression of TGF-beta1 in vivo in mice has further implicated a neuroprotective role for TGF-beta1 in cerebral ischemia, as evidenced by a reduction in neuronal cell death, infarct size, and neurological outcome. Additionally, numerous in vitro studies have documented the neuroprotective ability of TGF-beta1 in neurons from a variety of species, including rats, mice, chicks, and humans. Of significant interest, TGFbeta1 was shown to be protective against a wide variety of death-inducing agents/insults, including hypoxia/ischemia, glutamate excitotoxicity, beta-amyloid, oxidative damage, and human immunodeficiency virus. The neuroprotective effect of TGF-beta1 has been related to its ability to maintain the mitochondrial membrane potential, to stabilize $Ca^{2+}$ homeostasis, to increase the expression of the anti-apoptotic proteins Bcl-2 and Bcl-xl, to inhibit caspase-3 activation and to induce plasminogen activator inhibitor-1. Studies in embryonic stem cells have demonstrated a primitive neural stem cell as a component of neural lineage specification that is negatively regulated by TGF-beta-related signalling. Endogenous expression of TGF-alpha, another TGF family member, has been shown to positively regulate adult neurogenesis. TGF-alpha is necessary for the full proliferation of progenitor cells present in the subependyma and the full production of the neuronal prescursors that migrate to the olfactory bulb. In TGF-alpha knock out mice, proliferation of these progenitor cells also is diminished with age, likely because of a lengthening of the cell cycle. Senescence or the absence of endogenous TGF-alpha does not affect the numbers of neural stem cells isolated in vitro in the presence of epidermal growth factor.

The use of TGF-beta for immunomodulation in humans is severely limited by its toxicity, including excessive stimulation of matrix production, nephrotoxicity and other detrimental effects. TGF-beta has oncogenic potential and has been implicated in glomerulopathies, pulmonary fibrosis, scleroderma and chronic graft versus host disease. In addition, while TGFbeta is an extremely potent immunosuppressive cytokine, several lines of evidence indicate that chronic stimulation of TGF-beta expression—both disease-related or in transgenic animal models—can paradoxically lead to or enhance autoimmune inflammation.

There is increasing evidence that the powerful anti-inflammatory properties of TGF-beta as a negative regulator of T-cell immune response play a key role in the pathophysiology of a variety of CNS pathologies. Therefore, this cytokine is regarded as an injury-related peptide and a potential target for therapeutic intervention. Neuroinflammation and microglial pathology are associated with many neurological diseases. Here, the most classical ones are clearly neuro-immunological diseases such as Multiple Sclerosis. But it includes also diseases of cognition in which memory loss features prominently, such as Alzheimer's Disease, Lewy Body Dementia, AIDS Dementia Complex, Vascular Dementia, or less prominently, such as Pick's Disease, Progressive Supranuclear Palsy, Corticobasal Degeneration, and Creutzfeldt-Jakob Disease. In addition, inflammatory programs are activated after acute lesions such as stroke, traumatic brain and spinal cord injuries. In different animal models for Creutzfeldt-Jacob Disease activation of microglia and up-regulation of TGF-beta1 has been reported (Baker, C. A., Z. Y. Lu, et al. (1999). "Microglial activation varies in different models of Creutzfeldt-Jakob disease." J Virol 73(6): 5089-5097).

Among the hundreds of different neurodegenerative disorders, the attention has been given only to a handful, including Alzheimer disease, Parkinson disease, Huntington's disease, and amyotrophic lateral sclerosis. It is worth to mention that the same neurodegenerative process can affect different areas of the brain, making a given disease appear very different from a symptomatic standpoint. Neurodegenerative disorders of the central nervous system (CNS) can be grouped into diseases of the cerebral cortex (Alzheimer disease), the basal ganglia (Parkinson disease), the brain-stem and cerebellum, or the spinal cord (Amoytrophic Lateral Sclerosis).

Examples for neurodegeneration and neurodegenerative disorders are: Alzheimer's diseases, Parkinson's disease, Creutzfeldt Jakobs disease (CJD), new variant of Creutzfeldt Jakobs disease (nvCJD), Hallervorden Spatz disease, Huntington's disease, multisystem atrophy, dementia, frontemporal dementia, motor neuron disorders, amyotrophic lateral sclerosis, spinal muscular atrophy, spinocerebellar atrophies (SCAB), schizophrenia, affective disorders, major depression, meningoencephalitis, bacterial meningoencephalitis, viral meningoencephalitis, CNS autoimmune disorders, Multiple Sclerosis (MS), acute ischemic/hypoxic lesions, CNS trauma, head trauma, arteriosclerosis, atherosclerosis, microangiopathic dementia, Binswanger' disease Leukoaraiosis, retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellear degeneration (OPCD), Shy Drager syndrome (SDS).

Influencing the Levels of TGF-Beta1
Up-Regulation of TGF-Beta1 and its Effects

Many studies tried to increase TGF-beta1 levels for neuroprotective or immunoregulatory purposes. Agonist studies have demonstrated that TGF-beta1 reduces neuronal cell death and infarct size following middle cerebral artery occlusion (MCAO), while conversely, antagonist studies have shown increased neuronal cell death and infarct size after MCAO, suggesting that TGF-beta1 has a neuroprotective role in cerebral ischemia. Recent work with adenoviral-mediated overexpression of TGF-beta1 in vivo in mice has further implicated a neuroprotective role for TGF-beta1 in cerebral ischemia, as evidenced by a reduction in neuronal cell death, infarct size, and neurological outcome. Additionally, numerous in vitro studies have documented the neuroprotective ability of TGF-beta1 in neurons from a variety of species, including rats, mice, chicks, and humans. Of significant interest, TGFbeta1 was shown to be protective against a wide variety of death-inducing agents/insults, including hypoxialischemia, glutamate excitotoxicity, beta-amyloid, oxidative damage, and human immunodeficiency virus. The neuroprotective effect of TGF-beta1 has been related to its ability to maintain the mitochondrial membrane potential, to stabilize $Ca^{2+}$ homeostasis, to increase the expression of the anti-apoptotic proteins Bcl-2 and Bcl-xl, to inhibit caspase-3 activation and to induce plasminogen activator inhibitor-1.

The use of TGF-beta for immunomodulation in humans is severely limited by its toxicity, including excessive stimulation of matrix production, nephrotoxicity and other detrimental effects. TGF-beta has oncogenic potential and has been implicated inglomerulopathies, pulmonary fibrosis, scleroderma and chronic graft versus host disease. In addition, while TGF beta is an extremely potent immunosuppressive cytokine, several lines of evidence indicate that chronic stimulation of TGF-beta expression—both disease-related or in transgenic animal models—can paradoxically lead to or enhance autoimmune inflammation.

Our main finding is that the identical TGF-β described in it's protective effects upon the CNS above, is the main negative regulatory molecule of CNS-stem cell repair in physiology and in almost all CNS pathology: TGF-1'-produced by microglial cells (either at low physiological levels or at higher levels in response to disease) leaks through the intercellular matrix into the CSF. There it may freely and directly interact with highly regulated and expressed TGF-RII and TGF-RI on the precursor/stem cell population of the CNS at the subependymal progenitor-containing cell layer zone or potentially other areas of CNS-stem cell renewal. The finding consists of a negative regulation, resulting in low stem cell renewal in case of high CSF-TGF-β levels and vice versa. Unusual and most remarkably, the extreme high expression level and activity of TGF-RII is located at the site of precursor/stem cell proliferation, in our experiments the SVZ or the hippocampus. Unusual is also the transmission of the signal through a buffering solution, as for example cerebrospinal fluid (CSF). It is therefore a complete regulatory circle, where physiological and pathological regulation are very similar, but vary only by intensity (in other words: the level of TGF-β in the CSF, and level of TGF-R expression at the target cells). The individual disease pathology phenotype is characterized by such diverse changes, as genetic deficits (e.g. Synucleinopathies, Superoxide Dismutase Mutations, Trinucleotide Repeat Disorders) or trauma, hypoxia, vascular disease or inflammation, or CNS-ageing. The executor of the disease pathology, however, is always the microglial cell/macrophage population—produced TGF-β: On one hand it is neuroprotective and immunosuppressive, helping to deescalate the acute inflammatory damage to the parenchyma and the neuronal loss potentially inflicted by the disease pathology. Indirectly—as a Janus Head—the same molecule prevents the CNS from damage repair by the own stem cells/precursor cells through interfering with the TGF-β-TGF-R loop at the precursor or stem cell level, thereby significantly suppressing stem cell proliferation. In this case, as stem cells not only those cells derived from precursor cells from within the CNS should be looked at, but conceivably also those stem cells/precursor cells that try to invade the CNS parenchyma from the vessels respectively the bone marrow. This also means that by simply decreasing TGF-β levels in the parenchyma, the neuroprotective/immunosuppressive effects upon the CNS would be annihilated leading to severe acute damage by inflammation and/or direct neuronal apoptosis.

A local intervention at the TGF-R-level therefore seems the only attractive pathway for stable intervention in favour of repair, not endangering the beneficial effects of TGF-β for the brain. Thus, the present invention relates to antisense oligonucleotides interfering with the biological activity of TGF-beta1 upon the precursor/stem cell pool expressing TGF-R. Said oligonucleotides or pharmaceutical compositions including at least one of said oligonucleotides are useful for the diagnosis/prophylaxis/prevention or treatment of a disease, wherein neurogenesis or neuroregeneration has a beneficial effect. They are also useful in the therapeutic prevention (for example after stroke or head injury)—as shown in our experiments—before the mechanisms described hereafter will be effective.

The term "interfering" as used herein means modulating, preferably reducing or eliminating, the biological activity of TGF-R and/or TGF-$R_{II}$ or its expression. The modulation of the biological activity can be effected by direct interaction or binding of a compound to TGF-R, preferably, TGF-$R_{II}$ or by indirect interaction, e.g., by interacting with a compound that is associated with the biological activity of TGF-R and/or TGF-$R_{II}$. Suitable compounds acting as agents targeting TGF-beta$R_I$, —$R_{II}$, —$R_{III}$, or its signal transduction to interfere with this regulatory circuit with the aim to improve neuroregeneration or increase neuronal/hematopoetic stem cell or precursor cell recruitment to the CNS, including all types of local or systemic transplantation (e.g. ex vivo propagation, allogeneic cells) are listed below:

(a) Plasmids, vectors or natural/synthetic/mutated viruses, oligonucleotides of various types of modification (e.g. PTO, LNA, 2'F-ANA, protein-nucleotide complexes, RNAi, siRNA or mikro miRNA, Methylmetoxy-, Phosphoroamidates, PNA, Morpholino, Phosphoramidate, Cyclohexen (CeNA), gap-meres, ribozymes, aptamers, CpG-oligos, DNA-zymes, riboswitches, or lipids or lipid containing molecules, (b) peptides, peptide complexes, including all types of linkers, (c) small molecules, modifyers of rafts or caveoli, (d) modifyers of golgi apparatus, (e) antibodies and their derivatives, especially chimeras, Fab-fragments, Fc-fragments, or (f) carriers, liposomes, nanoparticles, complexes, or any other delivery systems containing the above named constructs, can be used to target the above mentioned circuit to restore or improve neuroregeneration.

However, most preferred among the above-mentioned agents are antisense oligonucleotides, since they interfere with the formation of TGF-R or TGF-$R_{II}$ at a very early stage. The main advantages of these molecules rest in their extremely high target specificity, combined with their extremely good systemic and local tolerance; they are very well suited for local application into the CNS, either into the parenchyma or the CSF-space. In addition, they are very stable, and may thus be easily applied from an implanted pumping system. Their cost-efficacy is also remarkable.

Thus, in preferred embodiments of the present invention, the compound useful for interfering with the expression of the gene encoding TGF-R or TGF-$R_{II}$, is an antisense oligonucleotide.

The generation of suitable antisense oligonucleotides includes determination of a site or sites within the TGF-R gene or TGF-$R_{II}$ gene for the antisense interaction to occur such that the desired effect, e.g., inhibition of expression of the protein, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect.

Thus, the present invention relates to antisense oligonucleotides having a sub-sequence of SEQ ID NO 1 or SEQ ID NO 2 or SEQ ID NO 94 or SEQ ID NO 95 or SEQ ID NO 96 comprising 8 to 50 nucleobases and mimetics thereof. Said oligonucleotides represent a part of the SEQ ID NO 1 or 2 or SEQ ID NO 94 to 96 with 8 to 50 nucleotide bases. Furthermore, the antisense oligonucleotides comrising 8 to 50 nucleobases do not have to be an exact sub-sequence of SEQ ID NO 1 or 2 or SEQ ID NO 94 to 96. It is sufficient if the antisense oligonucleotides are at least 80%, preferably 84%, more preferably 88% and most preferably 92% identical to a sub-sequence found in of SEQ ID NO 1 or 2 or SEQ ID NO 94 or 95 or 96. Preferred oligonucleotides have a sequence at least 80% identical to a sub-sequence of SEQ ID NO 1 or 2 or 94 or 95 or 96 comprising 8 to 50 nucleobases, wherein said sequence is capable of hybridizing sufficiently with the region encompassing the translation initiation or termination codon of the open reading frame of the gene encoding TGF-R or TGF-R$_{II}$, or a region of the mRNA encoding TGF-R or TGF-R$_{II}$ which is a "loop" or "bulge" and which is not part of a secondary structure. That means, these antisense oligonucleotides have a sequence at least 80% complementary with the corresponding region of the gene encoding TGF-R or TGE-R$_{II}$, or preferably have a sequence at least 80% complementary with (a) the region encompassing the translation initiation or termination codon of the open reading frame of the gene encoding TGF-R or TGF-R$_{II}$, or (b) a region of the mRNA encoding TGF-R or TGF-R$_{II}$ which is a "loop" or "bulge", i.e., not part of a secondary structure.

Preferred are antisense oligonucleotides of 8 to 50, preferably 15 to 25 nucleobases, able to hybridize sufficiently with the region encompassing the translation initiation or termination codon of the open reading frame of the gene encoding TGF-R or TGE-R$_{II}$, or a region of the mRNA encoding TGF-R or TGF-R$_{II}$ which is a "loop" or "bulge" and which is not part of a secondary structure.

Preferred are the following elongated sequences of SEQ ID NO 3 which can be represented by the following general formula:

5'-XCAGCCCCGACCCATGZ-3'   SEQ ID NO:101 wherein X is selected from the group comprising the following oligonucleotides:

ACAGGACGATGTGCAGCGGCCACAGGCCCCTGAG, SEQ ID NO: 102

CAGGACGATGTGCAGCGGCCACAGGCCCCTGAG, SEQ ID NO: 103

AGGACGATGTGCAGCGGCCACAGGCCCCTGAG, SEQ ID NO: 104

GGACGATGTGCAGCGGCCACAGGCCCCTGAG, SEQ ID NO: 105

GACGATGTGCAGCGGCCACAGGCCCCTGAG, SEQ ID NO: 106

ACGATGTGCAGCGGCCACAGGCCCCTGAG, SEQ ID NO: 107

CGATGTGCAGCGGCCACAGGCCCCTGAG, SEQ ID NO: 108

GATGTGCAGCGGCCACAGGCCCCTGAG, SEQ ID NO: 109

ATGTGCAGCGGCCACAGGCCCCTGAG, SEQ ID NO: 110

TGTGCAGCGGCCACAGGCCCCTGAG, SEQ ID NO: 111

GTGCAGCGGCCACAGGCCCCTGAG, SEQ ID NO: 112

TGCAGCGGCCACAGGCCCCTGAG, SEQ ID NO: 113

GCAGCGGCCACAGGCCCCTGAG, SEQ ID NO: 114

CAGCGGCCACAGGCCCCTGAG, SEQ ID NO: 115

AGCGGCCACAGGCCCCTGAG, SEQ ID NO: 116

GCGGCCACAGGCCCCTGAG, SEQ ID NO: 117

CGGCCACAGGCCCCTGAG, SEQ ID NO: 118

GGCCACAGGCCCCTGAG, SEQ ID NO: 119

GCCACAGGCCCCTGAG, SEQ ID NO: 120

CCACAGGCCCCTGAG, SEO ID NO: 121

CACAGGCCCCTGAG, SEQ ID NO: 122

ACAGGCCCCTGAG, SEO ID NO: 123

CAGGCCCCTGAG, SEQ ID NO: 124

AGGCCCCTGAG, SEQ ID NO: 125

GGCCCCTGAG, SEQ ID NO: 126

GCCCCTGAG, SEQ ID NO: 127

CCCCTGAG, SEO ID NO: 128

CCCTGAG, SEQ ID NO: 129

CCTGAG, SEQ ID NO: 130

CTGAG, SEO ID NO: 131

TGAG, SEQ ID NO: 132

GAG, AG, G, and wherein Z is selected from the group comprising the following oligonucleotides:

GCAGACCCCGCTGCTCGTCATAGACCGAGCCCCC, SEQ ID NO: 133

GCAGACCCCGCTGCTCGTCATAGACCGAGCCCC, SEO ID NO: 134

GCAGACCCCGCTGCTCGTCATAGACCGAGCCC, SEQ ID NO: 135

GCAGACCCCGCTGCTCGTCATAGACCGAGCC, SEQ ID NO: 136

GCAGACCCCGCTGCTCGTCATAGACCGAGC, SEQ ID NO: 137

GCAGACCCCGCTGCTCGTCATAGACCGAG, SEQ ID NO: 138

GCAGACCCCGCTGCTCGTCATAGACCGA, SEQ ID NO: 139

GCAGACCCCGCTGCTCGTCATAGACCG, SEQ ID NO: 140

GCAGACCCCGCTGCTCGTCATAGACC, SEQ ID NO: 141

GCAGACCCCGCTGCTCGTCATAGAC, SEQ ID NO: 142

GCAGACCCCGCTGCTCGTCATAGA, SEQ ID NO: 143

GCAGACCCCGCTGCTCGTCATAG, SEO ID NO: 144

GCAGACCCCGCTGCTCGTCATA, SEQ ID NO: 145

GCAGACCCCGCTGCTCGTCAT, SEQ ID NO: 146

GCAGACCCCGCTGCTCGTCA, SEO ID NO: 147

GCAGACCCCGCTGCTCGTC, SEQ ID NO: 148

GCAGACCCCGCTGCTCGT, SEQ ID NO: 149

GCAGACCCCGCTGCTCG, SEQ ID NO: 150

GCAGACCCCGCTGCTC, SEQ ID NO: 151

GCAGACCCCGCTGCT, SEQ ID NO: 152

GCAGACCCCGCTGC, SEQ ID NO: 153

GCAGACCCCGCTG, SEQ ID NO: 154

GCAGACCCCGCT, SEQ ID NO: 155

GCAGACCCCGC, SEQ ID NO: 156

GCAGACCCCG, SEQ ID NO: 157

GCAGACCCC, SEQ ID NO: 158

GCAGACCC, SEQ ID NO: 159

GCAGACC, SEQ ID NO: 160

GCAGAC, SEQ ID NO: 161

GCAGA, SEQ ID NO: 162

GCAG, SEQ ID NO: 163

GCA, GC, G, and wherein X and Z together comprise not more than 34 nucleobases and mimetics thereof.

More preferred are the following oligonucleotide sequences and variants or mimetics thereof:

| | |
|---|---|
| SEQ ID NO 3: | 5'-CAGCCCCGACCCATG-3' |
| SEQ ID NO 4: | 5'-GCTGATGCCTGTCACTTGAA-3' |
| SEQ ID NO 5: | 5'-GCCATGGAGTAGACATCGGT-3' |
| SEQ ID NO 6: | 5'-GCAACAGCTATTGGGATGGT-3' |
| SEQ ID NO 7: | 5'-GTGCAGGGGAAAGATGAAAA-3' |
| SEQ ID NO 8: | 5'-GTATCAGCATGCCCTACGGT-3' |
| SEQ ID NO 9: | 5'-GGATCCAGATTTTCCTGCAA-3' |
| SEQ ID NO 10: | 5'-GGAGAAGCAGCATCTTCCAG-3' |
| SEQ ID NO 11: | 5'-GAGCTCTTGAGGTCCCTGTG-3' |
| SEQ ID NO 12: | 5'-GAGACCTTCCACCATCCAAA-3' |
| SEQ ID NO 13: | 5'-TAGCTGGCTGTGAGACATGG-3' |
| SEQ ID NO 14: | 5'-TTTTGAAACGCTGTGCTGAC-3' |
| SEQ ID NO 15: | 5'-TCAGCCAGTATTGTTTCCCC-3' |
| SEQ ID NO 16: | 5'-TCACACAGGCAGCAGGTTAG-3' |
| SEQ ID NO 17: | 5'-TCAGGAATCTTCTCCTCCGA-3' |
| SEQ ID NO 18: | 5'-TGGTAGTGTTTAGGGAGCCG-3' |
| SEQ ID NO 19: | 5'-TATCCCCACAGCTTACAGGG-3' |
| SEQ ID NO 20: | 5'-AGCCTCTTTCCTCATGCAAA-3' |
| SEQ ID NO 21: | 5'-ATGTCATTTCCCAGAGCACC-3' |
| SEQ ID NO 22: | 5'-AGGAATCTTCTCCTCCGAGC-3' |
| SEQ ID NO 23: | 5'-AGCCATGGAGTAGACATCGG-3' |
| SEQ ID NO 24: | 5'-ATGCTACTGCAGCCACACTG-3' |
| SEQ ID NO 25: | 5'-CCTTCTCTGCTTGGTTCTGG-3' |
| SEQ ID NO 26: | 5'-CCAGGAGAAATAAGGGCACA-3' |
| SEQ ID NO 27: | 5'-CAGCAGCTCTGTGTTGTGGT-3' |
| SEQ ID NO 28: | 5'-CCCACTGTTAGCCAGGTCAT-3' |
| SEQ ID NO 29: | 5'-CAGCCCCGACCCATGGCAGACCC-3' |
| SEQ ID NO 30: | 5'-CAGCCCCGACCCATGGCAGACC-3' |
| SEQ ID NO 31: | 5'-CAGCCCCGACCCATGGCAGAC-3' |
| SEQ ID NO 32: | 5'-CAGCCCCGACCCATGGCAGA-3' |
| SEQ ID NO 33: | 5'-CAGCCCCGACCCATGGCAG-3' |
| SEQ ID NO 34: | 5'-CAGCCCCGACCCATGGCA-3' |
| SEQ ID NO 35: | 5'-CAGCCCCGACCCATGGC-3' |
| SEQ ID NO 36: | 5'-CAGCCCCGACCCATGG-3' |
| SEQ ID NO 37: | 5'-GCAGCCCCGACCCATGGCAGACC-3' |
| SEQ ID NO 38: | 5'-GCAGCCCCGACCCATGGCAGAC-3' |
| SEQ ID NO 39: | 5'-GCAGCCCCGACCCATGGCAGA-3' |
| SEQ ID NO 40: | 5'-GCAGCCCCGACCCATGGCAG-3' |
| SEQ ID NO 41: | 5'-GCAGCCCCGACCCATGGCA-3' |
| SEQ ID NO 42: | 5'-GCAGCCCCGACCCATGGC-3' |
| SEQ ID NO 43: | 5'-GCAGCCCCGACCCATGG-3' |
| SEQ ID NO 44: | 5'-GCAGCCCCGACCCATG-3' |
| SEQ ID NO 45: | 5'-AGCAGCCCCGACCCATGGCAGAC-3' |
| SEQ ID NO 46: | 5'-AGCAGCCCCGACCCATGGCAGA-3' |
| SEQ ID NO 47: | 5'-AGCAGCCCCGACCCATGGCAG-3' |
| SEQ ID NO 48: | 5'-AGCAGCCCCGACCCATGGCA-3' |
| SEQ ID NO 49: | 5'-AGCAGCCCCGACCCATGGC-3' |
| SEQ ID NO 50: | 5'-AGCAGCCCCGACCCATGG-3' |
| SEQ ID NO 51: | 5'-AGCAGCCCCGACCCATG-3' |
| SEQ ID NO 52: | 5'-GAGCAGCCCCGACCCATGGCAGA-3' |
| SEQ ID NO 53: | 5'-GAGCAGCCCCGACCCATGGCAG-3' |
| SEQ ID NO 54: | 5'-GAGCAGCCCCGACCCATGGCA-3' |
| SEQ ID NO 55: | 5'-GAGCAGCCCCGACCCATGGC-3' |
| SEQ ID NO 56: | 5'-GAGCAGCCCCGACCCATGG-3' |
| SEQ ID NO 57: | 5'-GAGCAGCCCCGACCCATG-3' |
| SEQ ID NO 58: | 5'-TGAGCAGCCCCGACCCATGGCAG-3' |
| SEQ ID NO 59: | 5'-TGAGCAGCCCCGACCCATGGCA-3' |
| SEQ ID NO 60: | 5'-TGAGCAGCCCCGACCCATGGC-3' |
| SEQ ID NO 61: | 5'-TGAGCAGCCCCGACCCATGG-3' |
| SEQ ID NO 62: | 5'-TGAGCAGCCCCGACCCATG-3' |
| SEQ ID NO 63: | 5'-CTGAGCAGCCCCGACCCATGGCA-3' |
| SEQ ID NO 64: | 5'-CTGAGCAGCCCCGACCCATGGC-3' |

```
SEQ ID NO 65:   5'-CTGAGCAGCCCCCGACCCATGG-3'
SEQ ID NO 66:   5'-CTGAGCAGCCCCCGACCCATG-3'
SEQ ID NO 67:   5'-CCTGAGCAGCCCCCGACCCATGGC-3'
SEQ ID NO 68:   5'-CCTGAGCAGCCCCCGACCCATGG-3'
SEQ ID NO 69:   5'-CCTGAGCAGCCCCCGACCCATG-3'
SEQ ID NO 70:   5'-CCCTGAGCAGCCCCCGACCCATGG-3'
SEQ ID NO 71:   5'-CCCTGAGCAGCCCCCGACCCATG-3'
SEQ ID NO 72:   5'-CCCCTGAGCAGCCCCCGACCCATG-3'
```

Still more preferred are the following oligonucleotide sequences as well as variants and mimetics thereof:

```
SEQ ID NO 33:   5'-CAGCCCCCGACCCATGGCAG-3'
SEQ ID NO 34:   5'-CAGCCCCCGACCCATGGCA-3'
SEQ ID NO 35:   5'-CAGCCCCCGACCCATGGC-3'
SEQ ID NO 36:   5'-CAGCCCCCGACCCATGG-3'
SEQ ID NO 41:   5'-GCAGCCCCCGACCCATGGCA-3'
SEQ ID NO 42:   5'-GCAGCCCCCGACCCATGGC-3'
SEQ ID NO 43:   5'-GCAGCCCCCGACCCATGG-3'
SEQ ID NO 44:   5'-GCAGCCCCCGACCCATG-3'
SEQ ID NO 49:   5'-AGCAGCCCCCGACCCATGGC-3'
SEQ ID NO 50:   5'-AGCAGCCCCCGACCCATGG-3'
SEQ ID NO 51:   5'-AGCAGCCCCCGACCCATG-3'
SEQ ID NO 56:   5'-GAGCAGCCCCCGACCCATGG-3'
SEQ ID NO 57:   5'-GAGCAGCCCCCGACCCATG-3'
SEQ ID NO 62:   5'-TGAGCAGCCCCCGACCCATG-3'
SEQ ID NO 73:   5'-ATGTGAAGATGGGCAAGACC-3'
SEQ ID NO 74:   5'-ATCTCCATGTGAAGATGGGC-3'
SEQ ID NO 75:   5'-AACGGCCTATCTCGAGGAAT-3'
SEQ ID NO 76:   5'-AACATCGTCGAGCAATTTCC-3'
SEQ ID NO 77:   5'-AATCCAACTCCTTTGCCCTT-3'
SEQ ID NO 78:   5'-AAACCTGAGCCAGAACCTGA-3'
SEQ ID NO 79:   5'-AGGGCGATCTAATGAAGGGT-3'
SEQ ID NO 80:   5'-AGTGCACAGAAAGGACCCAC-3'
SEQ ID NO 81:   5'-ACACTGGTCCAGCAATGACA-3'
SEQ ID NO 82:   5'-TTCCTGTTGACTGAGTTGCG-3'
SEQ ID NO 83:   5'-CACTCTGTGGTTTGGAGCAA-3'
SEQ ID NO 84:   5'-CAAGGCCAGGTGATGACTTT-3'
SEQ ID NO 85:   5'-CACACTGGTCCAGCAATGAC-3'
SEQ ID NO 86:   5'-CTGACACCAACCAGAGCTGA-3'
SEQ ID NO 87:   5'-CTCTGCCATCTGTTTGGGAT-3'
SEQ ID NO 88:   5'-TCAAAAAGGGATCCATGCTC-3'
SEQ ID NO 89:   5'-TGACACCAACCAGAGCTGAG-3'
SEQ ID NO 90:   5'-TGATGCCTTCCTGTTGACTG-3'
SEQ ID NO 91:   5'-TTCCTGTTGACTGAGTTGCG-3'
SEQ ID NO 92:   5'-TTCTCCAAATCGACCTTTGC-3'
SEQ ID NO 93:   5'-GGAGAGTTCAGGCAAAGCTG-3'
```

Excluded from the scope of the present substance claims are the following two known sequences: 5'-GATCTTGACTGCCACTGTCTC-3' (SEQ ID NO: 97) (J. Clin. Endocrinology & Metabolism 2003, 88(10), 4967-4976) and 5'-CATGGCAGCCCCCGTC-3' (SEQ ID NO: 98) (Developmental Biology 1996, 180, 242-257).

Especially preferred is the sequence SEQ ID NO 3: 5'-CAGCCCCCGACCCATG-3'.

Consequently, the present invention is also directed to sequences which are closely related to any one of SEQ ID NO 3 to SEQ ID NO 93. Said sequences are referred to as "variants" herein. The antisense oligonucleotides can be modified by several different ways. Modifications within the backbone are possible and refer to oligonucleotides wherein the phosphorus atoms in their internucleoside backbone are partially or completely replaced by other atoms. Preferred modified oligonucleotide backbones include, for instance, phosphorothioates, chiral phorphorothioates, phosphorodithioates, phosphotriester, aminoalkylphosphotriesters, methyl, ethyl and $C_3$-$C_{10}$-alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acids forms thereof are also included.

Preferred are also variants of SEQ ID NO 3 to SEQ ID NO 93 wherein at the 3' terminal end and/or at the 5' terminal end 1, 2, 3, 4, or 5 further nucleobases are added. Such further nucleobases are preferably the five nucleobases within the SEQ ID NOs 1, 2, 94, 95, or 96 which come directly prior or after the respective sequence. Furthermore, said preferred variants may have 1, 2, 3, or 4 nucleobase exchanges, i.e. within said preferred variants, one, two, three or four nucleotides may be substituted by another nucleobase. It should be stressed that these variants may also contain any of the modifications of the backbone or the base or sugar moiety disclosed herein, such as phosphorothioate backbones.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages. These include those having morpholino linkages (formed in part from the sugar portion of a nucleoside); siloxane backbones, sulfide, sulfoxide and sulfone backbones; formacetyl and thioformacetyl backbones; methylene formacetyl and thioformacetyl backbones, alkene containing backbones, sulfamate backbones; methyleneimino and methylenehydrazino backbones; sulfonate and sulfonamide backbones; amide backbones, mixtures of the aforementioned types of backbones and other backbones having mixed N, O, S, P, and $CH_2$ component parts.

Further preferred embodiments of the present invention comprise oligonucleotides with phosphorothioate backbones or heteroatom backbones, and in particular with —$CH_2$—

NH—O—CH$_2$—, —CH$_2$—N(CH$_3$)—O—CH$_2$—(known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$—(wherein the native phosphodiester backbone is represented as —O—P—O—CH$_2$—). Also oligonucleotides having morpholino moieties in their backbone or having a morpholino backbone structure or having a aminoalkylamide backbone are preferred (cf. below). Oligonucleotides may also have sugar mimetics such as cyclobutyl moieties in place of the pentofuranosyl sugar.

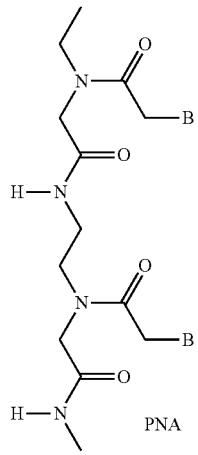

PNA

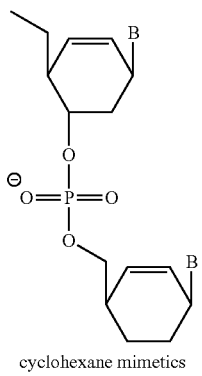

cyclohexane mimetics

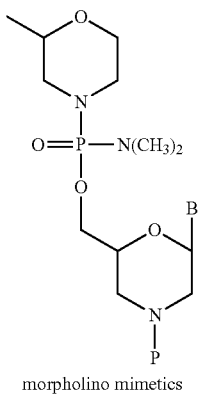

morpholino mimetics

B refers to the base moiety such as the purin or pyrimidin group which may be further derivatized.

Another modification of the oligonucleotides of the present invention involves chemically linking to the oligonucleotide one or more moieties or conjugates which enhance the activity, cellular distribution or cellular uptake of the oligonucleotide. Modified oligonucleotides may also contain one or more substituted or modified sugar moieties. Preferred oligonucleotides comprise one of the following at the 2' position: —OH, —F, —O-alkyl, —S-alkyl, —N-alkyl, —O-alkenyl, —S-alkenyl, —N-alkenyl, —O-alkynyl, —S-alkynyl, —N-alkynyl, —O-alkyl-O-alkyl, wherein the alkyl, alkenyl and alkynyl may be substituted or unsubstituted $C_1$ to $C_{10}$ alkyl or $C_2$ to $C_{10}$ alkenyl and $C_2$ to $C_{10}$ alkynyl. A particularly preferred modified sugar moiety is a 2'-O-methoxyethyl sugar moiety (2'-OCH$_2$CH$_2$OCH$_3$, also known as 2'-O-(2-methoxyethoxy) or 2'-MOE) and 2'-dimethylaminooxyethoxy such as O(CH$_2$)$_2$ON(CH$_3$) (known as 2'-DMAOE). Also particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, O(CH$_2$)$_n$ON[(CH$_2$)$_n$CH$_3$], where n and m are independently of each other integer from 1 to 10. Other preferred modifications include 2'-methoxy, 2'-aminopropoxy and 2'-fluoro. Other preferred oligonucleotides comprise one of the following groups at the 2' position: —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —NO$_2$, —F, —Cl, —Br, —I, —N$_3$, —CN, —OCN, —NCO, —SCN, —NCS, —COCH$_3$, —COC$_2$H$_5$, —COC$_3$H$_7$, —CO-cyclo-C$_3$H$_5$, —COCH(CH$_3$)$_2$, —CF$_3$, —SH, —SCH$_3$, —SC$_2$H$_5$, —SC$_3$H$_7$, —S-cyclo-C$_3$H$_5$, —SOCH$_3$, —SOC$_2$H$_5$, —SOC$_3$H$_7$, —SO-cyclo-C$_3$H$_5$, —SO$_2$CH$_3$, —SO$_2$C$_2$H$_5$, —SO$_2$C$_3$H$_7$, —SO$_2$-cyclo-C$_3$H$_5$, —NH$_2$, —NHCH$_3$, —NHC$_2$H$_5$, —NHC$_3$H$_7$, —NH-cyclo-C$_3$H$_5$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$—CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —C$_2$H$_4$—C(CH$_3$)$_3$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —CH(CH$_3$)—C(CH$_3$)$_3$, C$_7$-C$_{10}$ alkyl, substituted C$_1$-C$_{10}$ alkyl, alkylaryl, arylalkyl, O—C$_1$-C$_{10}$ alkyl, O-arylalkyl, heterocycloalkyl, heterocycloalkylaryl, aminoalkylamino, polyalkylamino, substituted silyl, an RNA leaving group, a reporter group, an intercalator, a group for improving the pharmacokinetic and/or pharmacodynamic properties of the oligonucleotide, or substituents having similar properties. Also preferred are the deoxy nucleobases.

Similar modifications may also be made at other positions on the nucleotide, particularly the 3' position of the sugar on the 3' terminal nucleotide or in 2'-5' linked oligonucleotides and the 5' position of 5' terminal nucleotide.

Preferred modifications can be represented by the following structure fragment:

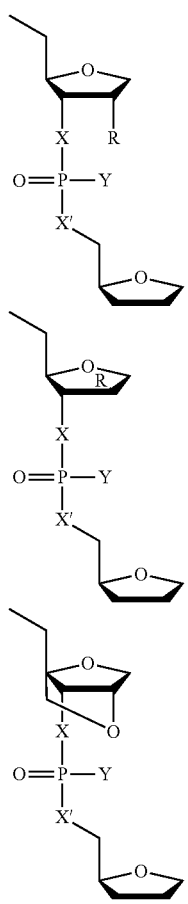

wherein

R represents any of the above-mentioned substituents for position 2' and especially —H, —F, —OH, —NH$_2$, —OCH$_3$, —OCH$_2$CH$_2$OCH$_3$, X and X' are independently of each other —O—, —NH—, —S—, —CH$_2$—, and Y represents —O", —S", —N(CH$_3$)$_2$, —OCH$_3$, —SCH$_3$.

More preferred are variants wherein X and X' represent oxygen and Y represents sulfur.

Furthermore, pure diastereomeric oligonucleotides or mimetics or variants thereof are preferred. Especially preferred are Sp- and Rp-diastereomers:

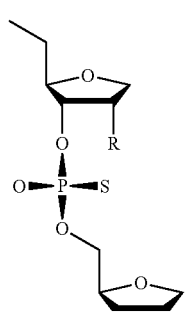

Rp diastereomer

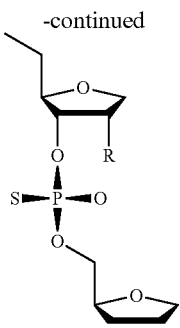

Sp diastereomer

Most preferred are also the sequences SEQ ID NO 3 to SEQ ID NO 93, and especially SEQ ID NO 3, wherein one or more of the modifications disclosed herein are present. Preferred are phosphorothioate moieties in the backbone or complete phosphorotioate backbones and within said phosphorothioates the Rp and Sp diastereomers are preferred.

The oligonucleotides of the present invention may also include nucleobase substitutions. Nucleobases are the four standard nucleotide bases adenine (A), thymine (T), guanine (G), and cytosine (C). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine; uracile (U), 6-carboxyuracile, N$^6$-methyl-adenine, 5-halouracil, 5-halocytosine, 5-propynyl uracil, 5-propynyl cytosine, 6-azo uracil, 6-azo cytosine, 6-azo thymine, 5-uracil (pseudouracil), 4-thiouracil; 8-halo-, 8-amino-, 8-thiol-, 8-thioalkyl-, 8-hydroxyl- and other 8-substituted adenines and guanines; 5-halo-particularly 5-bromo-, 5-trifluoromethyl- and other 5-substituted uracils and cytosines; 7-methylguanine; 7-methyladenine, 8-azaguanine, 8-azaadenine, 7-deazaguanine, 7-deazaadenine, 3-deazaguanine and 3-deazaadenine, 2-thiouracil, 2-thiothymine and 2-thiocytosine etc., with 5-methylcytosine substitutions being preferred since these modifications have been shown to increase nucleic acid duplex stability.

Preferred are variants having the sequence of any one of SEQ ID NO 3 to SEQ ID NO 93, wherein one, two, three or four nucleobases are substituted by other nucleobases or chemically modified nucleobases. A variant shall refer to a sequence of SEQ ID NO 3 to SEQ ID NO 93, wherein one to four nucleobases are, for instance, substituted by uracile (U), 5-halouracil, 5-methyl-cytosine, and/or N$^6$-methyl-adenine. Especially preferred are variants of SEQ ID NO 3, wherein one, two or three nucleobases are substituted by the above-mentioned moieties.

"Oligonucleotide" refers to an oligomer or polymer of ribonucleic acid (RNA) or deoxyribonucleic acid (DNA) or mimetics or variants thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms, because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides), preferably 9-42, 10-36, 11-32, 12-30, 13-28, 14-26, and most preferably 15-25 nucleobases.

Particularly preferred antisense compounds are antisense oligonucleotides, even more preferably those comprising from about 15 to about 25 nucleobases.

Antisense compounds include ribozymes, external guide sequences (EGS), oligonucleotides (oligozymes), and other short catalytic RNAs or catalytic oligonucleotides which hybridize to the target nucleic acid and inhibit its expression.

The term "salts" refers to physiologically and/or pharmaceutically acceptable salts of the compounds, especially the antisense oligonucleotides of the present invention. Pharmaceutically acceptable base addition salts are formed with inorganic bases are bases. Examples for suitable organic and inorganic bases are bases derived from metal ions, e.g., aluminum, alkali metal ions, such as sodium or potassium, alkaline earth metal ions such as calcium or magnesium, or an amine salt ion or alkali- or alkaline-earth hydroxides, -carbonates or -bicarbonates. Examples include aqueous LiOH, NaOH, KOH, NH$_4$OH, potassium carbonate, ammonia and sodium bicarbonate, ammonium salts, primary, secondary and tertiary amines, such as, e.g., tetraalkylammonium hydroxide, lower alkylamines such as methylamine, t-butylamine, procaine, ethanolamine, arylalkylamines such as dibenzylamine and N,N-dibenzylethylenediamine, lower alkylpiperidines such as N-ethylpiperidine, cycloalkylamines such as cyclohexylamine or dicyclohexylamine, morpholine, glucamine, N-methyl- and N,N-dimethylglucamine, 1-adamantylamine, benzathine, or salts derived from amino acids like arginine, lysine, ornithine or amides of originally neutral or acidic amino acids, chloroprocaine, choline, procaine or the like.

The compounds of the invention which are basic, may form pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Alternatively, the pharmaceutical composition of the invention contains a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, bacculovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (MoMuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957. In order to achieve expression only in the target organ, e.g., brain tissue, the DNA sequences for transcription of the antisense oligonucleotides can be linked to a tissue specific promoter and used for gene therapy.

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds or variants useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage or the replacement of one or more phosphate groups (phosphoric acid group) by a phosphonate (phosphonic acid) group or by sulfate (sulfuric acid) group or by a sulfonate (sulfonic acid) group or by a sulfoxide. A preferred oligonucleotide mimetic is an oligonucleotide mimetic that has been shown to have excellent hybridization properties, and is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone (see, e.g., Nielsen et al., Science 254 (1991), 1497-1500.)

In the context of this invention, "hybridization" means hydrogen bonding, which may be Watson-Crick, Hoogsteen or reversed Hoogsteen hydrogen bonding, between complementary nucleoside or nucleotide bases. As used herein, the term "complementary" refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

In other preferred oligonucleotide mimetics, both the sugar and the internucleoside linkage, i.e. the backbone of the nucleotide units are replaced with novel groups. The base units are maintained for hybridization with an appropriate nucleic acid target compound. An example for such an oligonucleotide mimetic that has been shown to have excellent hybridization properties, is referred to as peptide nucleic acid (PNA). In PNA compounds, the sugar-backbone of an oligonucleotide is replaced with an amide containing backbone, in particular with an aminoethylglycine backbone. The nucleobases are retained and are bound directly or indirectly to aza nitrogen atoms of the amide portion of the backbone.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, hexyl-S-tritylthiol, a thiocholesterol, an aliphatic chain, e.g., dodecandiol or undecyl residues, a phospholipid such as dihexadecyl-rac-glycerol or triethylammonium-1,2-di-O-hexadecyl-rac-glycero-3H-phosphonate, a polyamine or a polyethylene glycol chain, or adamantine acetic acid, a palmityl moiety, or an octadecylamine or hexylamino-carbonyl-oxycholesterol moiety. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

Especially, the present invention relates to the use of the antisense oligonucleotides disclosed herein or variants or mimetics thereof for prophylaxis and treatment of neurodegenerative disorders, neurotrauma, neurovascular and neuroinflammatory incl postinfectious disorders. The term "neurodegenerative disorders and neuroinflammatory disorders" refers to Alzheimer's diseases, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontotemporal dementia, motor neuron disorders, amyotrophic lateral sclerosis, spinal muscular atrophy, spinocerebellar atrophies (SCAs), schizophrenia, affective disorders, major depression, meningoencephalitis, bacterial meningoencephalitis, viral meningoencephalitis, CNS autoimmune disorders, Multiple Sclerosis (MS), acute ischemic/hypoxic lesions incl stroke, CNS trauma, head trauma, arteriosclerosis, atherosclerosis, microangiopathic dementia, Binswanger' disease, leukoaraiosis, retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellar degeneration (OPCD), Shy Drager syndrome (SDS).

More general, the present invention relates to the use of the antisense oligonucleotides disclosed herein or variants or mimetics thereof for treating diseases which are associated with up-regulated or enhanced signalling of TGF-R and/or TGF-$R_{II}$, e.g. through elevated levels of TGF-beta. The antisense oligonucleotides thereby inhibit the expression of TGF-R and/or TGF-$R_{II}$. Instead of the antisense oligonucleotides or in combination with the antisense oligonucleotides, antisense compounds may be used. Antisense compounds refer to vectors as disclosed herein allowing to transcribe an antisense oligonucleotide or to ribozymes, external guide sequences (EGS), oligozymes, and short catalytic RNAs or catalytic oligonucleotides which hybridize to the target nucleic acid encoding TGF-R or TGF-$R_{II}$. Said antisense compounds inhibit the expression of TGF-R or TGF-$R_{II}$. Thus, in said cases the amount of TGF-R and/or TGF-$R_{II}$ present during disease state is decreased.

The antisense oligonucleotides and the antisense compounds disclosed herein are useful for regeneration and functional reconnection of damaged neural pathways and for treatment of various neurodegenerative disorders and neuroinflammatory disorders.

In a further preferred embodiment of the present invention, the compound useful for interfering with the biological activity of TGF-R and/or TGF-$R_{II}$ is a compound reducing or inhibiting the binding of TGF-β1 to its receptor. Preferred examples of such compounds are (neutralizing) antibodies directed against a TGF-R receptor; see Lin et al., 1992, preferably the TGF-β receptor II. The term "antibody", preferably, relates to antibodies which consist essentially of pooled monoclonal antibodies with different epitopic specificities, as well as distinct monoclonal antibody preparations. Monoclonal antibodies are made from an antigen containing, e.g., a fragment of TGF-R or TGF-$R_{II}$ or a corresponding receptor by methods well known to those skilled in the art. As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library. Moreover, antibodies useful for the purposes of the present invention include chimerical, single chain, and humanized antibodies.

Further preferred compounds for the use of the present invention are soluble TGF-β receptors. Such soluble TGFβ receptors are fusion proteins between Fc regions of antibodies and the extracellular domain of TGFβ receptors. Such molecules have a high affinity to soluble TGF-b1. Therefore, the concentration of free TGF-b1 is drastically reduced. According to the manufacturers protocol (R&D Systems, Germany), a DNA sequence encoding the 159 amino acid residue extracellular domain of human TGF-βR$_{II}$ (Lin et al., Cell 1992, 68(4), 775-785) was fused to the Fc region of human IgG1 and the chimeric protein was expressed in a mouse myeloma cell line NSO.

The term "soluble" as used herein in the context of receptors preferably relates to fragments of the receptor only comprising the extracellular domain(s) of the receptor or a part thereof which can still bind its natural ligand, e.g., TGF-β1. The person skilled in the art can determine such fragments based on the known amino acid sequences of the receptors and the determination of the extracellular domain of the receptors can be carried out by use of well known methods, e.g., by computer programs (hydrophilicity plot). In a particular preferred embodiment of the use of the present invention, said soluble TGF-β receptor is the TGF-β receptor II.

The present invention also relates to a method for identifying a compound interfering with (a) the biological activity of TGF-R and/or TGF-R$_{II}$ or the expression of TGF-R and/or TGF-R$_{II}$, or (b) the TGF-β1/TGF-R signaling, comprising the steps of:
(a) incubating a candidate compound with a test system comprising TGF-β1 and neuronal precursor cells; and
(b) assaying the expression of active TGF receptors or the proliferation of the neuronal precursor cells; wherein
(c) an abolition of (i) the suppression of expression of active TGF receptors or (ii) suppression of proliferation of the neuronal precursor cells compared to the test system in the absence of said test compound is indicative of the presence of a candidate compound having the desired properties.

Examples of such candidate molecules include antibodies, oligonucleotides, proteins (e.g., receptors), or mall molecules. Such molecules can be rationally designed using known techniques. Preferably, said test system used for screening comprises substances of similar chemical and/or physical properties, most preferably said substances are identical. The compounds which can be prepared and identified according to a use of the present invention may be expression libraries, e.g., cDNA expression libraries, peptides, proteins, nucleic acids, antibodies, small organic compounds, ligands, hormones, peptidomimetics, PNAs or the like. More recently, WO 98/25146 described further methods for screening libraries of complexes for compounds having a desired property, especially, the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with TGF-R and/or TGF-R$_{II}$ according to the invention or nucleic acid molecules encoding such molecules are, for example, the in vitro screening with the phage display system as well as filter binding assays or "real time" measuring of interaction using, for example, the BIAcore apparatus (Pharmacia). All these methods can be used in accordance with the present invention to identify a compound interfering with the biological activity of TGF-R and/or TGF-R$_{II}$ or the expression of said receptors, or TGβ1/TGF-R signaling.

It is also well known to the person skilled in the art, that it is possible to design, synthesize and evaluate mimetics of small organic compounds that, for example, can act as a substrate or ligand to a TGF-β receptor. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987. The gene encoding TGF-β1 or TGF-R can also serve as a target for screening inhibitors. Inhibitors may comprise, for example, proteins that bind to the mRNA of the gene encoding TGF-R, preferably TGF-R$_{II}$, thereby destabilizing the native conformation of the mRNA and hampering transcription and/or translation. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical interest and for identifying unknown RNA targets for use in treating a disease. These methods and compositions can be used for identifying compounds useful to reduce expression levels of TGF-β1 and/or the corresponding receptor(s). The compounds which can be tested and identified according to the method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 7 (1994), 193-198 and references cited supra). Furthermore, genes encoding a putative regulator of TGF-β1 and/or which excert their effects up- or downstream of TGF-β1 may be identified using, for example, insertion mutagenesis using, for example, gene targeting vectors known in the art. Said compounds can also be functional derivatives or analogues of known inhibitors. Such useful compounds can be for example transacting factors which bind to TGF-R or TGF-R$_{II}$ or regulatory sequences of the gene encoding it. Identification of transacting factors can be carried out using standard methods in the art. To determine whether a protein binds to the protein itself or regulatory sequences, standard native gelshift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with TGF-R or TGF-R$_{II}$ can also be achieved, for example, as described for TGF-β1 in Scofield (Science 274 (1996), 2063-2065) by use of the so-called yeast "two-hybrid system". In this system TGF-β1 is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of, e.g., TGF-R or TGF-$R_{II}$, the complex is able to direct expression of the reporter gene. In this way, e.g., TGF-R or TGF-$R_{II}$ and the gene encoding each receptor can be used to identify peptides and proteins interacting with TGF-R or TGF-$R_{II}$. It is apparent to the person skilled in the art that this and similar systems may then further be exploited for the identification of inhibitors. Finally, the present invention relates to the use of a compound identified by the method described above for the preparation of a pharmaceutical composition for the prevention or treatment of a disease, wherein neurogenesis or neuroregeneration has a beneficial effect. The below example explains the invention in more detail.

The present intervention also relates to methods for identifying the effects of treatment or prevention/prophylaxis at the stem cell/precursor cell population, induced by the modulation of the TGF-R- or TGF-RII-System. This may be especially helpful in establishing successful treatment in the individual patient, allowing for example individualized dosing. The diagnostic methods comprise (a) systemic application of specific antibodies directed against TGF-R or TGF-RII and labelled with either specific nuclids for nuclear medicine diagnostics (Iodine, Technetium, Fluor 18) or with gadolinium salts, perfluorcarbons or other rare earth products/paramagentic compounds/iron particles for use in Magnetic Resonance Imaging. In this context it may be neccessary to shortly open the blood brain barrier at the subependymal layer, in case there is not enough signal over noise ratio; although this area is highly vascularized, and contrast may be enough for visualisation with a 3 Tesla machine, opening of the BBB may be of additional help. This may be either done with i.v. hyperosmolar solutions (e.g. glycerol) or with VEGF (Vascular Endothelial Growth Factor).

(b) systemic application of oligonucleotides (same molecules as mentioned above) specific for TGF-R or TGF-RII: They would be labelled as follows: Gd or $^{111}$In-DTPH (5' XXX XXXXXX3s-Biotin)-(SA-either OX 26, 8D3 or Ak-HIR) (wherebye Gd is used for MRI, $^{111}$In is used for radiodiagnostics; OX 26 is used for mouse experiments and targets the mouse transferrin receptors, 8D3 is a mouse anti rat transferrin receptor antibody, AK-HIR is an antibody directed at the human Insulin receptor). These compounds would only hybridize and signal in those cells that have the active mRNA for TGF-R or TGF-RII. DTPH is used as a chelate-building agent, the Ak-HIR uses the Insulin receptor to shuttle the oligonucleotide through the different barriers, in case of the transferrin receptor antibodies the latter is used for the transmembrane shuttle. There is a differential hybridization stability in those cells where a large number of mRNA is available and therefore a much stronger signal may be detected (Susuki T, Schlachetzki F, et al. J. Nucl. Med. 45: 1766-1775, 2004, Susuki T, Zhang Y, Zhang Y-f, Schlachetzki F, Pardridge et al., Mol. Imaging. 2005, 3, 356-363).

(c) systemic application of oligonucleotides (same molecules as mentioned above) specific for Doublecortin (DCX) with identical labelling as in (b) (cf. WO 2004067751)

Preferably, in a pharmaceutical composition, such compound as described above is combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose. An "effective dose" refers to an amount of the active ingredient that is sufficient to affect the course and the severity of the disease, leading to the reduction or remission of such pathology. An "effective dose" useful for treating and/or preventing these diseases or disorders may be determined using methods known to one skilled in the art. Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. Furthermore, the compounds of the present invention may be mixed and administered together with liposomes, complex forming agents, receptor targeted molecules, solvents, preservatives and/or diluents.

Preferred are pharmaceutical preparations in form of infusion solutions or solid matrices for continuous release of the active ingredient, especially for continous release of at least one antisense oligonucleotide or variants or mimetics thereof. More preferred are pharmaceutical preparations in form of solutions or solid matrices suitable for local administration into the brain.

The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

The present invention relates to pharmaceutical preparations comprising at least one oligonucleotide, variants or mimetics thereof, as disclosed above. Instead of or in addition to the at least one antisense oligonucleotide at least one antisense compound could be present. Antisense compounds refer to vectors allowing to transcribe an antisense oligonucleotide, especially one of the antisense oligonucleotides as disclosed herein or to ribozymes, external guide sequences (EGS), oligozymes, and short catalytic RNAs or catalytic oligonucleotides which hybridize to the target nucleic acid encoding TGF-R or TGF-$R_{II}$. Said antisense compound inhibits the expression of TGF-R or TGF-$R_{II}$ and preferably of is capable of decreasing the amount of TGF-R or TGF-$R_{II}$ formed, respectively.

In a preferred embodiment of the present invention, the disease that can be prevented and/or treated is a neurodegenerative disorder, a neuroinflammatory disorder of the CNS, an acute ischemic or traumatic brain hypoxic brain lesion. Preferred examples of neurodegenerative or neuroinflammatory disorders are Alzheimer's diseases, Parkinson's disease, Creutzfeldt Jakob disease (CJD), new variant of Creutzfeldt Jakobs disease (nvCJD), Hallervorden Spatz disease, Huntington's disease, multisystem atrophy, dementia, frontemporal dementia, motor neuron disorders, amyotrophic lateral sclerosis, spinal muscular atrophy, spinocerebellar atrophies (SCAs), schizophrenia, affective disorders, major depression, meningoencephalitis, bacterial meningoencephalitis and viral meningoencephalitis (prevention of postinflammatory depression of stem cell proliferation), CNS autoimmune disorders, like Multiple Sclerosis (MS), acute ischemic/hypoxic lesions, CNS trauma, head trauma, arteriosclerosis, atherosclerosis, microangiopathic dementia, Binswanger' disease, leukoaraiosis, AIDS-related dementia, fragile X-associated tremor/ataxia syndrome (FXTAS), progressive supranuclear palsy (PSP), striatonigral degeneration (SND), olivopontocerebellear degeneration (OPCD), Shy Drager syndrome (SDS); retinal degeneration, macular degeneration, retinitis pigmentosa, cochlear degeneration, cochlear deafness. Also age dependant decrease of stem cell renewal may be addressed.

EXAMPLES

Example 1

TGF-β1 Inhibits Proliferation of Adult Rodent Neural Stem and Precursor Cells

Adult female mice (various strains) or Fischer-344 rats (3-4 months; Charles River, Germany) are killed, and brains and spinal cords are removed and put in 4° C. DPBS (PAN, Germany) with 4.5 gm/l glucose (Merck, Germany) (DPBS/glu). Overlying meninges and blood vessels are removed. Hippocampus and ependymal zones, including subependymal and subventricular zones from the lateral wall of the lateral ventricle (SVZ), are aseptically removed. The dissected tissue is transferred to fresh DPBS/glu, washed once, transferred to Petri dishes, and dissociated mechanically. The cell suspension is washed in DPBS/glu to rinse off excess blood and resuspended in PPD solution containing 0.01% papain (Worthington Biochemicals, England), 0.1% dispase II (Boehringer Mannheim, Mannheim, Germany), 0.01% DNase I (Worthington Biochemicals), and 12.4 mM $MgSO_4$ in HBSS (PAN) without $Mg_2/Ca_2$ (PAA, Germany) and digested for 30 to 40 minutes at room temperature. The cell suspension is triturated every 10 minutes. Dissociated cells are collected and resuspended in serum-free DMEM/F12 medium containing 2 mM L-glutamine and 0.1 gm/l penicillin/streptomycin and washed three times with accurate trituration. Finally the single-cell suspension is resuspended in NB medium (Gibco BRL, Germany) supplemented with B27 (Gibco BRL) (NB/B27), 2 mM L-glutamine (PAN), 0.1 gm/l penicillin/streptomycin (PAN), 2 g/ml heparin (Sigma, Taufkirchen, Germany), 20 ng/ml bFGF-2 (R&D Systems, Germany), and 20 ng/ml EGF (R&D Systems, Germany). Viable cells are counted by trypan blue exclusion assay in a hemocytometer. Cells are seeded in T-25 culture flasks and cultures are maintained at 37° C. in an incubator with 5% $CO_2$. Single cells begin to form spheres within 5 to 7 days of suspension culture and continue to grow in mass and number during the next weeks. Half of the medium is changed every 7 days. Cells from passage numbers 3 to 20 are used for the experiments (Wachs, F. P., S. Couillard-Despres, et al., Lab Invest 2003, 83(7), 949-962). The cultures of neural stem and precursor cells are further referred to as NSC's. For the dissociation process, the culture medium containing floating neurospheres is collected in a 15-ml centrifuge tube and centrifuged at 120 rcf for 5 minutes. The pellet is resuspended in 200 μl of Accutase (Innovative Cell Technologies Inc., distributed by PAA) and triturated approximately 10 times using a pipette. Then, the cell suspension is incubated at 37° C. for 10 minutes. Dissociated spheres are again triturated and resuspended in 800 μl of NB/B27 medium. Dissociated cells are centrifuged at 120 rcf for 5 minutes and resuspended in NB/B27 medium. An aliquot is counted by trypan blue exclusion assay in a hemocytometer to determine the amount of viable cells. Cells ($10^5$) are plated in T75 culture flasks for long-term passaging (10 ml of culture medium per flask) in NB/B27 medium. The cells obtained after Accutase treatment of primary neurospheres proliferate and yield secondary neurospheres. Secondary neurospheres are passaged 7 to 9 days after plating primary neurosphere cells. Similar to primary cultures and primary neurospheres, single cells obtained after dissociation of secondary neurospheres proliferate and yield tertiary neurospheres (Wachs, F. P., S. Couillard-Despres, et al., Lab Invest 2003, 83(7), 949-962).

Figure 1:
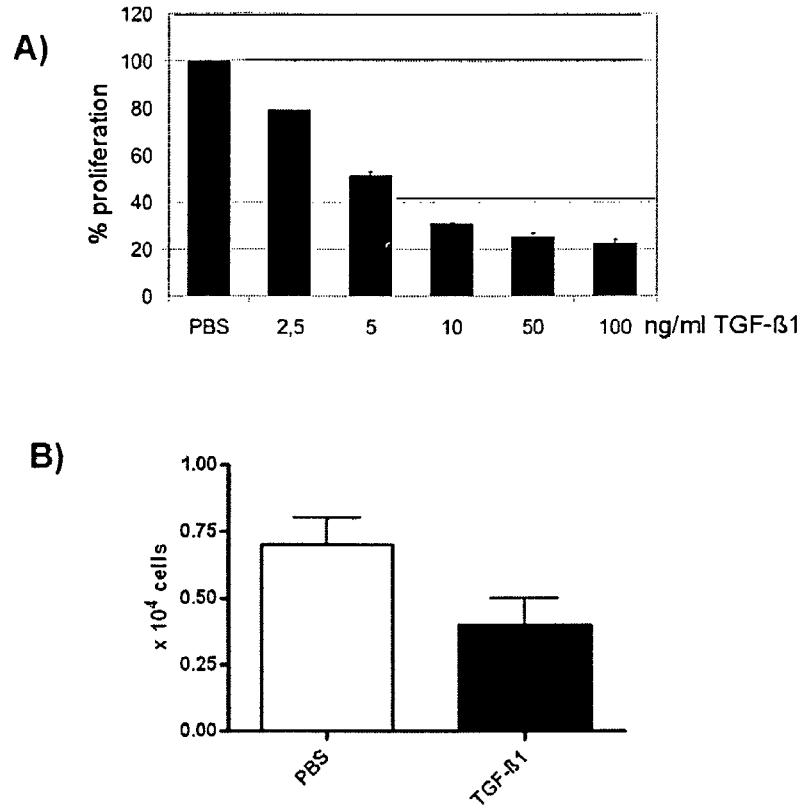
FIG. 1: TGF-beta1 inhibits proliferation of adult rodent neural stem and precursor cells A) Adult rodent neural stem and precursor cell (NSC) cultures were treated with various concentrations (0, 5, 10, 50 ng/ml) of recombinant human TGF-beta1 for 7 days. On day 7 viable cells were counted by Trypan Blue exclusion assay in a hemocytometer. The data are expressed as average cell numbers ±SD from three experiments performed in triplicate. B) shows the effect of TGF-beta1 on human fetal neural precursor cells.

$10^4$ NSC's are seeded in 12-well plates in NB/B27 medium in a volume of 1 ml and grow for 7 days. 2 hours, 3 days and 6 days after seeding the cells are stimulated by addition of various concentrations (0, 2, 5, 5, 10, 50 and 100 ng/ml) of recombinant human Transforming Growth Factor β1 (TGF-β1) (R&D Systems, Germany). On day 7 the cultures are dissociated by the use of Accutase™ and viable cells are counted by trypan blue exclusion assay in a hemocytometer. In vitro TGF-β1 inhibits the proliferation of adult neural stem and precursor cells in a dose dependant manner (FIG. 1A).

A similar effect was observed on human fetal neural precursors cells. Treatment with 50 ng/ml of TGF-b1 reduced cell proliferation to about 50% of controls within 7 days (FIG. 1B).

Example 2

The Effect of TGF-β1 on Neural Stem and Precursor Cells is Reversible

Figure 2:
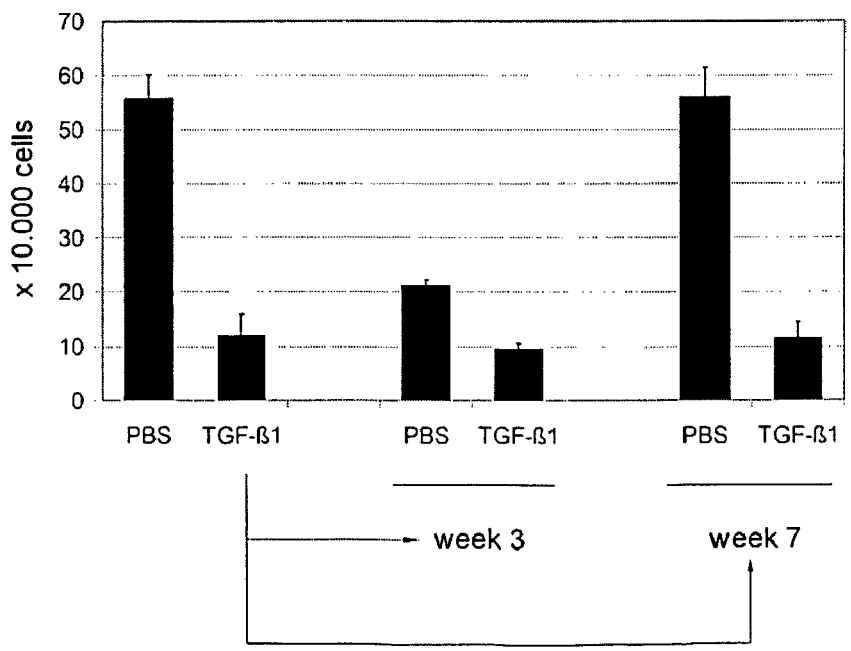
FIG. 2: The effect of TGF-beta1 on NSCs is reversible

To determine, whether the TGF-β1 induced growth-inhibition is a reversible effect, NSC's are stimulated with 10 ng/ml TGF-β1 for 7 days according to the protocol described in example 1. After dissociation, viable cells are counted by Trypan Blue exclusion assay in a hemocytometer and $10^4$ growth factor-stimulated NSC's are reseeded and cultured with or without 10 ng/ml TGF-β1 according to the protocol described in example 1. This dissociation/counting/reseeding procedure is performed every 7 days. As shown in FIG. 2, after 3 weeks of culture the proliferation rate of initially TGF-β1-treated cells now grown without TGF-β1 returns to normal when compared to formerly untreated cells. This indicates that the effect of TGF-β1 on adult neural stem and precursor cells is reversible. Long term incubation with TGF-β1 does not further decrease cell proliferation.

Example 3

Antibodies Against TGF-β$R_{II}$ can Reduce TGF-β1 Effects on Adult Rodent NSC's Unstimulated seven-day-old neurospheres of low passage number are dissociated by the use of Accutase™ as described in example 1. The resulting single-cell suspension was used for blocking analysis. Adult rodent NSC's were seeded at a density of $10^4$ cells in 12-well plates in NB/B27 medium in a volume of 1 ml. 2 hours after seeding and 1 hour prior to stimulation with 10 ng/ml TGF-β1, various concentrations of neutralizing anti-TGF-β$R_{II}$ antibodies (R&D Systems, Germany) were added to the culture medium. 3 days and 6 days after seeding the cells are re-stimulated by addition of anti-TGF-β$R_{II}$ antibodies and TGF-β1 identical to the procedure performed on day 1. On day 7 the cultures are dissociated by the use of Accutase™ and viable cells are counted by trypan blue exclusion assay in a hemocytometer. Interestingly, addition of the anti-TGF-β$R_{II}$ antibodies itself reduces proliferation of NSC's. Antibodies against TGF-β$R_{II}$ are only able to partially inhibit TGF-β1-induced effects even in the highest concentrations used (10 μg/ml) (FIG. 3).

Example 4

Soluble TGF-R$_{II}$ Completely Inhibits TGF-β1 Induced Suppression of NSC Proliferation According to the manufacturers protocol (R&D Systems, Germany), a DNA sequence encoding the 159 amino acid residue extracellular domain of human TGF-βR$_{II}$ (Lin et al., Cell 1992, 68(4), 775-785) was fused to the Fc region of human IgG1 and the chimeric protein was expressed in a mouse myeloma cell line NSO. Unstimulated seven-day-old neurospheres of low passage number are dissociated by the use of Accutase™ as described in example 1. The resulting single-cell suspension was used for blocking analysis. Adult rodent NSC's were seeded at a density of $10^4$ cells in 12-well plates in NB/B27 medium in a volume of 1 ml. 2 hours after seeding and 1 hour prior to stimulation with 10 ng/ml TGF-β1, various concentrations of bioactive soluble recombinant human TGF-βsR$_{II}$/Fc Chimera (R&D Systems, Germany) were added to the culture medium. 3 days and 6 days after seeding the cells are re-stimulated by addition of TGF-βsR$_{II}$/Fc Chimera and TGF-β1 identical to the procedure performed on day 1. On day 7 the cultures are dissociated by the use of Accutase™ and viable cells are counted by trypan blue exclusion assay in a hemocytometer. Interestingly, addition of the TGF-βsR$_{II}$/Fc Chimera are able to completely block TGF-β1-induced effects in a dose dependant manner (data not shown). Clearly, abrogation of active TGF-β1 in the cell culture supernatant by pre-administration of a soluble recombinant human TGF-βsR$_{II}$/Fc Chimera (soluble TGF-βR$_{II}$) completely blocks TGF-β1-induced growth-suppression of adult neural stem and precursor cells (FIG. 4).

Example 5

Figure 5:
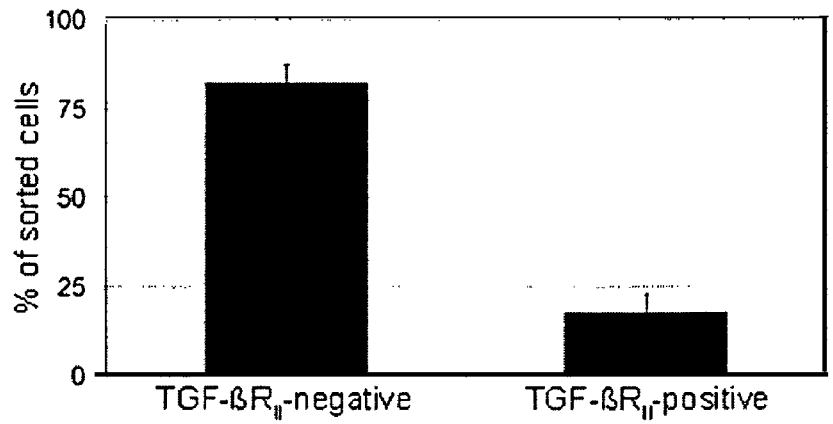

TGF-βR$_{II}$-Expressing Cells can be Isolated Using Cell Sorting Techniques Current methods do not allow fast and reliable isolation and purification of neural stem and precursor cells. To investigate the possibility of isolating pure neural stem and precursor cell populations based on the expression of defined surface markers, we isolate neural stem and precursor cells due to the expression of the TGF-βR$_{II}$ by different techniques. It is possible to isolate TGF-βR$_{II}$-expressing neural stem and precursor cells with two techniques: i) FACS-sorting (data not shown), and ii) MACS-sorting. Dissociated adult neural stem and precursor cells are incubated with 10 μg/ml of primary antibodies against TGF-R$_{II}$ (R&D Systems, Germany) for 20 min at room temperature. After 1 washing step with PBS the cells are incubated with the secondary antibody rabbit-anti-goat-PE (1:500) (Dianova). After 1 washing step with PBS the cells are stained with tertiary antibodies against PE coupled to paramagnetic beads according to the manufacturers protocol (Miltenyi Biotech, Germany). The cell suspension is magnetically sorted using the MACS-system according to the manufacturers protocol (Miltenyi Biotech, Germany) and negative and positive cells after sorting are counted and taken in culture (FIG. 5). Approximately 20% of all sorted cells stained positive for TGF-βR$_{II}$.

Example 6

Antisense Oligonucleotides Against TGF-βRII Inhibit the TGF-β1 Induced Down-Regulation of Adult Neural Stem and Precursor Cell Proliferation In Vitro Cells were prepared, dissociated and plated as described in example 1. Cells were then incubated for 1 week with or without 10 ng/ml TGF-b1, 10 μM TGF-βRII antisense oligonuceotide 5'-cagccccgacccatg-3' (SEQ ID NO: 3), sense oligonucleotide 5'-catgggtcggggctg-3' (SEQ ID NO: 99), or missense 5'-catcccggacccgtg-3' (SEQ ID NO: 100). Oligonucleotides were phosphotihioate-modified and medium with oligonucletodides was changed daily. Note that the TGF-β1 induced inhibition of neural stem and precursor proliferation was completely and specifically blocked by the antisense (SEQ ID NO: 3) treatment (FIG. 6).

Example 7

In Vivo Treatment with TGFRII Specific Antisense Oligonucleotides Rescues the TGF-β1 Induced Blockade of Cell Proliferation in the Adult Brain This example demonstrates i) the effect of TGF-β1 infusion on neural stem and progenitor cell proliferation in vivo and ii) the rescue of this effect by TGFβRII antisense oligonucleotide treatment. Therefore, the following experiment was designed:

TGF-β1 was infused intraventricularly for two weeks followed by a co-infusion of TGF-β1 with oligonucleotides. Animal experiments were carried out in accordance with the European Communities Council Directive of 24 Nov. 1986 (86/609/EEC). Stainless steel canules connected to osmotic minipumps (Model 2001, Alza, Stadt, Land) were implanted into two months-old male Fischer-344 rats (n=24) for intracerebroventricular infusion as described. The animals received either recombinant TGF-β1 (500 ng/ml present in the pump) or artificial cerebrospinal fluid (aCSF) as control (n=8 each) at a flow rate of 0.5 μl/hr for two weeks. After the second week, the pumps were changed and aCSF, TGF-β1 (500 ng/ml present in the pump), or TGF-β1 (500 ng/ml present in the pump) in combination with phosphothioate oligonucleotidies (1.64 mM concentration present in the pump) was infused into the ventricles for the following two weeks. Oligonucleotides were as described in example 6. On day 27, animals received a single intraperitoneal injection of 200 mg/kg bromo-deoxyuridine (BrdU). One day later, animals were intracardially perfused with 4% paraformaldehyde. Tissue was processed for chromogenic or epifluorescence immunodetection in 40 μm sagital sections as described. Epifluorescence analysis was done using a Leica microscope (Leica Mikroskopie and Systeme GmbH, Wetzlar, Germany) equipped with a Spot™ digital camera (Diagnostic Instrument Inc, Sterling Heights, USA) or a confocal scanning laser microscope (Leica TCS-NT, Bensheim, Germany). Primary antibodies were: rat α-BrdU 1:250 (Oxford Biotechnology, Oxford, UK). Secondary antibodies were: donkey α-goat, mouse, rabbit or rat conjugated with fluorescein (FITC), rhodamine X (RHOX), CY5 or biotin 1:500 (Jackson Immuno Research, West Grove, Pa., USA). For counting, a systematic and random procedure was used. BrdU positive cells were counted within three 50 μm×50 μm counting frames per section located at the lowest, middle and upper part of the SVZ. Positive profiles that intersected the uppermost focal plane (exclusion plane) or the lateral exclusion boundaries of the counting frame were not counted. The total counts of positive profiles were multiplied by the ratio of reference volume to sampling volume in order to obtain the estimated number of BrdU-positive cells for each structure. All extrapolations were calculated for one cerebral hemisphere and should be doubled to represent the total brain values. Data are presented as mean values ±standard deviations (SD). Statistical analysis was performed using the unpaired, two-sided t-test comparison—Student's t-test between the TGF-β1 treated and control groups (StatView Software, Cary, N.C., USA). The significance level was assumed at p<0.05.

FIG. 7 demonstrates the TGF-β1 induced down-regulation of cell proliferation in the hippocampal dentate gyrus (FIG. 7A) and in the subventricular zone (FIG. 7B). Treatment with missense oligonucleotide did not block this effect. In contrast, antisense oligonucleotide treatment (SEQ ID NO: 3) blocked the TGF-β1 effect (FIGS. 7 A and B).

Example 8

In Vivo Treatment with TGF-RII Specific Antisense Oligonucleotides Prevents from TGF-β1 Induced Blockade of Cell Proliferation in the Adult Brain This example demonstrates that antisense oligonucleotide treatment against TGF-βRII can prevent from TGF-β1 induced down-regulation of cell proliferation in the adult brain.

Oligonucleotides were infused intraventricularly for one week followed by a co-infusion of TGF-β1 with oligonucleotides. Animal experiments were carried out in accordance with the European Communities Council Directive of 24 Nov. 1986 (86/609/EEC). Stainless steel canules connected to osmotic minipumps (Model 2001, Alza, Stadt, Land) were implanted into two months-old male Fischer-344 rats (n=24) for intracerebroventricular infusion as described. The animals received either phosphothioate oligonucleotidies (1.64 mM concentration present in the pump) or aCSF during the first week, and aCSF, TGF-β1 (500 ng/ml present in the pump), or a co-infusion of TGF-β1 (500 ng/ml present in the pump) and phosphothioate oligonucleotides (1.64 mM concentration present in the pump) during the second and third week. Oligonucleotides were described in example 6. On day 20, animals received a single intraperitoneal injection of 200 mg/kg bromo-deoxyuridine (BrdU). One day later, animals were intracardially perfused with 4% paraformaldehyde. Tissue was processed and analyzed as described in example 7.

FIG. 8 demonstrates that the TGF-β1 induced down-regulation of cell proliferation in the hippocampal dentate gyrus (FIG. 8A) and in the subventricular zone (FIG. 8B) can be prevented by pre-treatment with TGF-βRII antisense oligonucleotide (SEQ ID NO: 3) treatment.

Example 9

Pharmaceutical Formulation Comprising at Least One Antisense Oligonucleotide

Three representative aqueous formulations for the antisense oligonucleotides:
1. in aCSF: 148.0 mM NaCl, 3.0 mM KCl, 1.4 mM $CaCl_2$, 0.8 mM $MgCl_2$, 1.5 mM $Na_2HPO_4$, 0.2 mM $NaH_2PO_4$, pH 7.4, 100 μg/ml rat serum albumin, 50 μg/ml Gentamycin
2. in 0.9% NaCl
3. in $H_2O$

The invention claimed is:

1. A method of promoting successful regeneration and functional reconnection of damaged neural pathways in a mammal, comprising administering a therapeutically or prophylactically effective amount of at least one oligonucleotide having a sequence at least 80% identical to a sub-sequence of SEQ ID NO 1 comprising 8 to 50 nucleobases, wherein said sequence is capable of hybridizing sufficiently with the region encompassing the translation initiation codon of the open reading frame of the gene encoding Transforming growth factor β receptor II.

2. The method according to claim 1, further comprising administrating at least one antisense compound comprising a vector allowing transcription at least one said oligonucleotide or a pharmaceutical formulation comprising at least one said oligonucleotide according to claim 1.

3. The method according to claim 2, wherein at least one said oligonucleotide and/or at least one said antisense compound or said pharmaceutical formulation are used for prophylaxis, therapeutic prevention and treatment of neurodegenerative, traumatic/posttraumatic, vascular/hypoxic, neuroinflammatory and postinfectious Central Nervous System disorders, as well as age induced decreases in neuronal stem cell renewal.

4. The method according to claim 3, wherein the neurodegenerative disorders and neuroinflammatory disorders are selected from the group comprising: Alzheimer's diseases, Parkinson's disease, Creutzfeldt Jakob disease (CJD), new variant of Creutzfeldt Jakobs disease (nvCJD), Hallervorden Spatz disease, Huntington's disease, Multisystem Atrophy, Dementia, Frontemporal Dementia, Amyotrophic Lateral Sclerosis, Spinal Muscular Atrophy, Spinocerebellar Atrophies (SCAs), or other Motor Neuron Disorders, schizophrenia, affective disorders, major depression, meningoencephalitis, Multiple Sclerosis (MS), acute ischemic/hypoxic lesions, stroke, CNS and spinal cord trauma, head and spinal trauma, microangiopathic dementia, Binswanger' disease (Leukoaraiosis), retinal degeneration, cochlear degeneration, macular degeneration, cochlear deafness, AIDS-related dementia, retinitis pigmentosa, fragile X-associated tremor/ataxia syndrome (FXTAS), progressive supranuclear palsy (PSP), striatonigral degeneration (SND), olivopontocerebellar degeneration (OPCD), Shy Drager syndrome (SDS), age dependant memory deficits, neurodevelopmental disorders associated with dementia, Down's Syndrome, synucleinopathies, Superoxide Dismutase Mutations, Trinucleotide Repeat Disorders, trauma, hypoxia, CNS-ageing.

* * * * *